US012805894B2

(12) United States Patent
Golshan

(10) Patent No.: US 12,805,894 B2
(45) Date of Patent: Nov. 24, 2026

(54) DEVICE AND METHOD OF VEIN TREATMENT USING COILED ABRASION ELEMENTS

(71) Applicant: Solvein, Inc., Santa Monica, CA (US)

(72) Inventor: Ali Golshan, Santa Monica, CA (US)

(73) Assignee: Solvein, Inc., Santa Monica, CA (US)

( * ) Notice: Subject to any disclaimer, the term of this patent is extended or adjusted under 35 U.S.C. 154(b) by 0 days.

(21) Appl. No.: 19/299,299

(22) Filed: Aug. 13, 2025

(65) Prior Publication Data

US 2026/0047856 A1 Feb. 19, 2026

Related U.S. Application Data

(60) Provisional application No. 63/682,764, filed on Aug. 13, 2024.

(51) Int. Cl.
*A61B 17/32* (2006.01)
*A61B 17/00* (2006.01)
(Continued)

(52) U.S. Cl.
CPC ........ *A61B 17/32* (2013.01); *A61B 17/00234* (2013.01); *A61B 90/37* (2016.02);
(Continued)

(58) Field of Classification Search
CPC ... A61B 17/32; A61B 17/00234; A61B 90/37; A61B 2017/00238; A61B 2017/00305; A61B 2017/00557; A61B 2017/320004; A61B 2017/320012; A61B 2017/320048; A61M 25/0043; A61M 25/10;
(Continued)

(56) References Cited

U.S. PATENT DOCUMENTS 3,625,793 A 12/1971 Sheridan et al.
4,445,892 A 5/1984 Hussein et al.
(Continued)

FOREIGN PATENT DOCUMENTS

DE 69110467 T2 2/1996
DE 69326572 T2 3/2000
(Continued)

OTHER PUBLICATIONS

Aetna_ Pelvic congestion syndrome: treatments; 20 pages; retrived from the internet (https://www.aetna.com/cpb/medical/data/400_499/0441.html) on Jul. 28, 2023.
(Continued)

*Primary Examiner* — Tan-Uyen T Ho
*Assistant Examiner* — Bridget E. Rabaglia
(74) *Attorney, Agent, or Firm* — Shay Glenn LLP

(57) ABSTRACT

Balloon based therapy devices for treatment of diseased vessels with particular applicability to veins are described. The devices are adapted for active aspiration of a closure zone, in particular aspects to an isolated closure zone, prior to delivery of a closure agent. The devices may be used for treatment of diseased veins in the lower limbs and pelvis. The devices may also include a plurality of angular offset abrasion elements adapted to engage with a vessel wall, such as along a treatment zone.

20 Claims, 38 Drawing Sheets

Section 1-1

(51) Int. Cl.

| | |
|---|---|
| ***A61B 90/00*** | (2016.01) |
| ***A61M 25/00*** | (2006.01) |
| ***A61M 25/10*** | (2013.01) |

(52) U.S. Cl.
CPC ........ *A61M 25/0043* (2013.01); *A61M 25/10* (2013.01); *A61B 2017/00238* (2013.01); *A61B 2017/00305* (2013.01); *A61B 2017/00557* (2013.01); *A61B 2017/00862* (2013.01); *A61B 2017/320004* (2013.01); *A61B 2090/378* (2016.02); *A61B 2217/005* (2013.01); *A61M 2025/1052* (2013.01); *A61M 2025/1086* (2013.01); *A61M 2025/1093* (2013.01); *A61M 2202/0007* (2013.01); *A61M 2205/3379* (2013.01); *A61M 2210/12* (2013.01)

(58) Field of Classification Search
CPC .. A61M 2025/1052; A61M 2025/1086; A61M 2202/0007; A61M 2210/12
See application file for complete search history.

(56) References Cited

U.S. PATENT DOCUMENTS

| | | | |
|---|---|---|---|
| 4,696,668 | A | 9/1987 | Wilcox |
| 4,728,319 | A | 3/1988 | Masch |
| 4,752,286 | A | 6/1988 | Okada |
| 4,876,109 | A | 10/1989 | Mayer et al. |
| 4,895,166 | A | 1/1990 | Farr et al. |
| 4,911,163 | A | 3/1990 | Fina |
| 4,983,166 | A | 1/1991 | Yamawaki |
| 4,990,134 | A | 2/1991 | Auth |
| 5,011,489 | A | 4/1991 | Salem |
| 5,022,399 | A | 6/1991 | Biegeleisen |
| 5,047,013 | A | 9/1991 | Rossdeutscher |
| 5,058,570 | A | 10/1991 | Idemoto et al. |
| 5,074,871 | A | 12/1991 | Groshong |
| 5,085,662 | A | 2/1992 | Willard |
| 5,087,244 | A | 2/1992 | Wolinsky et al. |
| 5,135,517 | A | 8/1992 | McCoy |
| 5,221,255 | A | 6/1993 | Mahurkar et al. |
| 5,226,909 | A | 7/1993 | Evans et al. |
| 5,282,484 | A | 2/1994 | Reger |
| 5,295,959 | A | 3/1994 | Gurbel et al. |
| 5,312,427 | A | 5/1994 | Shturman |
| 5,320,605 | A | 6/1994 | Sahota |
| 5,356,418 | A | 10/1994 | Shturman |
| 5,361,768 | A | 11/1994 | Webler et al. |
| 5,370,653 | A | 12/1994 | Cragg |
| 5,372,601 | A | 12/1994 | Lary |
| 5,383,460 | A | 1/1995 | Jang et al. |
| 5,402,790 | A | 4/1995 | Jang et al. |
| 5,411,478 | A | 5/1995 | Stillabower |
| 5,415,636 | A | 5/1995 | Forman |
| 5,451,206 | A | 9/1995 | Young |
| 5,462,529 | A | 10/1995 | Simpson et al. |
| 5,540,707 | A | 7/1996 | Ressemann et al. |
| 5,549,601 | A | 8/1996 | McIntyre et al. |
| 5,584,843 | A | 12/1996 | Wulfman et al. |
| 5,628,746 | A | 5/1997 | Clayman |
| 5,676,962 | A | 10/1997 | Cabrera Garrido et al. |
| 5,749,858 | A | 5/1998 | Cramer |
| 5,766,192 | A | 6/1998 | Zacca |
| 5,836,905 | A | 11/1998 | Lemelson et al. |
| 5,842,993 | A | 12/1998 | Eichelberger et al. |
| 5,843,103 | A | 12/1998 | Wulfman |
| 5,851,208 | A | 12/1998 | Trott |
| 5,882,329 | A | 3/1999 | Patterson et al. |
| 5,893,858 | A | 4/1999 | Spitz |
| 5,895,400 | A | 4/1999 | Abela |
| 5,902,266 | A | 5/1999 | Leone et al. |
| 5,908,395 | A | 6/1999 | Stalker et al. |
| 5,919,163 | A | 7/1999 | Glickman |
| 5,919,200 | A | 7/1999 | Stambaugh et al. |
| 5,921,963 | A | 7/1999 | Erez et al. |
| 5,961,490 | A | 10/1999 | Adams |
| 6,004,271 | A | 12/1999 | Moore |
| 6,021,340 | A | 2/2000 | Randolph et al. |
| 6,048,332 | A | 4/2000 | Duffy et al. |
| RE36,764 | E | 7/2000 | Zacca et al. |
| 6,090,118 | A | 7/2000 | McGuckin |
| 6,111,614 | A | 8/2000 | Mugura et al. |
| 6,135,991 | A | 10/2000 | Muni et al. |
| 6,159,196 | A | 12/2000 | Ruiz |
| 6,186,146 | B1 | 2/2001 | Glickman |
| 6,193,735 | B1 | 2/2001 | Stevens |
| 6,231,518 | B1 | 5/2001 | Grabek et al. |
| 6,245,040 | B1 | 6/2001 | Inderbitzen et al. |
| 6,258,087 | B1 | 7/2001 | Edwards et al. |
| 6,264,633 | B1 | 7/2001 | Knorig |
| 6,273,882 | B1 | 8/2001 | Whittier et al. |
| 6,290,675 | B1 | 9/2001 | Vujanic et al. |
| 6,306,151 | B1 | 10/2001 | Lary |
| 6,319,227 | B1 | 11/2001 | Mansouri Ruiz |
| 6,398,773 | B1 | 6/2002 | Begaoisan et al. |
| 6,402,745 | B1 | 6/2002 | Wilk |
| 6,485,482 | B1 | 11/2002 | Belef |
| 6,517,528 | B1 | 2/2003 | Pantages et al. |
| 6,520,928 | B1 | 2/2003 | Junior |
| 6,602,264 | B1 | 8/2003 | McGuckin |
| 6,712,798 | B2 | 3/2004 | Constantz |
| 6,733,473 | B1 | 5/2004 | Reifart et al. |
| 6,818,001 | B2 | 11/2004 | Wulfman et al. |
| 6,846,412 | B2 | 1/2005 | Hogan et al. |
| 6,852,118 | B2 | 2/2005 | Shturman et al. |
| 6,926,725 | B2 | 8/2005 | Cooke et al. |
| 7,037,316 | B2 | 5/2006 | McGuckin et al. |
| 7,077,836 | B2 | 7/2006 | Lary et al. |
| 7,083,643 | B2 | 8/2006 | Whalen et al. |
| 7,131,963 | B1 | 11/2006 | Hyde |
| 7,211,073 | B2 | 5/2007 | Fitzgerald et al. |
| 7,285,126 | B2 | 10/2007 | Sepetka et al. |
| 7,402,155 | B2 | 7/2008 | Palasis et al. |
| 7,419,482 | B2 | 9/2008 | Nash et al. |
| 7,479,147 | B2 | 1/2009 | Honeycutt et al. |
| 7,513,886 | B2 | 4/2009 | Konstantino |
| 7,662,143 | B2 | 2/2010 | Carrison et al. |
| 7,670,328 | B2 | 3/2010 | Miller |
| 7,713,231 | B2 | 5/2010 | Wulfman et al. |
| 7,731,986 | B2 | 6/2010 | Wright et al. |
| 7,819,887 | B2 | 10/2010 | McGuckin et al. |
| 7,862,575 | B2 | 1/2011 | Tal |
| 7,909,836 | B2 | 3/2011 | McLean et al. |
| 7,967,834 | B2 | 6/2011 | Tal et al. |
| 8,038,664 | B2 | 10/2011 | Miller et al. |
| 8,062,316 | B2 | 11/2011 | Patel et al. |
| 8,122,917 | B2 | 2/2012 | Harman et al. |
| 8,123,770 | B2 | 2/2012 | Olsen et al. |
| 8,172,783 | B1 | 5/2012 | Ray |
| 8,192,451 | B2 | 6/2012 | Cambronne et al. |
| 8,202,244 | B2 | 6/2012 | Cohen et al. |
| 8,460,214 | B2 | 6/2013 | Kuban et al. |
| 8,491,539 | B2 | 7/2013 | Fojtik |
| 8,632,520 | B2 | 1/2014 | Otley |
| 8,657,821 | B2 | 2/2014 | Palermo |
| 8,690,833 | B2 | 4/2014 | Belson |
| 8,696,645 | B2 | 4/2014 | Tal et al. |
| 8,764,788 | B2 | 7/2014 | Martinez |
| 8,992,482 | B2 | 3/2015 | Foltik |
| 8,992,553 | B2 | 3/2015 | Diamant et al. |
| 9,022,971 | B2 | 5/2015 | Fojtik |
| 9,149,612 | B2 | 10/2015 | Chuter |
| 9,162,037 | B2 | 10/2015 | Belson et al. |
| 9,375,216 | B2 | 6/2016 | Tal et al. |
| 9,440,046 | B2 | 9/2016 | Hobbs et al. |
| 9,457,153 | B2 | 10/2016 | Marano et al. |
| 9,463,304 | B2 | 10/2016 | Agah et al. |
| 9,480,467 | B2 | 11/2016 | Marano et al. |
| 9,480,652 | B2 | 11/2016 | Harman |
| 9,585,667 | B2 | 3/2017 | Tal et al. |
| 9,700,347 | B2 | 7/2017 | Shiber |
| 9,737,329 | B2 | 8/2017 | Shturman |
| RE46,581 | E | 10/2017 | Lafontaine et al. |
| 9,924,957 | B2 | 3/2018 | McGuckin et al. |

(56) References Cited

U.S. PATENT DOCUMENTS

| | | | |
|---|---|---|---|
| 9,962,529 | B2 * | 5/2018 | Konstantino ....... A61M 25/104 |
| 10,207,057 | B2 | 2/2019 | Fojtik |
| 10,285,812 | B2 | 5/2019 | Rowe et al. |
| 10,368,902 | B2 | 8/2019 | Kessler et al. |
| 10,405,878 | B2 | 9/2019 | Wasdyke et al. |
| 10,555,752 | B2 | 2/2020 | Robertson et al. |
| 10,561,439 | B2 | 2/2020 | Silvestro |
| 10,561,440 | B2 | 2/2020 | Look et al. |
| 10,702,300 | B2 | 7/2020 | Higgins et al. |
| 10,722,694 | B2 | 7/2020 | Konstantino et al. |
| 10,786,661 | B2 | 9/2020 | Grace |
| 11,006,935 | B2 | 5/2021 | Brandeis |
| 11,065,029 | B2 | 7/2021 | McMahon et al. |
| 11,420,030 | B2 | 8/2022 | Konstantino et al. |
| 11,529,500 | B2 | 12/2022 | Konstantino et al. |
| 11,696,793 | B2 | 7/2023 | Anderson et al. |
| 11,911,581 | B1 | 2/2024 | Golshan |
| 12,285,174 | B2 | 4/2025 | Golshan |
| 12,329,386 | B2 | 6/2025 | Golshan |
| 12,420,071 | B2 | 9/2025 | Golshan |
| 2001/0023333 | A1 | 9/2001 | Wise et al. |
| 2001/0041909 | A1 | 11/2001 | Tsugita et al. |
| 2002/0010487 | A1 | 1/2002 | Evans et al. |
| 2002/0188276 | A1 | 12/2002 | Evans et al. |
| 2003/0004568 | A1 | 1/2003 | Ken et al. |
| 2003/0078606 | A1 * | 4/2003 | Lafontaine ..... A61B 17/320758 606/167 |
| 2003/0120256 | A1 | 6/2003 | Lary et al. |
| 2003/0225435 | A1 | 12/2003 | Huter et al. |
| 2004/0143287 | A1 * | 7/2004 | Konstantino .. A61B 17/320725 606/194 |
| 2004/0147934 | A1 | 7/2004 | Kiester |
| 2004/0193103 | A1 | 9/2004 | Kumar |
| 2004/0219028 | A1 | 11/2004 | Demarais et al. |
| 2004/0254566 | A1 | 12/2004 | Plicchi et al. |
| 2005/0033227 | A1 | 2/2005 | Brodersen |
| 2005/0059931 | A1 | 3/2005 | Garrison et al. |
| 2006/0149308 | A1 | 7/2006 | Melscheimer |
| 2006/0259062 | A1 * | 11/2006 | Konstantino ....... A61M 25/104 604/103.04 |
| 2007/0016232 | A1 | 1/2007 | St. Martin et al. |
| 2007/0239140 | A1 | 10/2007 | Chechelski et al. |
| 2008/0097224 | A1 | 4/2008 | Murphy et al. |
| 2008/0183129 | A1 | 7/2008 | Silverman et al. |
| 2009/0105645 | A1 | 4/2009 | Kidd et al. |
| 2009/0171284 | A1 | 7/2009 | Burke et al. |
| 2010/0010521 | A1 | 1/2010 | Kurrus |
| 2010/0217313 | A1 | 8/2010 | Raabe et al. |
| 2010/0241148 | A1 | 9/2010 | Schon et al. |
| 2010/0268076 | A1 | 10/2010 | Gat et al. |
| 2011/0125132 | A1 | 5/2011 | Krolik et al. |
| 2011/0152683 | A1 | 6/2011 | Gerrans et al. |
| 2012/0059309 | A1 | 3/2012 | di Palma et al. |
| 2012/0259216 | A1 | 10/2012 | Gerrans et al. |
| 2013/0018396 | A1 | 1/2013 | Gundeson |
| 2013/0030410 | A1 | 1/2013 | Drasler et al. |
| 2013/0041391 | A1 * | 2/2013 | Spencer ......... A61B 17/320725 606/159 |
| 2013/0294189 | A1 | 11/2013 | Myrick et al. |
| 2015/0126965 | A1 | 5/2015 | Liungman |
| 2015/0165169 | A1 | 6/2015 | Mirizzi |
| 2015/0190127 | A1 | 7/2015 | Madsen et al. |
| 2016/0242790 | A1 | 8/2016 | Brandeis |
| 2017/0119428 | A1 | 5/2017 | Boyle et al. |
| 2018/0056051 | A1 * | 3/2018 | Kabra ............... A61M 25/0102 |
| 2018/0099126 | A1 | 4/2018 | Rousu |
| 2018/0333563 | A1 | 11/2018 | Agah et al. |
| 2018/0369539 | A1 | 12/2018 | Rocha-Singh et al. |
| 2019/0365469 | A1 | 12/2019 | Efremkin |
| 2019/0374277 | A1 | 12/2019 | Bagwell et al. |
| 2020/0101269 | A1 * | 4/2020 | Hayes ............. A61B 17/12136 |
| 2020/0113575 | A1 | 4/2020 | Wisnosky et al. |
| 2020/0113577 | A1 | 4/2020 | Wisnosky et al. |
| 2020/0121280 | A1 | 4/2020 | Marshall et al. |
| 2020/0246042 | A1 | 8/2020 | Plowiecki et al. |
| 2020/0269019 | A1 | 8/2020 | Rollins et al. |
| 2021/0022816 | A1 | 1/2021 | DeBuys et al. |
| 2021/0177455 | A1 | 6/2021 | Jamous |
| 2021/0330370 | A1 | 10/2021 | Macaraeg et al. |
| 2022/0105108 | A1 | 4/2022 | Seward |
| 2022/0211983 | A1 | 7/2022 | Giasolli et al. |
| 2022/0296291 | A1 | 9/2022 | Anderson |
| 2022/0370715 | A1 | 11/2022 | Vatemacher et al. |
| 2024/0149020 | A1 | 5/2024 | Golshan |
| 2025/0010043 | A1 | 1/2025 | Golshan |
| 2025/0176966 | A1 | 6/2025 | Golshan |
| 2025/0268600 | A1 | 8/2025 | Golshan |

FOREIGN PATENT DOCUMENTS

| | | | |
|---|---|---|---|
| DE | 19957168 | A1 | 6/2001 |
| DE | 20203840 | U1 | 11/2002 |
| DE | 10233794 | B4 | 12/2004 |
| DE | 69822456 | T2 | 12/2004 |
| EP | 0266928 | A1 | 5/1988 |
| EP | 0501081 | A1 | 9/1992 |
| EP | 0533511 | A1 | 3/1993 |
| EP | 0364799 | B1 | 5/1995 |
| EP | 0533816 | B1 | 6/1995 |
| EP | 0555780 | B1 | 9/1999 |
| EP | 1267989 | B1 | 7/2006 |
| EP | 3275498 | A1 | 1/2018 |
| EP | 3697327 | B1 | 5/2022 |
| FR | 2803532 | A1 | 7/2001 |
| GB | 2494395 | A | 3/2013 |
| JP | 2007301392 | A | 11/2007 |
| JP | 2009254874 | A | 11/2009 |
| JP | 5622938 | B2 | 11/2014 |
| RU | 2699009 | C1 | 9/2019 |
| RU | 196638 | U1 | 3/2020 |
| WO | WO94/021177 | A1 | 9/1994 |
| WO | WO99/004701 | A1 | 2/1999 |
| WO | WO99/047056 | A1 | 9/1999 |
| WO | WO01/008561 | A1 | 2/2001 |
| WO | WO01/28618 | A2 | 4/2001 |
| WO | WO02/05887 | A2 | 1/2002 |
| WO | WO2014/123983 | A2 | 8/2014 |
| WO | WO2023/098708 | A1 | 6/2023 |
| WO | WO2024/045982 | A1 | 3/2024 |
| WO | WO2024/098045 | A1 | 5/2024 |

OTHER PUBLICATIONS

American Medical Association: Code change instructions: 5 pages; retrieved from the Internet (https://www.ama-assn.org/print/pdf/node/3146) on Jul. 28, 2023.

American Medical Association; CPT code change applications; 5 pages; retrieved from the internet (https://www.ama-assn.org/practice-management/cpt/cpt-code-change-applications) on Jul. 28, 2023.

Centers for Medicare & Medacaid Services; CMS-1751-F; 3 pages; retrieved from the internet (https://www.cms.gov/medicaremedicare-fee-service-paymentphysicianfeeschedpfs-federal-regulation-notices/cms-1751-f) on Jul. 28, 2023.

Centers for Medicare & Medicaid Services; Billing and coding: treatment of chronic venous insufficiency of the lower extremities; 10 pages; retrieved from the internet (https://www.cms.gov/medicare-coverage-database/view/article.aspx?articleID=58250&ver=11) on Jul. 28, 2023.

CV Technologies; Flebogrif; 5 pages; retrived from the internet (https://cvtechnologies.in/flebogrif/) on Jul. 28, 2023.

Daniels et al.; Effectiveness of embolization or sclerotherapy of pelvic veins for reducing chronic pelvic pain; Journal of Vascular and Interventional Radiology; 27(10); pp. 1478-1486;75 pages (Author Manuscript); Oct. 2016.

Janatmakan et al.; Effect of local fibrinogen administration on postoperative bleeding in open prostatectomy surgery; Anesthesiology and Pain Medicine; 8(3); e73983; 6 pages; Jun. 2018.

Phlebolymphology; Treatment options for pelvic congestion syndrome; 11 pages; retrieved from the internet (https://www.phlebolymphology.org/treatment-options-pelvic-congestion-syndrome/) on Jul. 28, 2023.

(56) References Cited

OTHER PUBLICATIONS

Picel et al.; Endovascular treatment of pelvic congestion syndrome; 5 pages; retrived from the internet (https://assets.bmctoday.net/evtoday/pdfs/et0418_F11_Picel.pdf) on Jul. 28, 2023.
Teleflex; Arrrow-trerotola; 12 pages; retrieved from the internet (https://studylib.net/doc/8350860/arrow-trerotola%E2%84%A2-ptd%C2%AE-p) on Jul. 28, 2023.
U.S. Food & Drug Administration: Center For Drug Evaluation and research: Varithena / Polidocanol Injectable Foam; 34 pages; retrived from the internet (https://www.accessdata.fda.gov/drugsatfda_docs/nda/2013/205098Orig1s000SumR.pdf) on Jul. 23, 2023.
U.S. Food & Drug Administration; 510(k) Premarket Notification: Clarivein Catheter; 3 pages; retrieved from the internet (https://www.accessdata.fda.gov/scripts/cdrh/cfdocs/cfpmn/pmn.cfm?ID=K071468) on Jul. 28, 2023.
U.S. Food & Drug; Organge book: approved drug products with therapeutic equivalence evaluations: Polidocanol (Varithena) Solutin 180MG/18ML (10MG/ML); 2 pages; retrieved from the internet (https://www.accessdata.fda.gov/scripts/cder/ob/patent_info.cfm?Product_No=001&Appl_No=205098&Appl_type=N) on Jul. 28, 2023.
U.S.Food & Drug Administration; Drug approval package:Varithena; 2 pages; retrieved from (https://www.accessdata.fda.gov/drugsatfda_docs/nda/2013/205098orig1s000toc.cfm) on Jul. 28, 2023.
Varithena; How varithena works; 5 pages; retrieved from the internet (https://www.varithena.com/en-us-hcp/how-it-works.html) on Jul. 23, 2023.
Varithena_Reimbursement Alert; 3 pages; Available as of Apr. 21, 2022—Wayback Machine Archive; retrived from the Internet (https://web.archive.org/web/20220421190800/https://www.varithena.com/content/dam/varithena/hcp/4-3-reimbursement/varithena-2022-medicare-physician-fee-schedule-final-rule.pdf) on Jul. 28, 2023.
Nichols et al.; Importance of balloon size in coronary angioplasty; Journal of the American College of Cardiology; 13(5); pp. 1094-1100; Apr. 1, 1989.
Golshan et al.; U.S. Appl. No. 19/304,220 entitled "Catheters and related methods for the aspiration controlled delivery of closure agents," filed Aug. 19, 2025.

* cited by examiner

Aperture shape and arrangement arranged along shaft
Shapes
302

304

306

308

312
310
314

316

318
330

332

334

HYBRID WIRES

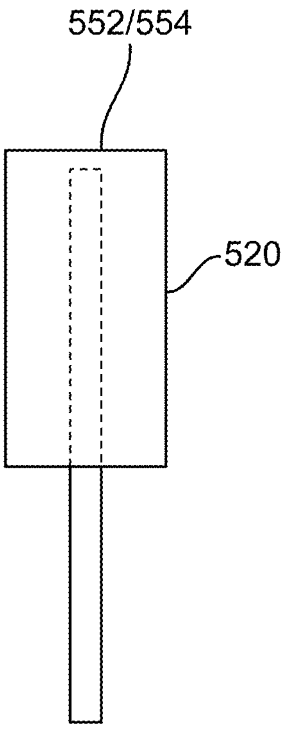
FIG. 16A1
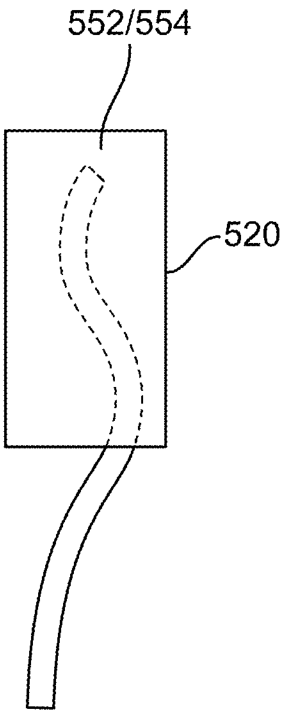
FIG. 16B1
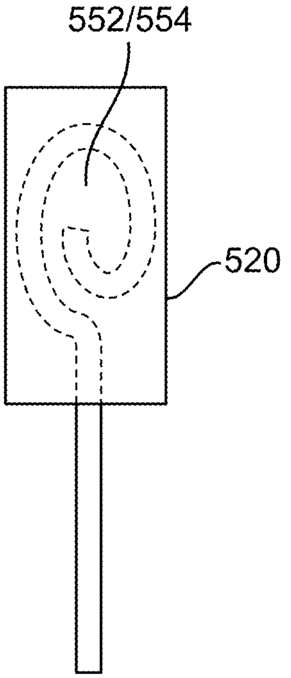
FIG. 16C1
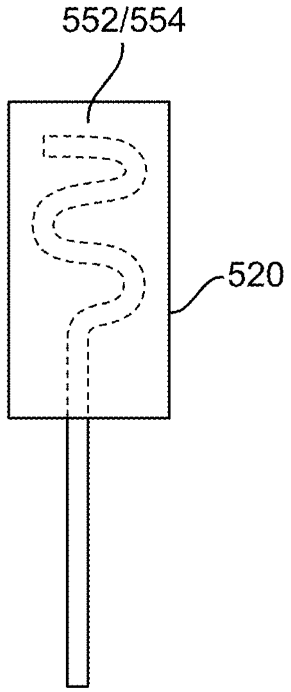
FIG. 16D1

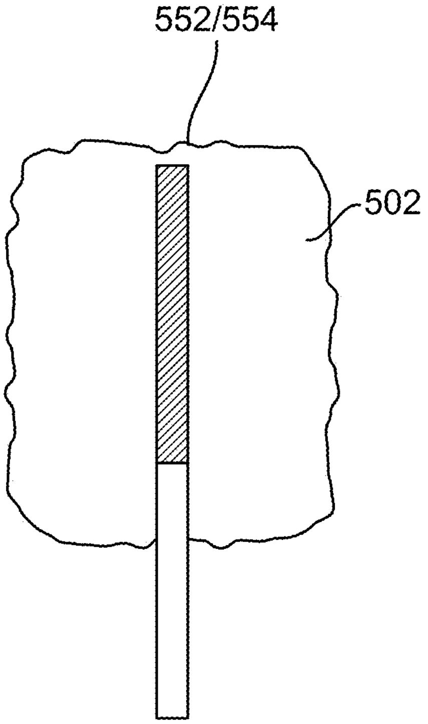
FIG. 16A2
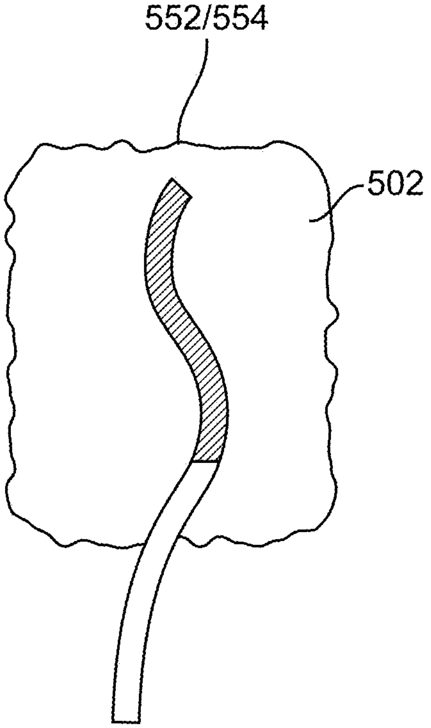
FIG. 16B2
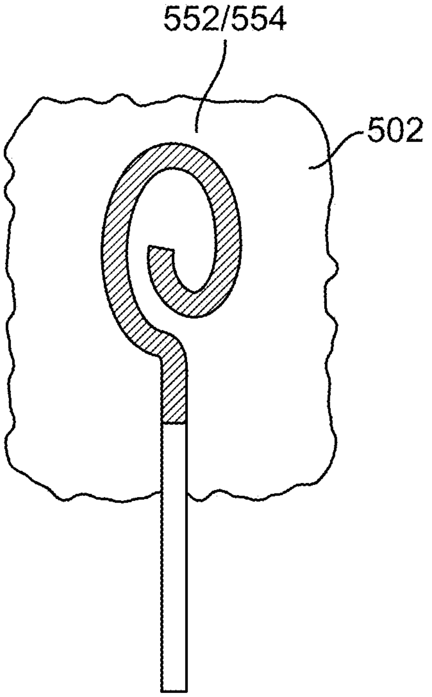
FIG. 16C2
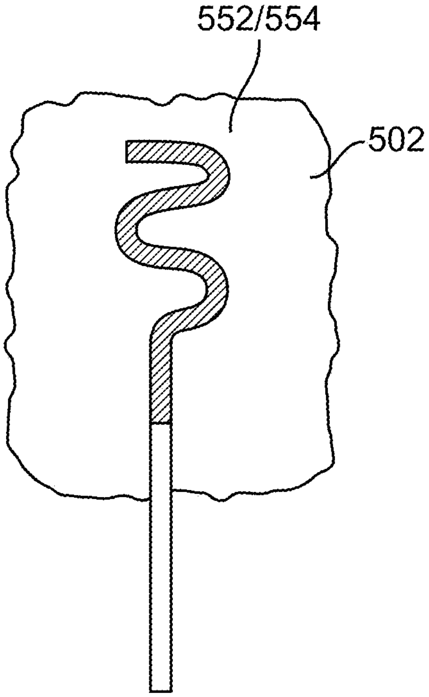
FIG. 16D2

Coil I 12 O'Clock - 3 O'Clock
Coil II 3 O'Clock - 6 O'Clock
Coil III 6 O'Clock - 9 O'Clock
Coil IV 9 O'Clock - 12 O'Clock

2900

DEVICE AND METHOD OF VEIN TREATMENT USING COILED ABRASION ELEMENTS

This application claims priority to U.S. Provisional Patent Application Ser. No. 63/682,764 filed Aug. 13, 2024 entitled "DEVICE AND METHOD OF VEIN TREATMENT USING COILED ABRASION ELEMENTS," the entirety thereof is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

STATEMENT AS TO FEDERALLY SPONSORED RESEARCH

This invention was not made with any Government support.

FIELD

The subject matter disclosed herein generally relates to catheters for the controlled delivery of treatments within the venous vasculature of a mammal.

BACKGROUND

Circulatory issues may be addressed via invasive and non-invasive procedures. For example, currently superficial venous insufficiency (incompetent great saphenous veins) is treated with surgery or radiofrequency ablation (thermal ablation). This requires anesthesia, causes patient pain, and can cause nerve and skin injury. Alternatively, catheters are used to deliver diagnostic and therapeutic agents to internal sites that are typically accessed through the circulatory system in lieu of invasive procedures. For example, foam sclerotherapy (physician compounded) or other physician determined substance can be injected into the vein to cause it to scar shut. However, the injection of foam can lead to delivery of medication to unwanted areas (e.g., healthy veins) leading to injury of healthy veins, such as deep venous thrombosis (DVT) and thrombophlebitis (trapped blood in the treated diseased vein), which can lead to pain and skin injury.

Additionally, because of the distorted shape of the vessel to receive treatment, including distended portions, it is believed that conventional preparatory steps such as elevating the limb or massage of the limb do not sufficiently empty blood and fluids from the treatment zone. The result is that the effectiveness of any injected substance is at least questionable and most likely diminished because of an unknown dilution that occurs because of fluids retained in the limb to be treated.

Prior art devices related to this type of treatment are disclosed in co-pending commonly assigned International Publication Number WO 2024/0908045 entitled "Catheters and Related Methods for Aspiration and Controlled Delivery of Closure Agents" published on May 10, 2024, and invented by Ali Golshan (hereinafter "WO '8045 application" or WO Appl. '8045). FIG. 1 is an example of prior art (see FIGS. 6A and 6B of WO '8045 application). FIG. 1 is the balloon therapy device 600 with the balloon 606 inflated and the collar 632 advanced distally along the catheter by a distance. Inflation of the balloon 606 causes the mechanical abrasion elements 630 to bow radially outward and shorten in an axial direction. This deflection pushes the mechanical abrasion elements 630 into the vessel wall. In this embodiment as well as all other embodiments of the WO '8045 application the proximal and distal ends of the mechanical abrasion elements are longitudinally aligned along the catheter longitudinal axis. Put another way, there is no angular offset between the proximal and the distal ends of the mechanical abrasion elements.

FIG. 2 is an example of one failure mode discovered in previous balloon treatment devices. FIG. 2 is representative of the balloon treatment device in FIGS. 21D-21J of WO '8045 application. The balloon treatment device has a shaft 2122, balloon 2110 with a pair of longitudinally aligned abrasion elements 2120 and an aperture 2116. The abrasion elements are coupled to the catheter distally at cap 2132 and proximally are in sliding relation within abrasion element lumens 2128. During inflation of balloon 2110, one or both abrasion elements deflected laterally so that both abrasion elements are on the same side of the balloon as shown. In use, this produces an undesired result of a treated vessel wall (i.e., one engaged with the abrasion elements) and an untreated vessel wall where there is no contact between the abrasion elements and the vessel wall.

FIGS. 3A and 3B illustrate another failure mode discovered in previous balloon treatment devices. FIG. 3A is a balloon treatment device similar in construction to that of FIG. 2. During normal inflation of the balloon 2110, the abrasion elements 2120 remain along an outer surface of the balloon 2110 and are pressed into contact with the vessel wall while the vessel is distended by the inflated balloon. However, in this improper deployment mode, the abrasion elements 2120 did not deflect and remain on an outer surface of the balloon 2110 but instead deformed the outer balloon wall at least partially around the abrasion element as shown in FIG. 3B. As a result, the abrasion elements do not make the desired contact with the inner wall of the vessel.

In contrast to the prior embodiments, FIGS. 4A and 4B represent embodiments with variations to provide additional abrasion element length to accommodate balloon inflation. (See FIGS. 10 N and 10 O of WO '8045 application) While the abrasion elements remain longitudinally aligned between the proximal and distal ends, the mechanical abrasion elements illustrated can have a curved, undulating, or otherwise non-straight section 1062 along an engagement zone $l_e$ of the mechanical abrasion element. FIGS. 4A and 4B show the catheter shaft 1060, catheter shaft distal end 1061, and the balloon 1064. In comparison to a mechanical abrasion element that extends axially along the balloon, the mechanical abrasion element with the undulations or other non-axially extending portions has a greater effective abrasion zone since the non-axially extending portions have a greater area of contact between abrasion element and the vessel wall than the axially extending abrasion element. When the balloon expands, the undulations may stretch out, but maintain a non-linear shape to increase a surface area of engagement with the vein wall. illustrate an efficiency and potential for over treatment of longitudinally aligned abrasion elements. However, one drawback of such an arrangement is the risk of over treatment since only the leading edges of the abrasion element will contact the vessel wall. Those portions of an abrasion element that trail a leading portion (indicated with thick lines) will make a second or further contact with the vessel wall and potentially risk unintended damage to the vessel wall.

For these and other reasons improvement in the treatment and delivery of material into diseased blood vessels is needed.

SUMMARY OF THE DISCLOSURE

In one embodiment, the present disclosure provides a device, wherein the device may comprise a shaft that may have a proximal end and a distal end, a hub that may be coupled to the proximal end, a balloon that may be on the shaft adjacent to the distal end, an atraumatic tip that may be on the distal end, an aperture that may be in the shaft proximal to the balloon, an inflation lumen that may be within the shaft and may be in fluid communication with an interior volume of the balloon and an inflation port on the hub, and a fluid lumen that may be within the shaft and may be in fluid communication with the aperture and a fluid port on the hub. In further aspects, the device may comprise a plurality of angular offset abrasion elements that may extend along the shaft and over the balloon, wherein each one of the plurality of angular offset abrasion elements may have a proximal terminal end, a distal terminal end, and a tissue contacting surface between the proximal terminal end and the distal terminal end. In still further aspects, the proximal terminal end of each of the plurality of angular offset abrasion elements may be coupled to the shaft proximal to a proximal most end of the balloon and the distal terminal end of each one of the plurality of angular offset abrasion elements may be coupled to the shaft distal to a distal most end of the balloon. In yet further aspects, the distal terminal end of each one of the plurality of angular offset abrasion elements may be at an angular offset from the respective proximal terminal end of each one of the plurality of angular offset abrasion elements.

In a further aspect, the angular offset of each distal terminal end of each one of the plurality of angular offset abrasion elements may be less than 360 degrees, from 2 degrees to 90 degrees, less than 180 degrees, 40 degrees to 60 degrees, or 80 degrees to 100 degrees. In still further aspects, the number of angular offset abrasion elements in the plurality of angular abrasion elements may be 2, and the angular offset of each one of the angular abrasion elements may be from 2 degrees to 180 degrees. In other aspects, the number of angular offset abrasion elements in the plurality of angular abrasion elements may be 3, and the angular offset of each one of the angular abrasion elements may be from 2 degrees to 60 degrees. In yet other aspects, the number of angular offset abrasion elements in the plurality of angular abrasion elements may be 4, and the angular offset of each one of the angular abrasion elements may be from 2 degrees to 90 degrees or from 2 degrees to 50 degrees.

In a further embodiment, the angular offset of the distal terminal end of each one of the plurality of angular offset abrasion elements may be selected so that, in use, the plurality of angular offset abrasion elements may create a plurality of spaced apart abrasion areas along a closure zone. In another aspect, the angular offset of the distal terminal end of each one of the plurality of angular offset abrasion elements may be selected so that, in use, the plurality of angular offset abrasion elements may create a plurality of continuous or nearly continuous abrasion areas along a closure zone.

In yet another embodiment, the number of the plurality of angular offset abrasion elements may be four, wherein a first of the four angular offset abrasion elements may have the proximal terminal end coupled to the shaft at a 12 o'clock position and the corresponding distal terminal end may be coupled to the shaft at a 3 o'clock position, a second of the four angular offset abrasion elements may have the proximal terminal end coupled to the shaft at a 3 o'clock position and the corresponding distal terminal end may be coupled to the shaft at a 6 o'clock position, a third of the four angular offset abrasion elements may have the proximal terminal end coupled to the shaft at a 6 o'clock position and the corresponding distal terminal end may be coupled to the shaft at a 9 o'clock position, and the fourth of the four angular offset abrasion elements may have the proximal terminal end coupled to the shaft at a 9 o'clock position and the corresponding distal terminal end may be coupled to the shaft at a 12 o'clock position.

In one embodiment, the present disclosure provides a device, wherein the device may comprise a shaft that may have a proximal end and a distal end, a hub that may be coupled to the proximal end, a balloon that may be on the shaft adjacent to the distal end, an atraumatic tip that may be on the distal end, an aperture that may be in the shaft proximal to the balloon, an inflation lumen that may be within the shaft and may be in fluid communication with an interior volume of the balloon and an inflation port on the hub, and a fluid lumen that may be within the shaft and may be in fluid communication with the aperture and a fluid port on the hub. In further aspects, the device may comprise four angular offset abrasion elements that may extend along the shaft and over an active area of the balloon, wherein each one of the four angular offset abrasion elements may have a proximal terminal end, and a distal terminal end. In still further aspects, the proximal terminal end of each of the four angular offset abrasion elements may be coupled to the shaft proximal to the active area of the balloon and the distal terminal end of each of the four angular offset abrasion elements may be coupled to the shaft distal to the active area of the balloon. Further still, a position of the proximal terminal end and a position of the distal terminal end of each of the four angular offset abrasion elements may form an angular offset relative to the longitudinal axis of the shaft, wherein the angular offset of each one of the four angular offset abrasion elements may be from 2 degrees to 90 degrees.

In another embodiment, a first of the four angular offset abrasion elements may have the proximal terminal end coupled to the shaft at a 12 o'clock position and the corresponding distal terminal end may be coupled to the shaft at a 3 o'clock position, a second of the four angular offset abrasion elements may have the proximal terminal end coupled to the shaft at a 3 o'clock position and the corresponding distal terminal end may be coupled to the shaft at a 6 o'clock position, a third of the four angular offset abrasion elements may have the proximal terminal end coupled to the shaft at a 6 o'clock position and the corresponding distal terminal end may be coupled to the shaft at a 9 o'clock position, and the fourth of the four angular offset abrasion elements may have the proximal terminal end coupled to the shaft at a 9 o'clock position and the corresponding distal terminal end may be coupled to the shaft at a 12 o'clock position.

In still further aspects, each one of the angular offset abrasion elements may have a coil portion that may comprise a pitch and a coil outer diameter. In a further aspect, the coil portion of each one of the angular offset abrasion elements may be between non-coil portions of the abrasion element. In a still further aspect, the coil portion of each one of the angular offset abrasion elements may be at least as long as the active area of the balloon. In yet another aspect, the angular offset abrasion element may be formed off a wire having a diameter of about 0.05 mm wound into a coil having an outer diameter of 0.2 mm and the pitch of 0.05 mm. Further, the coil portion of each angular offset abrasion element may extend from the proximal terminal end to the distal terminal end.

In a further embodiment, the device, in use, may inflate the balloon to a diameter from 6 mm to 12 mm, wherein the coil portion within each one of the angular offset abrasion elements may remain within an elastic response zone. In a further aspect, the active area of the balloon may have a length of 12-15 mm and the length of each angular offset abrasion element from the proximal terminal end to the distal terminal end may be 20 mm to 40 mm. In still a further aspect, the proximal terminal end and the distal terminal end of each of the angular offset abrasion elements may be coupled to the balloon adjacent to the active area of the balloon.

In another embodiment, the present disclosure provides a method that may comprise accessing a portion of a channel with a device that may comprise a shaft, a balloon on the shaft, and a plurality of angular offset abrasion elements that may extend along the shaft and over the balloon. Next, the method may comprise advancing the device into the channel and forming a proximal end of a closure zone in the channel by partially inflating the balloon to a mechanical treatment volume to engage each one of the plurality of angular offset abrasion elements with an inner wall of the channel. Next, the method may comprise, while maintaining the balloon at the mechanical treatment volume, advancing the device along the closure zone, wherein each one of the plurality of angular offset abrasion elements may form an abrasion area along the closure zone. Next, the method may comprise stopping advancement of the device at a distal end of the closure zone and inflating the balloon to an occlusion volume to occlude the channel. Next, the method may comprise, while maintaining the balloon at the occlusion volume, aspirating a portion of fluid from within the closure zone. Next, the method may comprise injecting a closure agent into the closure zone and maintaining the balloon at the occlusion volume until a closure agent dwell time has elapsed.

In a further aspect, the method may comprise deflating the balloon and disengaging the plurality of angular offset abrasion elements from contact with the inner wall of the channel.

In yet another embodiment, the method may comprise, when advancing the device along the closure zone, abrading the inner wall of the channel along the closure zone. Further, abrading the inner wall may be substantially performed by at least one of the plurality of angular offset abrasion elements. In still further aspects, the method may comprise advancing the device into the channel under ultrasound visualization.

In a still further embodiment, when each one of the plurality of angular offset abrasion elements forms the abrasion area along the closure zone, the plurality of angular offset abrasion elements may create a plurality of spaced apart abrasion areas along the closure zone. In another embodiment, when each one of the plurality of angular offset abrasion elements forms the abrasion area along the closure zone, the plurality of angular offset abrasion elements may create a plurality of continuous or nearly continuous abrasion areas along the closure zone.

In another embodiment, when partially inflating the balloon to the mechanical treatment volume, the method may comprise inflating the balloon to transition the plurality of angular offset abrasion elements from a stowed configuration to a partially deployed configuration.

In a further aspect, the step of aspirating the portion of fluid from within the closure zone may be performed using an aperture proximal to the balloon. In a further aspect, the step of injecting the closure agent into the closure zone may be performed using the aperture.

In a further embodiment, the present disclosure provides a method that may comprise accessing a portion of a channel with a device that may comprise a shaft, a balloon on the shaft, and a plurality of angular offset abrasion elements that may extend along the shaft and over the balloon. Next, the method may comprise advancing the device into the channel and forming a proximal end of a closure zone in the channel by partially inflating the balloon to a mechanical treatment volume to engage each one of the plurality of angular offset abrasion elements with an inner wall of the channel. Next, the method may comprise, while maintaining the balloon at the mechanical treatment volume, advancing the device along the closure zone, wherein each one of the plurality of angular offset abrasion elements may form an abrasion area along the closure zone. Next, the method may comprise stopping advancement of the device at a distal end of the closure zone and inflating the balloon to an occlusion volume to occlude the channel. Next, the method may comprise injecting a closure agent into the closure zone and maintaining the balloon at the occlusion volume until a closure agent dwell time has elapsed.

In a further aspect, the method may comprise deflating the balloon and disengaging the plurality of angular offset abrasion elements from contact with the inner wall of the channel.

In yet another embodiment, the method may comprise, when advancing the device along the closure zone, abrading the inner wall of the channel along the closure zone. Further, abrading the inner wall may be substantially performed by at least one of the plurality of angular offset abrasion elements. In still further aspects, the method may comprise advancing the device into the channel under ultrasound visualization.

In a still further embodiment, when each one of the plurality of angular offset abrasion elements forms the abrasion area along the closure zone, the plurality of angular offset abrasion elements may create a plurality of spaced apart abrasion areas along the closure zone. In another embodiment, when each one of the plurality of angular offset abrasion elements forms the abrasion area along the closure zone, the plurality of angular offset abrasion elements may create a plurality of continuous or nearly continuous abrasion areas along the closure zone.

In another embodiment, when partially inflating the balloon to the mechanical treatment volume, the method may comprise inflating the balloon to transition the plurality of angular offset abrasion elements from a stowed configuration to a partially deployed configuration.

In a further aspect, the step of injecting the closure agent into the closure zone may be performed using the aperture.

In another embodiment, the present disclosure provides a method that may comprise accessing a portion of a channel with a device that may comprise a shaft, a balloon on the shaft, and a plurality of angular offset abrasion elements that may extend along the shaft and over the balloon. Next, the method may comprise advancing the device into the channel and forming a proximal end of a closure zone in the channel by partially inflating the balloon to a mechanical treatment volume to engage each one of the plurality of angular offset abrasion elements with an inner wall of the channel. Next, the method may comprise, while maintaining the balloon at the mechanical treatment volume, advancing the device along the closure zone, wherein each one of the plurality of angular offset abrasion elements may form an abrasion area along the closure zone. Next, the method may comprise stopping advancement of the device at a distal end of the closure zone and inflating the balloon to an occlusion volume to occlude the channel.

In a further aspect, the method may comprise deflating the balloon and disengaging the plurality of angular offset abrasion elements from contact with the inner wall of the channel.

In yet another embodiment, the method may comprise, when advancing the device along the closure zone, abrading the inner wall of the channel along the closure zone. Further, abrading the inner wall may be substantially performed by at least one of the plurality of angular offset abrasion elements. In still further aspects, the method may comprise advancing the device into the channel under ultrasound visualization.

In a still further embodiment, when each one of the plurality of angular offset abrasion elements forms the abrasion area along the closure zone, the plurality of angular offset abrasion elements may create a plurality of spaced apart abrasion areas along the closure zone. In another embodiment, when each one of the plurality of angular offset abrasion elements forms the abrasion area along the closure zone, the plurality of angular offset abrasion elements may create a plurality of continuous or nearly continuous abrasion areas along the closure zone.

In another embodiment, when partially inflating the balloon to the mechanical treatment volume, the method may comprise inflating the balloon to transition the plurality of angular offset abrasion elements from a stowed configuration to a partially deployed configuration.

In a further embodiment, the present disclosure provides a method that may comprise accessing a portion of a channel with a device that may comprise a shaft, a balloon on the shaft, and a plurality of angular offset abrasion elements that may extend along the shaft and over the balloon. Next, the method may comprise advancing the device into the channel and forming a proximal end of a closure zone in the channel by inflating the balloon to have a diameter of at least 6 mm to engage each one of the plurality of angular offset abrasion elements with an inner wall of the channel. Next, the method may comprise advancing the device along the closure zone, wherein each one of the plurality of angular offset abrasion elements may form an abrasion area along the closure zone. Next, the method may comprise stopping advancement of the device at a distal end of the closure zone and inflating the balloon to have a diameter of between 9 mm to 12 mm.

In a further aspect, the method may comprise deflating the balloon and disengaging the plurality of angular offset abrasion elements from contact with the inner wall of the channel.

In yet another embodiment, the method may comprise, when advancing the device along the closure zone, abrading the inner wall of the channel along the closure zone. Further, abrading the inner wall may be substantially performed by at least one of the plurality of angular offset abrasion elements. In still further aspects, the method may comprise advancing the device into the channel under ultrasound visualization.

In a still further embodiment, when each one of the plurality of angular offset abrasion elements forms the abrasion area along the closure zone, the plurality of angular offset abrasion elements may create a plurality of spaced apart abrasion areas along the closure zone. In another embodiment, when each one of the plurality of angular offset abrasion elements forms the abrasion area along the closure zone, the plurality of angular offset abrasion elements may create a plurality of continuous or nearly continuous abrasion areas along the closure zone.

In a further aspect, when inflating the balloon to have the diameter of at least 6 mm, method may comprise inflating the balloon to transition the plurality of angular offset abrasion elements from a stowed configuration to a partially deployed configuration. In a still further aspect, when inflating the balloon to have the diameter of between 9 mm to 12 mm, the plurality of angular offset abrasion elements may transition from the partially deployed configuration to a fully deployed configuration.

In a further embodiment, the present disclosure provides a vein treatment device that may comprise a catheter shaft that may have a longitudinal axis, a proximal end and a distal end, a hub that may be coupled to the proximal end, a balloon that may be on the catheter shaft adjacent to the distal end, an aperture that may be in the catheter shaft proximal to the balloon, an inflation lumen that may be within the catheter shaft and may be in fluid communication with an interior volume of the balloon and an inflation port on the hub, and a fluid lumen that may be within the catheter shaft and may be in fluid communication with the aperture and a fluid port on the hub. In further aspects, the vein treatment device may comprise four mechanical abrasion coils, wherein each of the four mechanical abrasion coils may extend along the catheter shaft and over the balloon, wherein each of the four mechanical abrasion coils may have a proximal terminal end, a distal terminal end, and a tissue contacting surface between the proximal terminal end and the distal terminal end. In still further aspects, the distal terminal end of each of the four mechanical abrasion coils elements may be at an angular offset from the respective proximal terminal end of each one of the four mechanical abrasion coils.

In a further embodiment, the proximal terminal end of each of the four mechanical abrasion coils may be coupled to the catheter shaft proximal to a proximal most end of the balloon and distal to the aperture. Further, the distal terminal end of each one of the four mechanical abrasion coils may be coupled to the catheter shaft distal to a distal most end of the balloon. In a further aspect, a length of each one of the four mechanical abrasion coils between its proximal terminal end and its distal terminal end may be between 20 mm and 40 mm.

In another embodiment, when the vein treatment device is in use, partial inflation of the balloon to a mechanical treatment volume may cause each of the four tissue contacting surfaces to come into contact with a vein wall of a vein, wherein the mechanical treatment volume may be less than a volume of the balloon in a fully inflated occlusion state. In a further aspect, each tissue contacting surface of each of the four mechanical abrasion coils may comprise an undulating segment over the balloon. In a still further aspect, during the partial inflation of the balloon, a non-linear shape of at least a portion of each undulating segment may be maintained.

In a further aspect, a shape of the aperture may be one of a circle, an oval, a rounded rectangular, an elongated rectangular, a narrow slot, or a slit.

In another embodiment, the present disclosure provides a vein treatment device that may comprise a catheter shaft that may have a longitudinal axis, a proximal end and a distal end, a hub that may be coupled to the proximal end, a compliant balloon that may be on the catheter shaft and may be adjacent to the distal end, an aperture that may be in the catheter shaft and may be proximal to the compliant balloon, an inflation lumen that may be within the catheter shaft and may be in fluid communication with an interior volume of the compliant balloon and an inflation port on the hub, and a fluid lumen that may be within the catheter shaft and may be in fluid communication with the aperture and a fluid port on the hub. In further aspects, the vein treatment device may comprise four mechanical abrasion coils, wherein each of the four mechanical abrasion coils may extend along the catheter shaft and over the compliant balloon, wherein each of the four mechanical abrasion coils may have a proximal terminal end, a distal terminal end, and a tissue contacting surface between the proximal terminal end and the distal terminal end. In still further aspects, the distal terminal end of each of the four mechanical abrasion coils elements may be at an angular offset from the respective proximal terminal end of each one of the four mechanical abrasion coils.

In a further aspect, the proximal terminal end of each of the four mechanical abrasion coils may be coupled to the catheter shaft proximal to a proximal most end of the compliant balloon and distal to the aperture. Further, the distal terminal end of each one of the four mechanical abrasion coils may be coupled to the catheter shaft distal to a distal most end of the compliant balloon. In a still further aspect, a length of each one of the four mechanical abrasion coils between its proximal terminal end and its distal terminal end may be between 20 mm and 40 mm.

In yet another embodiment, when the vein treatment device is in use, partial inflation of the compliant balloon to a mechanical treatment volume may cause a portion of each of the mechanical abrasion coils to come into contact with a vein wall of a vein being treated with the vein treatment device, wherein the mechanical treatment volume may be less than a volume of the compliant balloon in a fully inflated occlusion state. In a further aspect, each of the four mechanical abrasion coils may comprise an undulating segment between the proximal terminal end and the distal terminal end of each of the four mechanical abrasion coils and over the complaint balloon. In a still further aspect, during the partial inflation of the compliant balloon, a non-linear shape of at least a portion of each undulating segment may be maintained.

In another aspect, a shape of the aperture may be one of a circle, an oval, a rounded rectangular, an elongated rectangular, a narrow slot, or a slit.

In another embodiment, the present disclosure provides a method for closing a portion of a diseased vein in a patient, wherein the method may comprise accessing a portion of a venous vasculature of the patient with a vein treatment device. In further aspects, the vein treatment device may have a catheter shaft with a longitudinal axis, a compliant balloon on the catheter shaft, and four mechanical abrasion coils. In still further aspects, each of the four mechanical abrasion coils may have a proximal terminal end and a distal terminal end, wherein the proximal terminal end of each of the four mechanical abrasion coils may be coupled to the catheter shaft proximal to a proximal most end of the compliant balloon and the distal terminal end of each one of the four mechanical abrasion coils may be coupled to the catheter shaft distal to a distal most end of the balloon, wherein the distal terminal end of each of the four mechanical abrasion coils elements may be at an angular offset from the respective proximal terminal end of each one of the four mechanical abrasion coils.

In a further aspect, the method may comprise advancing the vein treatment device into a portion of the diseased vein and forming a proximal end of a closure zone in the diseased vein by partially inflating the compliant balloon to a mechanical treatment volume for engagement of a tissue engagement zone of each of the four mechanical abrasion coils between its distal terminal end and its proximal terminal end with an inner wall of the diseased vein.

In still further aspects, the method may comprise, while maintaining the compliant balloon at the mechanical treatment volume, advancing the vein treatment device along the diseased vein to a distal end of the closure zone. In yet a further aspect, the method may comprise inflating the complaint balloon to occlude the diseased vein. In still further aspects, the method may comprise, while occluding the diseased vein, aspirating a portion of fluid from within the closure zone. Further still, the method may comprise injecting a closure agent into the closure zone and maintaining occlusion in the diseased vein until a closure agent dwell time has elapsed.

In yet another embodiment, the method may comprise deflating the balloon and withdrawing the vein treatment device from the patient.

In another aspect, the method may comprise, when advancing the vein treatment device along the diseased vein to the distal end of the closure zone, injuring an endothelial layer and/or loss of endothelial cells of the diseased vein along the closure zone. In a further aspect, injuring the endothelial layer may be performed by the four mechanical abrasion coils.

In a further embodiment, the closure agent dwell time may be from 2-5 minutes. In still further aspects, the elapsed time from performing the step of advancing the vein treatment device into the portion of the diseased vein to completing the step of withdrawing the vein treatment device from the patient may be less than 10 minutes.

In a further embodiment, the step of aspirating the portion of fluid from within the closure zone may be performed using an aperture proximal to the balloon. In a further aspect, the step of injecting the closure agent into the closure zone may be performed using the aperture. In yet another embodiment, a shape of the aperture may be one of a circle, an oval, a rounded rectangular, an elongated rectangular, a narrow slot, or a slit.

In another embodiment, the present disclosure provides a method for closing a portion of a diseased vein in a patient, wherein the method may comprise accessing a portion of a venous vasculature of the patient with a vein treatment device. In a further aspect, the vein treatment device may have a catheter shaft with a longitudinal axis, a compliant balloon on the catheter shaft, and four mechanical abrasion coils. In still further aspects, each of the four mechanical abrasion coils may have a proximal terminal end and a distal terminal end, wherein the proximal terminal end of each of the four mechanical abrasion coils may be coupled to the catheter shaft proximal to a proximal most end of the compliant balloon. Further, the distal terminal end of each one of the four mechanical abrasion coils may be coupled to the catheter shaft distal to a distal most end of the balloon, wherein the distal terminal end of each of the four mechanical abrasion coils elements may be at an angular offset from the respective proximal terminal end of each one of the four mechanical abrasion coils, wherein each of the four mechanical abrasion coils may have a tissue engagement zone between its proximal terminal end and its distal terminal end.

In a further aspect, the method may comprise advancing the vein treatment device into a portion of the diseased vein and partially inflating the balloon to a mechanical treatment volume at a proximal end of a closure zone for engagement of each of the four tissue engagement zones with an inner wall of the diseased vein, such that each of the four tissue engagement zones may engage an inner wall of the diseased vein. In still a further aspect, the method may comprise, while maintaining the balloon at the mechanical treatment volume, advancing the vein treatment device along the diseased vein to a distal end of the closure zone.

In a further embodiment, the method may comprise inflating the balloon to occlude the diseased vein while aspirating a portion of fluid from within the closure zone. In a further aspect, the method may comprise, after aspirating the portion of the fluid within the closure zone, injecting a closure agent into the closure zone. Further, the method may comprise continuing to occlude the diseased vein with the balloon until a closure agent dwell time has elapsed.

In yet another embodiment, the method may comprise deflating the balloon and withdrawing the vein treatment device from the patient.

In another aspect, the method may comprise, when advancing the vein treatment device along the diseased vein to the distal end of the closure zone, injuring an endothelial layer and/or loss of endothelial cells of the diseased vein along the closure zone. In a further aspect, injuring the endothelial layer may be performed by the four mechanical abrasion coils.

In a further embodiment, the closure agent dwell time may be from 2-5 minutes. In still further aspects, the elapsed time from performing the step of advancing the vein treatment device into the portion of the diseased vein to completing the step of withdrawing the vein treatment device from the patient may be less than 10 minutes.

In a further embodiment, the step of aspirating the portion of fluid from within the closure zone may be performed using an aperture proximal to the balloon. In a further aspect, the step of injecting the closure agent into the closure zone may be performed using the aperture. In yet another embodiment, a shape of the aperture may be one of a circle, an oval, a rounded rectangular, an elongated rectangular, a narrow slot, or a slit.

In a further embodiment, the present disclosure provides a device for treatment of an incompetent vein, wherein the device may have a catheter shaft having a proximal end and a distal end, a hub coupled to the proximal end, and a balloon on the catheter shaft adjacent to the distal end, wherein the balloon may be a compliant balloon. The device may further comprise an atraumatic tip on the distal end, an aperture in the catheter shaft proximal to the balloon, an inflation lumen within the catheter shaft in fluid communication with an interior volume of the balloon and an inflation port on the hub, and a fluid lumen within the catheter shaft in fluid communication with the aperture, and a fluid port on the hub. The device may still further comprise a plurality of angular offset abrasion elements extending along the catheter shaft and over the balloon, wherein each one of the plurality of angular offset abrasion elements may comprise a proximal terminal end, a distal terminal end, and a tissue contacting surface between the proximal terminal end and the distal terminal end. Still further, the proximal terminal end of each of the plurality of angular offset abrasion elements may be coupled to the catheter shaft proximal to a proximal most end of the balloon and the distal terminal end of each one of the plurality of angular offset abrasion elements may be coupled to the catheter shaft distal to a distal most end of the balloon. Yet still further, the distal terminal end of each one of the plurality of angular offset abrasion elements may be at an angular offset from the respective proximal terminal end of each one of the plurality of angular offset abrasion elements.

In a further aspect, the angular offset of each distal terminal end of each one of the plurality of angular offset abrasion elements may be less than 360 degrees. In an additional aspect, the angular offset may be from 2 degrees to 90 degrees, less than 180 degrees, 40 degrees to 60 degrees, or 80 degrees to 100 degrees. In further aspects, the number of angular offset abrasion elements in the plurality of angular abrasion elements may be 2, and the angular offset of each one of the angular abrasion elements may be from 2 degrees to 180 degrees.

In another embodiment, the number of angular offset abrasion elements in the plurality of angular abrasion elements may be 3, and the angular offset of each one of the angular abrasion elements may be from 2 degrees to 60 degrees. Furthermore, in one aspect, the number of angular offset abrasion elements in the plurality of angular abrasion elements may be 4, and the angular offset of each one of the angular abrasion elements may be from 2 degrees to 90 degrees. In still further aspects, the number of angular offset abrasion elements in the plurality of angular abrasion elements may be 4, and the angular offset of each one of the angular abrasion elements may be from 2 degrees to 50 degrees.

In yet further embodiments, the angular offset of the distal terminal end of each one of the plurality of angular offset abrasion elements may be selected so that, in use within the incompetent vein, the plurality of angular offset abrasion elements may create a plurality of spaced apart abrasion areas along a closure zone. In still further embodiments, the angular offset of the distal terminal end of each one of the plurality of angular offset abrasion elements may be selected so that, in use within the incompetent vein, the plurality of angular offset abrasion elements may create a plurality of continuous or nearly continuous abrasion areas along a closure zone.

In a further embodiment, the number of the plurality of angular offset abrasion elements may be four. Further, a first of the four angular offset abrasion elements may have the proximal terminal end coupled to the catheter shaft at a 12 o'clock position and the corresponding distal terminal end may be coupled to the catheter shaft at a 3 o'clock position, a second of the four angular offset abrasion elements may have the proximal terminal end coupled to the catheter shaft at a 3 o'clock position and the corresponding distal terminal end may be coupled to the catheter shaft at a 6 o'clock position, a third of the four angular offset abrasion elements may have the proximal terminal end coupled to the catheter shaft at a 6 o'clock position and the corresponding distal terminal end may be coupled to the catheter shaft at a 9 o'clock position, and the fourth of the four angular offset abrasion elements may have the proximal terminal end coupled to the catheter shaft at a 9 o'clock position and the corresponding distal terminal end may be coupled to the catheter shaft at a 12 o'clock position.

In yet another embodiment, the present disclosure provides a device for treatment of an incompetent vein, wherein the device may have a catheter shaft having a proximal end and a distal end, a hub coupled to the proximal end, a balloon on the catheter shaft adjacent to the distal end, wherein the balloon may be a compliant balloon, and an atraumatic tip on the distal end. In further aspects, there may be an aperture in the catheter shaft proximal to the balloon, an inflation lumen within the catheter shaft in fluid communication with an interior volume of the balloon, an inflation port on the hub, and a fluid lumen within the catheter shaft in fluid communication with the aperture and a fluid port on the hub. Additionally, there may be four angular offset abrasion elements extending along the catheter shaft and over an active area of the balloon, wherein each one of the four angular offset abrasion elements may have a proximal terminal end and a distal terminal end. In further aspects, the proximal terminal end of each of the four angular offset abrasion elements may be coupled to the catheter shaft proximal to the active area of the balloon and the distal terminal end of each of the four angular offset abrasion elements may be coupled to the catheter shaft distal to the active area of the balloon. In still further aspects, a position of the proximal terminal end and a position of the distal terminal end of each of the four angular offset abrasion elements may form an angular offset relative to the longitudinal axis of the catheter shaft, further wherein the angular offset of each one of the four angular offset abrasion elements may be from 2 degrees to 90 degrees.

In a further embodiment, a first of the four angular offset abrasion elements may have the proximal terminal end coupled to the catheter shaft at a 12 o'clock position and the corresponding distal terminal end may be coupled to the catheter shaft at a 3 o'clock position, a second of the four angular offset abrasion elements may have the proximal terminal end coupled to the catheter shaft at a 3 o'clock position and the corresponding distal terminal end may be coupled to the catheter shaft at a 6 o'clock position, a third of the four angular offset abrasion elements may have the proximal terminal end coupled to the catheter shaft at a 6 o'clock position and the corresponding distal terminal end may be coupled to the catheter shaft at a 9 o'clock position, and the fourth of the four angular offset abrasion elements may have the proximal terminal end coupled to the catheter shaft at a 9 o'clock position and the corresponding distal terminal end may be coupled to the catheter shaft at a 12 o'clock position.

In yet a further embodiment, each one of the angular offset abrasion elements may have a coil portion having a pitch and a coil outer diameter. In a further aspect, the coil portion of each one of the angular offset abrasion elements may be between non-coil portions of the abrasion element. Further, the coil portion of each one of the angular offset abrasion elements may be at least as long as the active area of the balloon. Still further, the angular offset abrasion element may be formed of a wire having a diameter of about 0.05 mm wound into a coil having an outer diameter of 0.2 mm and the pitch of 0.05 mm.

In still further embodiments, the coil portion of each angular offset abrasion element may extend from the proximal terminal end to the distal terminal end. In additional embodiments, in use within the incompetent vein, when the balloon inflates to an occlusion volume having a diameter from 6 mm to 12 mm, the coil portion within each one of the angular offset abrasion elements may remain within an elastic response zone. In yet further embodiments, the active area of the balloon may have a length of 12-15 mm, and the length of each angular offset abrasion element from the proximal terminal end to the distal terminal end may be 20 mm to 40 mm. Further still, the proximal terminal end and the distal terminal end of each of the angular offset abrasion elements may be coupled to the balloon adjacent to the active area of the balloon.

In one aspect, the present disclosure provides a method for treating an incompetent vein in a patient, wherein the method may comprise accessing a portion of a venous vasculature of the patient with a vein treatment device comprising a catheter shaft, a balloon on the catheter shaft, and a plurality of angular offset abrasion elements extending along the catheter shaft and over the balloon. Next, the method may comprise advancing the vein treatment device into the incompetent vein and forming a proximal end of a closure zone in the incompetent vein by partially inflating the balloon to a mechanical treatment volume to engage each one of the plurality of angular offset abrasion elements with an inner wall of the incompetent vein. Further, the method may comprise, while maintaining the balloon at the mechanical treatment volume, advancing the vein treatment device along the closure zone, wherein each one of the plurality of angular offset abrasion elements may form an abrasion area along the closure zone, and stopping advancement of the vein treatment device at a distal end of the closure zone. Still further, the method may comprise inflating the balloon to an occlusion volume to occlude the incompetent vein, and, while maintaining the balloon at the occlusion volume, aspirating a portion of fluid from within the closure zone. Further still, the method may comprise injecting a closure agent into the closure zone, and maintaining the balloon at the occlusion volume until a closure agent dwell time has elapsed.

In still further embodiments, the method may comprise deflating the balloon and disengaging the plurality of angular offset abrasion elements from contact with the inner wall of the incompetent vein and withdrawing the vein treatment device from the patient.

In yet still further aspects, the method may comprise advancing the vein treatment device along the closure zone by injuring an endothelial layer or a portion of an endothelium of the incompetent vein along the closure zone. Still further, injuring the endothelial layer may be substantially performed by at least one of the plurality of angular offset abrasion elements. Yet further still, the method may comprise advancing the vein treatment device into the incompetent vein under ultrasound visualization.

In yet further aspects, when each one of the plurality of angular offset abrasion elements forms the abrasion area along the closure zone, the method may comprise having the plurality of angular offset abrasion elements create a plurality of spaced apart abrasion areas along the closure zone. In another aspect, when each one of the plurality of angular offset abrasion elements forms the abrasion area along the closure zone, the method may further comprise having the plurality of angular offset abrasion elements create a plurality of continuous or nearly continuous abrasion areas along the closure zone.

In a further embodiment, when partially inflating the balloon to the mechanical treatment volume, the method may comprise inflating the balloon to transition the plurality of angular offset abrasion elements from a stowed configuration to a partially deployed configuration In a still further embodiment, the step of aspirating the portion of fluid from within the closure zone may be performed via an aperture proximal to the balloon. In further aspects, the step of injecting the closure agent into the closure zone may also be performed using the aperture.

In a further embodiment, the present disclosure provides a device for treatment of an incompetent vein, wherein the device may comprise a catheter shaft that may have a proximal end and a distal end, a hub that may be coupled to the catheter shaft proximal end, a balloon that may be on the catheter shaft adjacent to the distal end, wherein the balloon may be a compliant balloon, an atraumatic tip that may be on catheter shaft distal end, an aperture that may be in the catheter shaft proximal to the balloon, an inflation lumen that may be within the catheter shaft and may be in fluid communication with an interior volume of the balloon and an inflation port on the hub, and a fluid lumen that may be within the catheter shaft in fluid communication with the aperture and a fluid port on the hub.

In further aspects, the device may comprise four mechanical abrasion elements that may extending along the catheter shaft and over the balloon, wherein each one of the four mechanical abrasion elements may have a proximal terminal end, a distal terminal end, and a tissue contacting surface between the proximal terminal end and the distal terminal end. Further, the tissue contacting surface may comprise a coil, further wherein the proximal terminal end of each of the four mechanical abrasion elements may be coupled to the catheter shaft proximal to a proximal most end of the balloon and the distal terminal end of each one of the plurality of four mechanical abrasion elements may be coupled to the catheter shaft distal to a distal most end of the balloon.

In further embodiments, the distal terminal end of each of the four mechanical abrasion elements may be at an angular offset from the respective proximal terminal end of each of the four mechanical abrasion elements. In still further aspects, the proximal terminal end and the distal terminal end of each of the four mechanical abrasion elements may be coupled to the catheter shaft to form an angular departure from a longitudinal axis of the catheter. In yet further aspects, the angular departure from the longitudinal axis of the catheter shaft may be from 80 degrees to 100 degrees.

In another embodiment, a first of the four mechanical abrasion elements may have the proximal terminal end coupled to the catheter shaft at a 12 o'clock position and the corresponding distal terminal end may be coupled to the catheter shaft at a 3 o'clock position, a second of the four mechanical abrasion elements may have the proximal terminal end coupled to the catheter shaft at a 3 o'clock position and the corresponding distal terminal end may be coupled to the catheter shaft at a 6 o'clock position, a third of the four mechanical abrasion elements may have the proximal terminal end coupled to the catheter shaft at a 6 o'clock position and the corresponding distal terminal end may be coupled to the catheter shaft at a 9 o'clock position, and the fourth of the four mechanical abrasion elements may have the proximal terminal end coupled to the catheter shaft at a 9 o'clock position and the corresponding distal terminal end may be coupled to the catheter shaft at a 12 o'clock position.

In yet another embodiment, the coil may be formed from a wire having a diameter of about 0.05 mm wound into a coil having a pitch and a coil outer diameter. In further aspects, the coil outer diameter may be 0.2 mm and the pitch may be 0.05 mm. In still further aspects, a coil portion of each mechanical abrasion element may extends from the proximal terminal end to the distal terminal end. In yet further aspects, a coil portion of each mechanical abrasion element may be situated between a non-coiled distal terminal end and a non-coiled proximal terminal end. In still further aspects, a portion of the wire or coil adjacent to the distal terminal end or a portion of the wire or coil adjacent to the proximal terminal end that may be used for coupling to the catheter shaft may be arranged to be along and in alignment to the longitudinal axis of the catheter or may be formed into a simple curve or formed into a coil or formed into a complex curve.

In another embodiment, the present disclosure provides a device for treatment of an incompetent vein, wherein the device may comprise a catheter shaft that may have a proximal end and a distal end, a hub that may be coupled to the catheter shaft proximal end, a balloon that may be on the catheter shaft adjacent to the distal end, wherein the balloon may be a compliant balloon, an atraumatic tip that may be on catheter shaft distal end, an aperture in the catheter shaft that may be proximal to the balloon, an inflation lumen that may be within the catheter shaft and may be in fluid communication with an interior volume of the balloon and an inflation port on the hub, and a fluid lumen that may be within the catheter shaft in fluid communication with the aperture and a fluid port on the hub.

In further aspects, the device may comprise three mechanical abrasion elements that may extend along the catheter shaft and over the balloon, wherein each one of the three mechanical abrasion elements may have a proximal terminal end, a distal terminal end, and a tissue contacting surface between the proximal terminal end and the distal terminal end, wherein the tissue contacting surface may comprise a coil. In further aspects, the distal terminal end of each of the three mechanical abrasion elements may be coupled to the catheter shaft distal to a distal most end of the balloon and the proximal terminal end of each of the three mechanical abrasion elements may be coupled to the catheter shaft proximal to a proximal most end of the balloon.

In yet another aspect, the distal terminal end of each of the three mechanical abrasion elements may be at an angular offset from the respective proximal terminal end of each of the three mechanical abrasion elements. In further aspects, the proximal terminal end and the distal terminal end of each of the three mechanical abrasion elements may be coupled to the catheter shaft to form an angular departure from a longitudinal axis of the catheter. In still further aspects, the angular departure from the longitudinal axis of the catheter shaft may be from 110 degrees to 130 degrees.

In another embodiment, a first of the three mechanical abrasion elements may have the proximal terminal end coupled to the catheter shaft at a 12 o'clock position and the corresponding distal terminal end may be coupled to the catheter shaft at a 4 o'clock position, a second of the three mechanical abrasion elements may have the proximal terminal end coupled to the catheter shaft at a 4 o'clock position and the corresponding distal terminal end may be coupled to the catheter shaft at an 8 o'clock position, a third of the three mechanical abrasion elements may have the proximal terminal end coupled to the catheter shaft at an 8 o'clock position and the corresponding distal terminal end may be coupled to the catheter shaft at a 12 o'clock position.

In yet further aspects, coil may be formed from a wire having a diameter of about 0.05 mm wound into a coil having a pitch and a coil outer diameter. In further aspects, the coil outer diameter may be 0.2 mm. In still further aspects, the pitch may be 0.05 mm. In yet further aspects, a coil portion of each mechanical abrasion element may extend from the proximal terminal end to the distal terminal end. In still further aspects, a coil portion of each mechanical abrasion element may be situated between a non-coiled distal terminal end and a non-coiled proximal terminal end.

In another embodiment, a portion of the wire or coil adjacent to the distal terminal end or a portion of the wire or coil adjacent to the proximal terminal end that may be used for coupling to the catheter shaft may be arranged to be along and in alignment to the longitudinal axis of the catheter or formed into a simple curve or formed into a coil or formed into a complex curve.

In a further embodiment, the present disclosure provides a device for treatment of an incompetent vein, wherein the device may comprise a catheter shaft that may have a proximal end and a distal end, a hub that may be coupled to the catheter shaft proximal end, a balloon that may be on the catheter shaft adjacent to the distal end, wherein the balloon may be a compliant balloon, an atraumatic tip that may be on catheter shaft distal end, an aperture that may be in the catheter shaft proximal to the balloon, an inflation lumen that may be within the catheter shaft in fluid communication with an interior volume of the balloon and an inflation port on the hub, and a fluid lumen that may be within the catheter shaft in fluid communication with the aperture and a fluid port on the hub.

In further aspects, the device may comprise five mechanical abrasion elements that may extend along the catheter shaft and over the balloon, wherein each one of the five mechanical abrasion elements may have a proximal terminal end, a distal terminal end, and a tissue contacting surface between the proximal terminal end and the distal terminal end, wherein the tissue contacting surface may comprise a coil. In still further aspects, the distal terminal end of each of the five mechanical abrasion elements may be coupled to the catheter shaft distal to a distal most end of the balloon and the proximal terminal end of each of the five mechanical abrasion elements may be coupled to the catheter shaft proximal to a proximal most end of the balloon.

In still further aspects, the distal terminal end of each of the five mechanical abrasion elements may be at an angular offset from the respective proximal terminal end of each of the five mechanical abrasion elements.

In other aspects, the proximal terminal end and the distal terminal end of each of the five mechanical abrasion elements may be coupled to the catheter shaft to form an angular departure from a longitudinal axis of the catheter. In still further aspects, the angular departure from the longitudinal axis of the catheter shaft may be from 60 degrees to 85 degrees.

In yet another embodiment, a first of the five mechanical abrasion elements may have the proximal terminal end coupled to the catheter shaft at a 12 o'clock position and the corresponding distal terminal end may be coupled to the catheter shaft between a 2 o'clock and a 3 o'clock position, a second of the five mechanical abrasion elements may have the proximal terminal end coupled to the catheter shaft at between a 2 o'clock and a 3 o'clock position and the corresponding distal terminal end may be coupled to the catheter shaft between a 4 o'clock position and a 5 o'clock position, a third of the five mechanical abrasion elements may have the proximal terminal end coupled to the catheter shaft between a 4 o'clock position and a 5 o'clock position and the corresponding distal terminal end may be coupled to the catheter shaft between a 7 o'clock and an 8 o'clock position, the fourth of the five mechanical abrasion elements may have the proximal terminal end coupled to the catheter shaft a 7 o'clock and an 8 o'clock position and the corresponding distal terminal end may be coupled to the catheter shaft between a 9 o'clock position and a 10 o'clock position, and the fifth of the five mechanical abrasion elements may gave the proximal terminal end coupled to the catheter shaft 9 o'clock position and a 10 o'clock position and the corresponding distal terminal end may be coupled to the catheter shaft near a 12 o'clock position.

In further aspects, the coil may be formed from a wire having a diameter of about 0.05 mm wound into a coil having a pitch and a coil outer diameter. In further aspects, the coil outer diameter may be 0.2 mm and the pitch may be 0.05 mm. In still further aspects, a coil portion of each mechanical abrasion element may extend from the proximal terminal end to the distal terminal end. In yet further aspects, a coil portion of each mechanical abrasion element may be situated between a non-coiled distal terminal end and a non-coiled proximal terminal end.

In a further embodiment, a portion of the wire or coil adjacent to the distal terminal end or a portion of the wire or coil adjacent to the proximal terminal end that may be used for coupling to the catheter shaft may be arranged to be along and in alignment to the longitudinal axis of the catheter or formed into a simple curve or formed into a coil or formed into a complex curve.

In yet another embodiment, the present disclosure provides a method for closing a portion of a diseased vein in a patient, wherein the method comprises accessing a portion of a venous vasculature of the patient with a balloon therapy device having a balloon within a plurality of evenly spaced mechanical abrasion elements comprising coils, advancing the balloon therapy device into a portion of the diseased vein, and forming a proximal end of a closure zone in the diseased vein by partially inflating the balloon to a mechanical treatment volume for engagement with an inner wall of the diseased vein with a portion of each one of the plurality of evenly spaced mechanical abrasion elements comprising coils. In further aspects, the method may comprise, while maintaining the balloon at the mechanical treatment volume, advancing the balloon therapy device along the diseased vein to a distal end of the closure zone. In still further aspects, the method may comprise inflating the balloon to occlude the diseased vein. In yet further aspects, the method may comprise, while occluding the diseased vein, aspirating a portion of fluid from within the closure zone. In still further aspects, the method may comprise injecting a closure agent into the closure zone and maintaining occlusion in the diseased vein until a closure agent dwell time has elapsed.

In further aspects, the method may comprise deflating the balloon and withdrawing the balloon therapy device from the patient.

In a further embodiment, the method may comprise, when advancing the balloon therapy device along the diseased vein to the distal end of the closure zone, injuring an endothelial layer and/or loss of endothelial cells of the diseased vein along the closure zone.

In a still further embodiment, the method may comprise visualizing the balloon therapy device using an ultrasound probe.

In still further aspects, the method may comprise, after the step of injecting the closure agent into the closure zone, performing a step of applying a force from outside of the closure zone to distribute the closure agent along the closure zone. In further aspects, the step of applying force from outside of the closure zone may be performed using an ultrasound probe and under ultrasound imaging. In still further aspects, the step of applying force from outside of the closure zone may distribute the closure agent towards the proximal end of the closure zone and across at least one incompetent vein.

In another embodiment, the method may comprise wherein, after the step of inflating the balloon to the mechanical treatment volume, the coils of at least one mechanical abrasion element may be positioned between a surface of the balloon and a surface of the diseased vein.

In still further aspects, injuring the endothelial layer may be substantially performed by at least one mechanical abrasion element of a mechanical abrasion assembly.

In still other variations the above methods of treating a vein are performed using one of the three coil, four coil or five coil treatment devices described herein.

BRIEF DESCRIPTION OF THE DRAWINGS

FIG. 5A1 is a distal end view of the balloon treatment device of FIG. 5A at section 1-1 showing the distal terminal end of abrasion element C1 at a 12 o'clock position and the distal terminal end of abrasion element C2 at a 6 o'clock position.

FIG. 5A2 is a proximal end view of the balloon treatment device of FIG. 5A at section 2-2 showing the proximal terminal end of abrasion element C1 at the 6 o'clock position and the proximal terminal end of the abrasion element C2 at the 12 o'clock position.

FIG. 6B1 is a distal end view of the balloon treatment device of FIG. 6B at section 1-1 showing the distal terminal end of abrasion element C1 at a 12 o'clock position, the distal terminal end of abrasion element C2 at a 4 o'clock position and the distal terminal end of abrasion element C3 at a 8 o'clock position.

FIG. 6B2 is a proximal end view of the balloon treatment device of FIG. 6B at section 2-2 showing the proximal terminal end of abrasion element C3 at a 12 o'clock position, the proximal terminal end of abrasion element C1 at a 4 o'clock position and the proximal terminal end of abrasion element C2 at a 8 o'clock position.

FIG. 7C1 is a distal end view of the balloon treatment device of FIG. 7C at section 1-1 showing the distal terminal end of abrasion element C1 at a 12 o'clock position, the distal terminal end of abrasion element C2 at a 3 o'clock position, the distal terminal end of abrasion element C3 at a 6 o'clock position, the distal terminal end of abrasion element C4 at a 9 o'clock position.

FIG. 7C2 is a proximal end view of the balloon treatment device of FIG. 7C at section 2-2 showing the proximal terminal end of abrasion element C1 at the 3 o'clock position, the proximal terminal end of the abrasion element C2 at the 6 o'clock position, the proximal terminal end of abrasion element C3 at the 9 o'clock position, the proximal terminal end of the abrasion element C4 at the 12 o'clock position.

FIG. 16A1 is a top view of a portion of a terminal end of a mechanical abrasion element of FIGS. 5A1, 5A2, 6B1, 6B2, 7C1, 7C2 having a linear portion provided for coupling to an outer wall of the delivery catheter beneath a heat shrink segment. The linear portion used to couple to the catheter may be an uncoiled wire portion, a coiled portion with a pitch that is the same as the balloon zone or a coiled portion with a pitch that differs from the pitch along the balloon zone.

FIG. 16B1 is a top view of a portion of a terminal end of a mechanical abrasion element of FIGS. 5A1, 5A2, 6B1, 6B2, 7C1, 7C2 having a simple curved portion provided for coupling to an outer wall of the delivery catheter beneath a heat shrink segment. The simple curved portion used to couple to the catheter may be an uncoiled wire portion, a coiled portion with a pitch that is the same as the balloon zone or a coiled portion with a pitch that differs from the pitch along the balloon zone.

FIG. 16C1 is a top view of a portion of a terminal end of a mechanical abrasion element of FIGS. 5A1, 5A2, 6B1, 6B2, 7C1, 7C2 having a coiled portion provided for coupling to an outer wall of the delivery catheter beneath a heat shrink segment. The coiled portion used to couple to the catheter may be an uncoiled wire portion, a coiled portion with a pitch that is the same as the balloon zone or a coiled portion with a pitch that differs from the pitch along the balloon zone.

FIG. 16D1 is a top view of a portion of a terminal end of a mechanical abrasion element of FIGS. 5A1, 5A2, 6B1, 6B2, 7C1, 7C2 having a complex curved portion provided for coupling to an outer wall of the delivery catheter beneath a heat shrink portion. The complex curved portion used to couple to the catheter may be an uncoiled wire portion, a coiled portion with a pitch that is the same as the balloon zone or a coiled portion with a pitch that differs from the pitch along the balloon zone.

FIG. 16A2 is a top view of a portion of a terminal end of a mechanical abrasion element of FIGS. 5A1, 5A2, 6B1, 6B2, 7C1, 7C2 having a linear portion provided for coupling to an outer wall of the delivery catheter using any suitable fixation technique or optionally in combination with a heat shrink segment. The linear portion used to couple to the catheter may be an uncoiled wire portion, a coiled portion with a pitch that is the same as the balloon zone or a coiled portion with a pitch that differs from the pitch along the balloon zone.

FIG. 16B2 is a top view of a portion of a terminal end of a mechanical abrasion element of FIGS. 5A1, 5A2, 6B1, 6B2, 7C1, 7C2 having a simple curved portion provided for coupling to an outer wall of the delivery catheter using any suitable fixation technique or optionally in combination with a heat shrink segment. The simple curved portion used to couple to the catheter may be an uncoiled wire portion, a coiled portion with a pitch that is the same as the balloon zone or a coiled portion with a pitch that differs from the pitch along the balloon zone.

FIG. 16C2 is a top view of a portion of a terminal end of a mechanical abrasion element of FIGS. 5A1, 5A2, 6B1, 6B2, 7C1, 7C2 having a coiled portion provided for coupling to an outer wall of the delivery catheter using any suitable fixation technique or optionally in combination with a heat shrink segment. The coiled portion used to couple to the catheter may be an uncoiled wire portion, a coiled portion with a pitch that is the same as the balloon zone or a coiled portion with a pitch that differs from the pitch along the balloon zone.

FIG. 16D2 is a top view of a portion of a terminal end of a mechanical abrasion element of FIGS. 5A1, 5A2, 6B1, 6B2, 7C1, 7C2 having a complex curved portion provided for coupling to an outer wall of the delivery catheter using any suitable fixation technique or optionally in combination with a heat shrink segment. The complex curved portion used to couple to the catheter may be an uncoiled wire portion, a coiled portion with a pitch that is the same as the balloon zone or a coiled portion with a pitch that differs from the pitch along the balloon zone.

FIG. 38B makes clear how the distended and damaged walls of varicose veins likely form difficult to drain pockets of blood and fluid. Advantageously, the active aspiration step removes this blood and other fluids to prevent dilution of closure agent when injected.

DETAILED DESCRIPTION

Figure 4A:
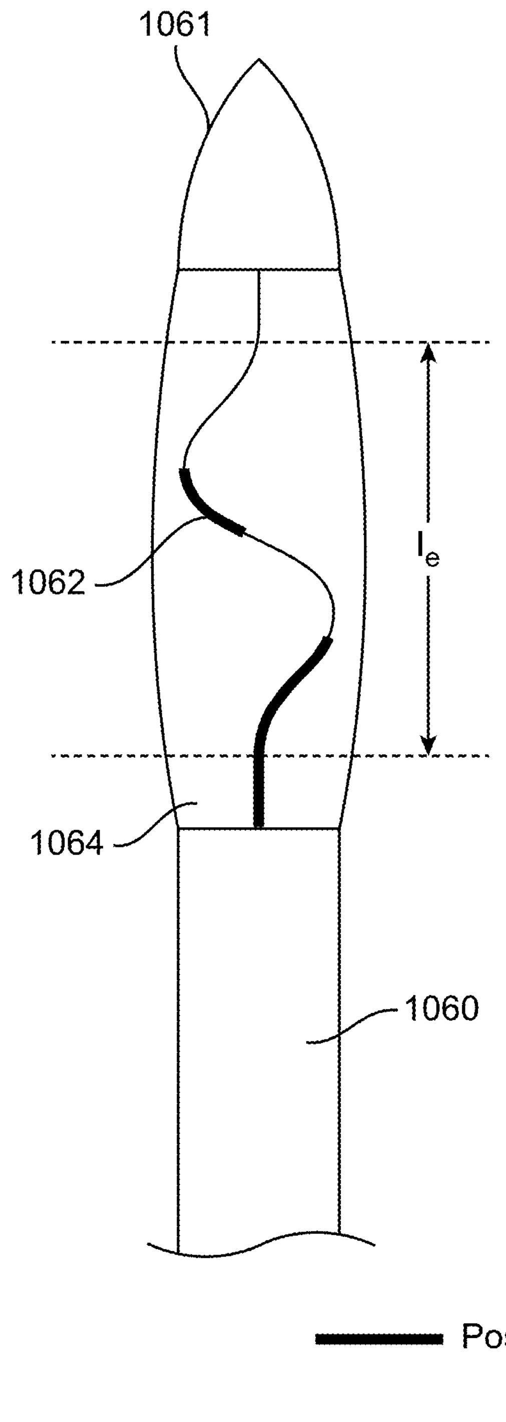
FIG. 4A (PRIOR ART)
FIG. 4A is a top-down view of a balloon treatment device having a longitudinally aligned abrasion element or an abrasion element having no angular offset where the abrasion element contains a pair of undulations to increase contact area with a treatment vessel wall showing the risk of over treatment.
Figure 4B:
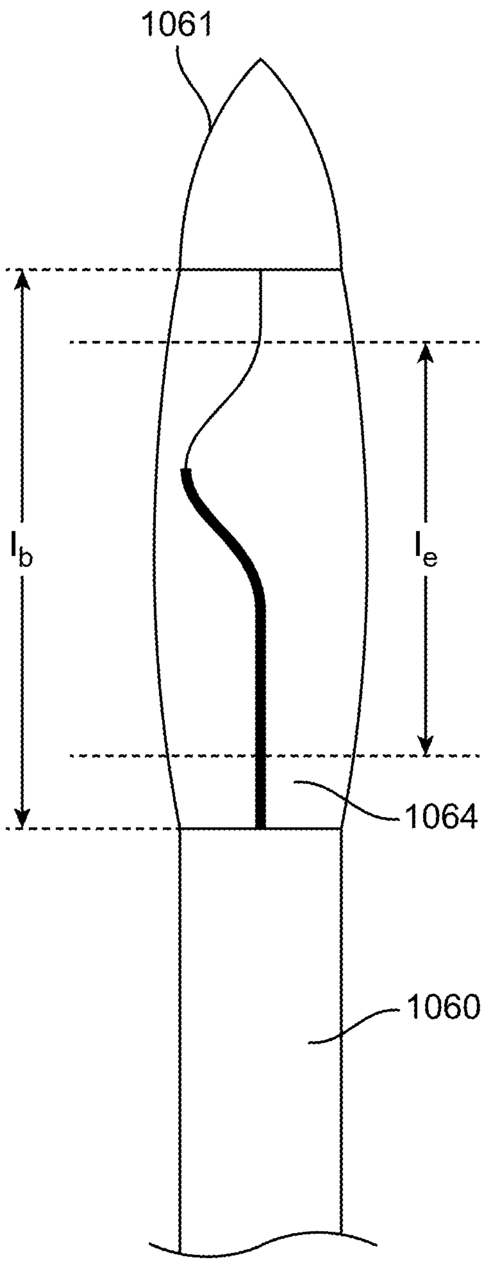
FIG. 4B (PRIOR ART)
FIG. 4B is a top-down view of a balloon treatment device having a longitudinally aligned abrasion element or an abrasion element having no angular offset where the abrasion element contains a single undulation to increase contact area with a treatment vessel wall showing the risk of over treatment.

While there are many advantages to using compliant balloons in vein treatment devices, at least one challenge has emerged. Given compliant nature of the balloon and the small inflation volumes used in vein therapy there has been observed a disproportionate impact in device and mechanical element response due at least in part to balloon wall thickness manufacturing variations. One challenge is that uneven wall distention during inflation can cause mechanical abrasion elements to roll or move out of position. One result is that instead of providing even wall damage during the treatment zone preparation step the abrasion elements are found on one side of the balloon. As a result, new designs of abrasion element spacing have been developed to counteract the so called non-uniform balloon inflation response as discussed above with regard to FIGS. 1-3B. In one aspect, more than two abrasion elements—such as three, four or five elements—are proposed. Additionally, these elements are circumferentially arranged about the balloon and coupled to the catheter shaft proximal and distal to the balloon in an offset manner. Still further, in some embodiments the length of the abrasion element is increased by attaching the proximal and distal terminal ends of an abrasion element at an angular offset relative to the circumference of the catheter. This angular offset—as compared to previous designs that are in axial alignment—increases the length of the abrasion element and because of the angular offset places more of the length of the abrasion element into contact with the vein wall. One advantage of angular offset abrasion elements of the inventive embodiments is mitigation of the potential of vessel wall overtreatment discussed above with regard to FIGS. 4A and 4B. As a result, instead of the two lines of engagement provided by two abrasion elements in line with the axis of the catheter (see e.g., FIG. 33), the angular offset abrasion elements have areas of vein wall engagement related to the amount of angular offset (See, e.g., FIGS. 23, 24B, 25C, 32C and 34.) Still further, another benefit of the angular offset is that the mechanical abrasion elements act as a centering cage of sorts to balance out those non-uniform inflation behaviors observed when using two or more linearly aligned or no angular offset abrasion element designs.

In still other aspects, the angular offset abrasion elements may include a greater variety of coil construction than in previous designs. In one aspect an angular offset abrasion element may have a coil construction of a single wire wound at a constant pitch along the entire length from a proximal terminal end to a distal terminal end (see FIGS. 11B, 12A). In one aspect an angular offset abrasion element may have a coil construction of a single wire wound at a constant pitch only in a central portion of the entire length—corresponding to the contact area with the vein wall or an active area of a balloon—while the rest of the abrasion element is formed only from non-coiled wire (See, e.g., FIGS. 14A, 15A). In still another aspect an angular offset abrasion element may have a coil construction of a single wire wound at the same pitch but spaced apart (FIG. 13A) or different selected pitch along part of or the entire length from a proximal distal end to a distal terminal end (See, e.g., FIGS. 13B and 13C). In this way there may be a pitch selected for engagement to the vein wall to fine tune the amount of damage caused to the vein wall in a treatment zone and then another coil pitch on the proximal distal end and the distal terminal ends to aid in coupling to the catheter wall (i.e., increasing the surface area for engagement or to prevent pullout, see FIGS. 16A1-16D2). These variations and other advantages are to be appreciated in the various embodiments that follow.

Figures 5A, 6B, 7C:
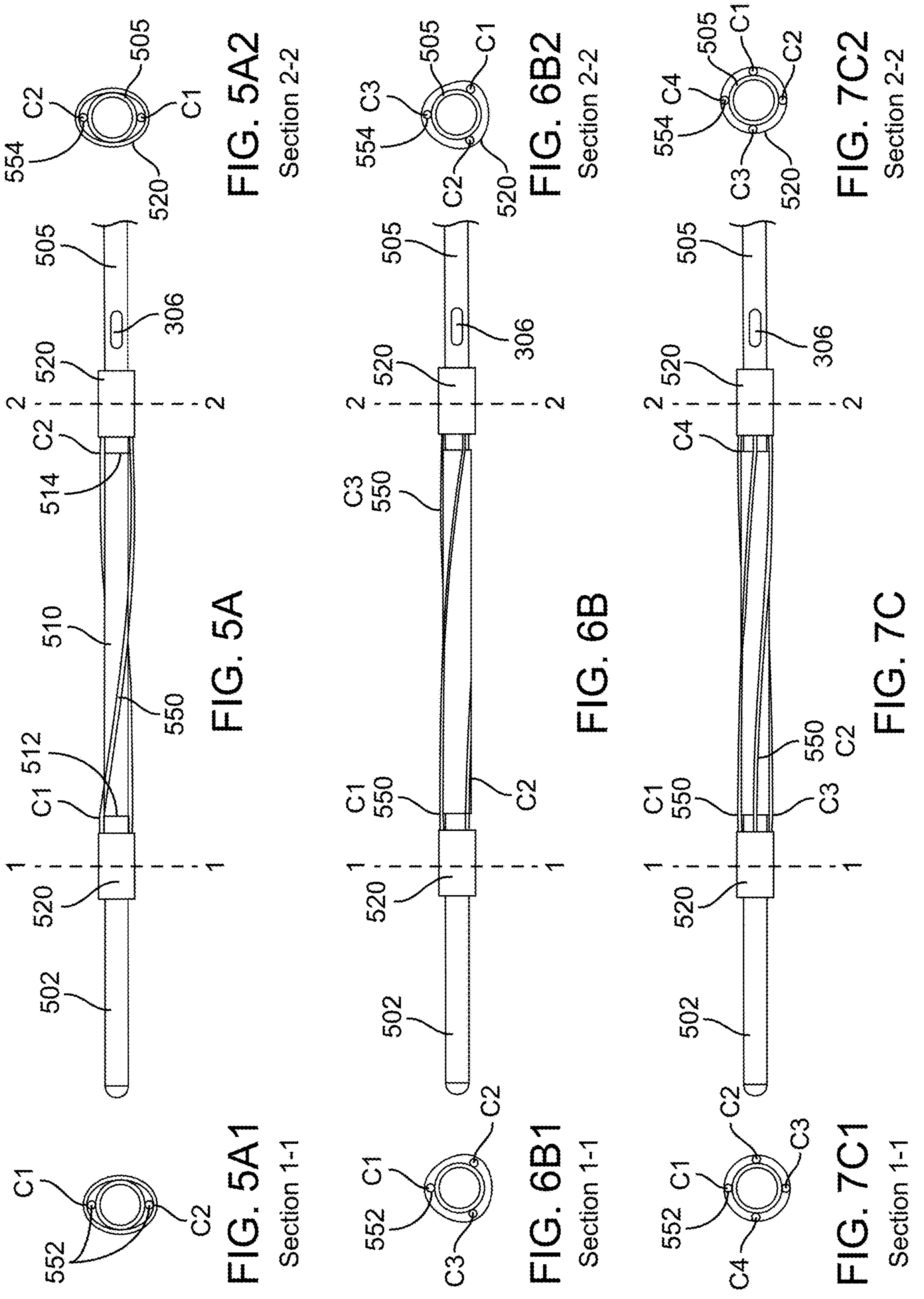
FIG. 5A is a top-down view of a balloon treatment device having a pair of longitudinally offset abrasion elements or abrasion elements with an angular offset between the proximal terminal end and the distal terminal end of 180 degrees.
FIG. 6B is a top-down view of a balloon treatment device having three longitudinally offset abrasion elements or abrasion elements with an angular offset between the proximal terminal end and the distal terminal end of 60 degrees.
FIG. 7C is a top-down view of a balloon treatment device having a four longitudinally offset abrasion elements or abrasion elements with an angular offset between the proximal terminal end and the distal terminal end of 90 degrees.

FIG. 5A is a top-down view of a balloon treatment device 500 having a pair of longitudinally offset abrasion elements or abrasion elements 550 with an angular offset between the proximal terminal end 554 and the distal terminal end 552 of 180 degrees. The proximal terminal end 554 and the distal terminal end 552 of the abrasion elements 550 are underneath the heat shrink coupling 520 in the views of FIGS. 5A, 6B and 7C.

Figure 1:
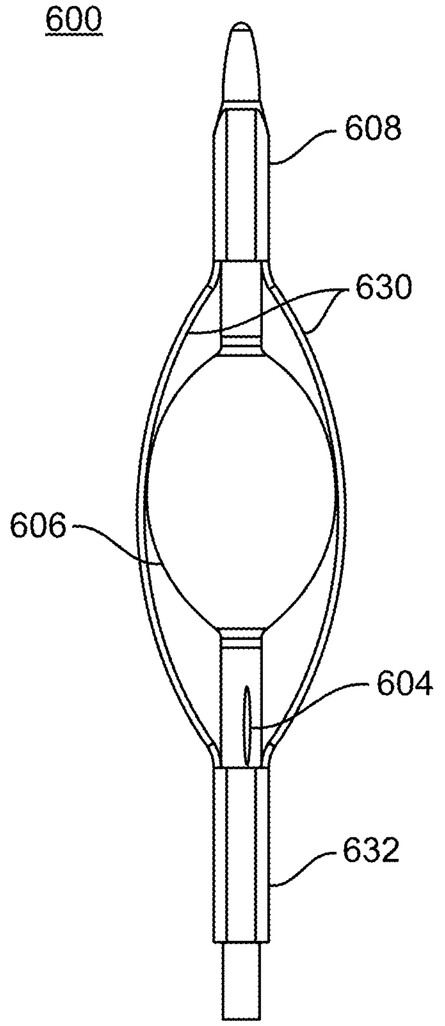
FIG. 1 (PRIOR ART)
FIG. 1 is a view of a prior art balloon treatment device having longitudinally aligned abrasion elements or abrasion elements having no angular offset.

FIG. 5A1 is a distal end view of the balloon treatment device 500 of FIG. 5A at section 1-1 showing the distal terminal end 552 of abrasion element C1 at a 12 o'clock position and the distal terminal end 552 of abrasion element C2 at a 6 o'clock position. It is to be appreciated that the views of the proximal and distal terminal ends 552, 554 illustrated in FIGS. 5A1, 5A2, 6B1, 6B2, 7C1 and 7C2 are shown with the heat shrink segment 520 spaced apart from the catheter wall 550 for clarity and explanation of the arrangement of the components of the balloon treatment device. In use, after the heat shrink or other bonding process is completed the heat shrink segment 520 should be conformal to the profiles of the abrasion elements as well as provide a smooth transition from the terminal ends 552, 554 to the catheter shaft 505.

Figure 2:
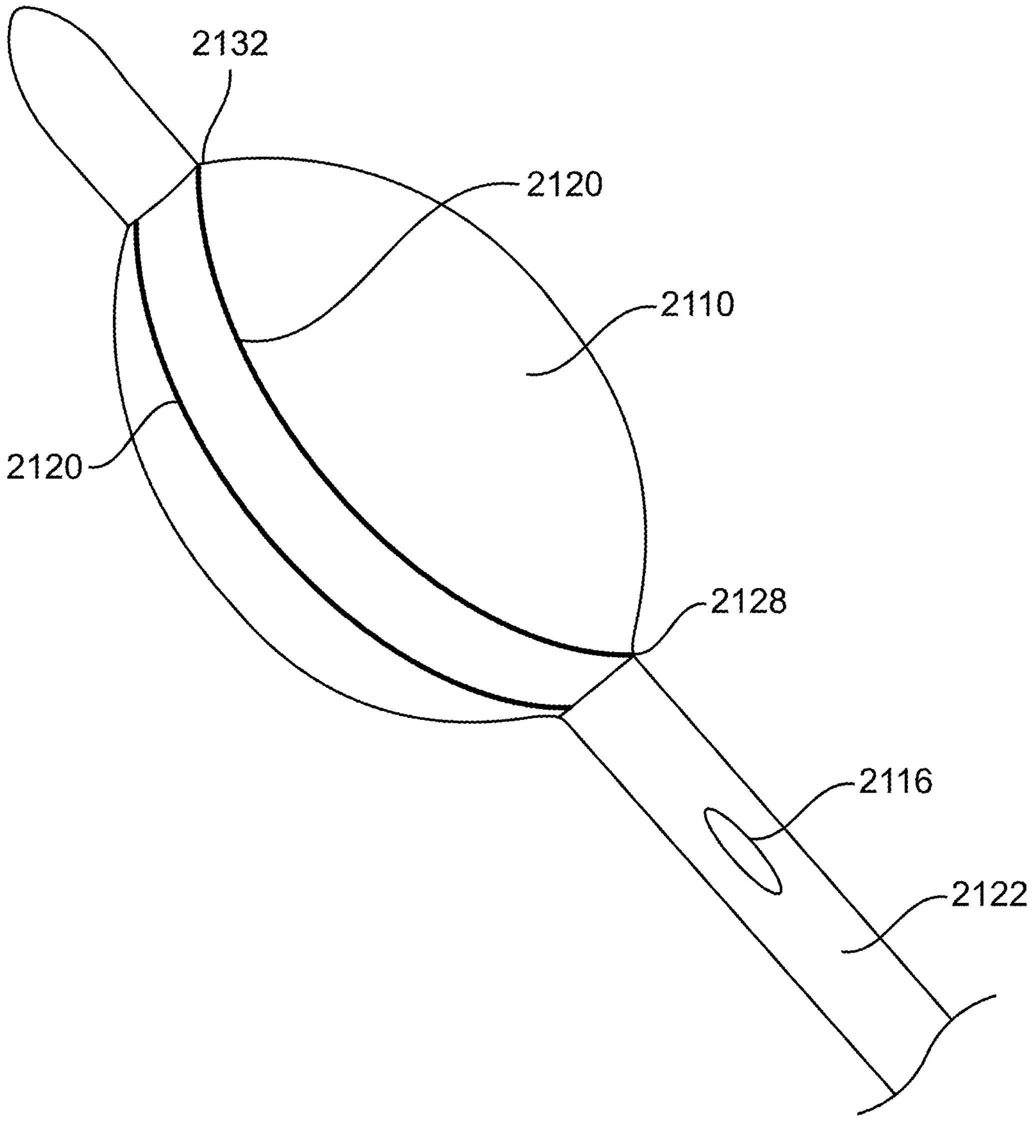
FIG. 2 (PRIOR ART)
FIG. 2 is a perspective view of a failure mode of a balloon treatment device having longitudinally aligned abrasion elements or abrasion elements having no angular offset where the abrasion elements deflect to one side as the balloon is inflated.
Figure 3A:
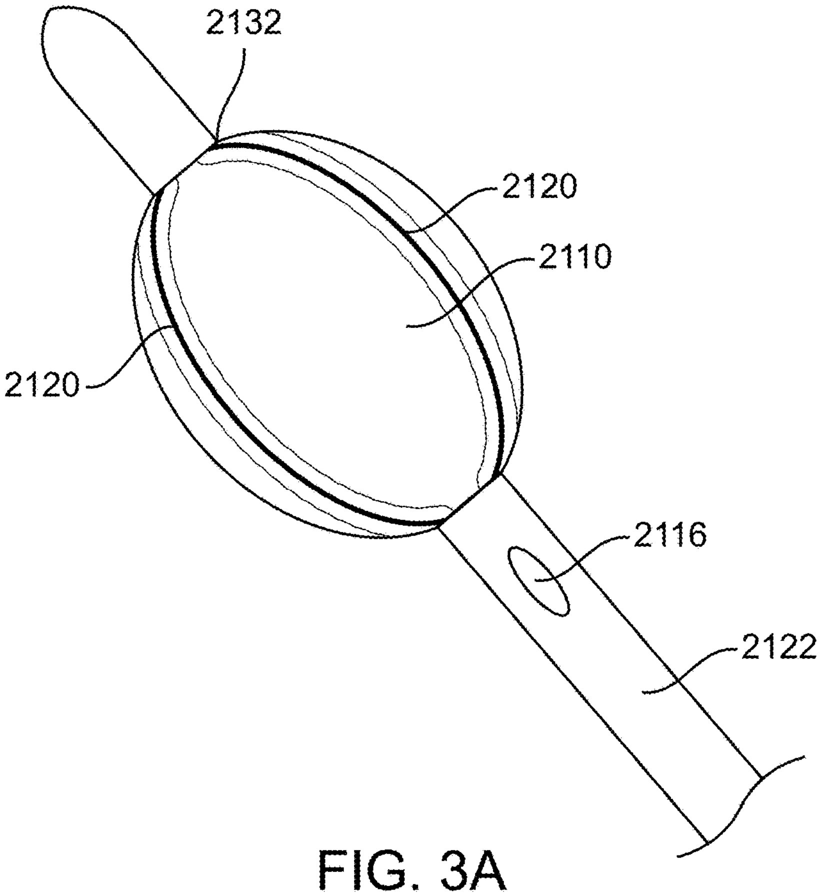
FIG. 3A (PRIOR ART)
FIG. 3A is perspective view of a failure mode of a balloon treatment device having longitudinally aligned abrasion elements or abrasion elements having no angular offset where the abrasion elements do not deflect as the balloon is inflated but instead cause detents into the balloon surface.
Figure 3B:
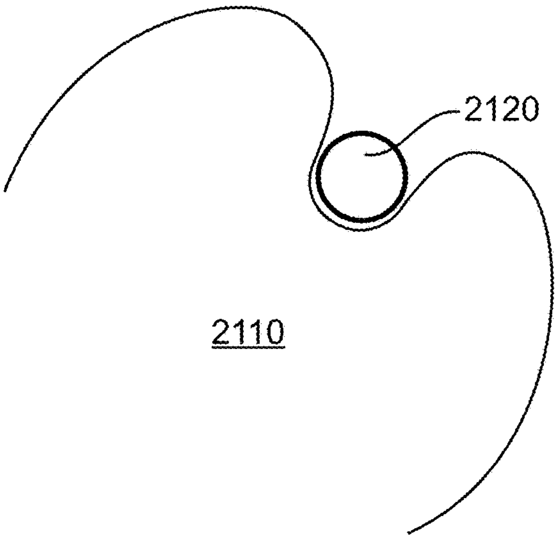
FIG. 3B (PRIOR ART)
FIG. 3B is a section view of an abrasion element deflecting into the surface of a balloon as shown in FIG. 3A.

FIG. 5A2 is a proximal end view of the balloon treatment device of FIG. 5A at section 2-2 showing the proximal terminal end 554 of abrasion element C1 at the 6 o'clock position and the proximal terminal end 554 of the abrasion element C2 at the 12 o'clock position.

FIG. 6B is a top-down view of a balloon treatment device 600 having three longitudinally offset abrasion elements or abrasion elements 550 with an angular offset between the proximal terminal end 554 and the distal terminal end 552 of 60 degrees.

FIG. 6B1 is a distal end view of the balloon treatment device of FIG. 6B at section 1-1 showing the distal terminal end 552 of abrasion element C1 at a 12 o'clock position, the distal terminal end 552 of abrasion element C2 at a 4 o'clock position and the distal terminal end 552 of abrasion element C3 at an 8 o'clock position.

FIG. 6B2 is a proximal end view of the balloon treatment device 600 of FIG. 6B at section 2-2 showing the proximal terminal end 554 of abrasion element C3 at a 12 o'clock position, the proximal terminal end 554 of abrasion element C1 at a 4 o'clock position and the proximal terminal end 554 of abrasion element C2 at an 8 o'clock position.

FIG. 7C is a top-down view of a balloon treatment device 700 having a four longitudinally offset abrasion elements 550 or abrasion elements with an angular offset 550 between the proximal terminal end 554 and the distal terminal end 554 of 90 degrees.

FIG. 7C1 is a distal end view of the balloon treatment device 700 of FIG. 7C at section 1-1 showing the distal terminal end 552 of abrasion element C1 at a 12 o'clock position, the distal terminal end 552 of abrasion element C2 at a 3 o'clock position, the distal terminal end 552 of abrasion element C3 at a 6 o'clock position, the distal terminal end 552 of abrasion element C4 at a 9 o'clock position.

FIG. 7C2 is a proximal end view of the balloon treatment device 700 of FIG. 7C at section 2-2 showing the proximal terminal end 554 of abrasion element C1 at the 3 o'clock position, the proximal terminal end 554 of the abrasion element C2 at the 6 o'clock position, the proximal terminal end 554 of abrasion element C3 at the 9 o'clock position, the proximal terminal end 554 of the abrasion element C4 at the 12 o'clock position.

Figure 8A:
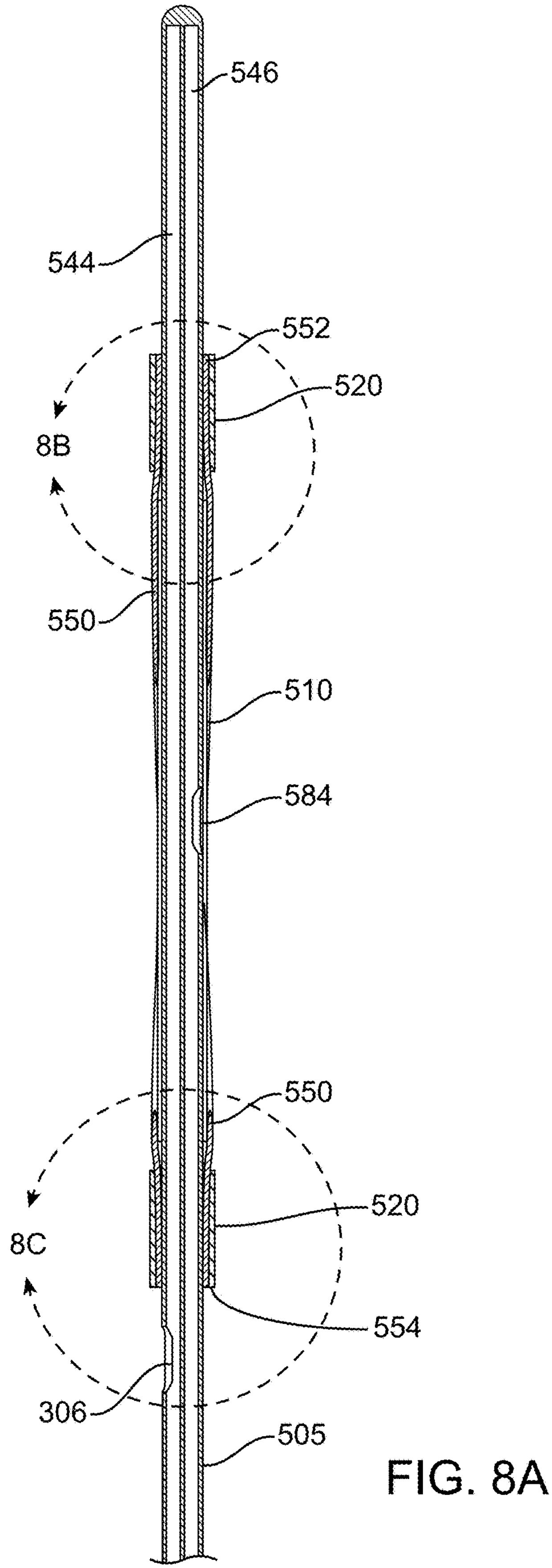
FIG. 8A is a cross-section view of the vein treatment device in FIG. 7C showing the inflation and aspiration ports along with connections for the abrasion elements and balloon to the catheter shaft.
Figure 11A:
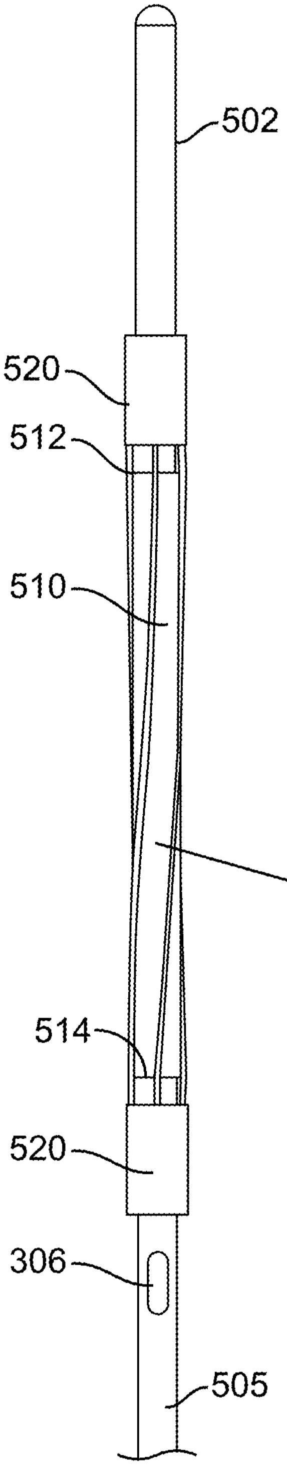
FIG. 11A is a top view of an embodiment of a vein treatment device having four angular offset mechanical abrasion elements arranged about a single balloon.

FIG. 8A is a cross-section view of the vein treatment device 700 in FIG. 7C or 11A showing the inflation port 584 within balloon 510 and the aspiration/injection port 306 through the sidewall of shaft 505. FIG. 8A includes enlarged view sections 8B and 8C.

Figure 8B:
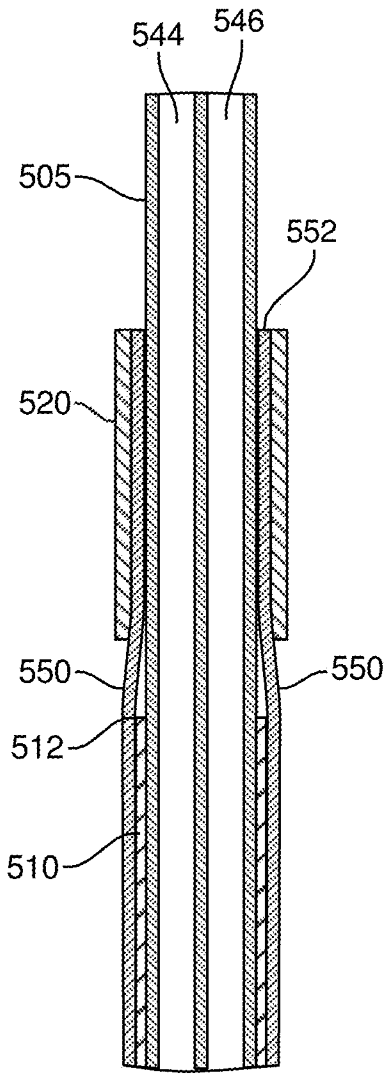
FIG. 8B is an enlarged view of the distal portion of the treatment device of FIG. 8A showing the detail of the angular offset abrasion element attachment to the catheter.
Figure 8C:
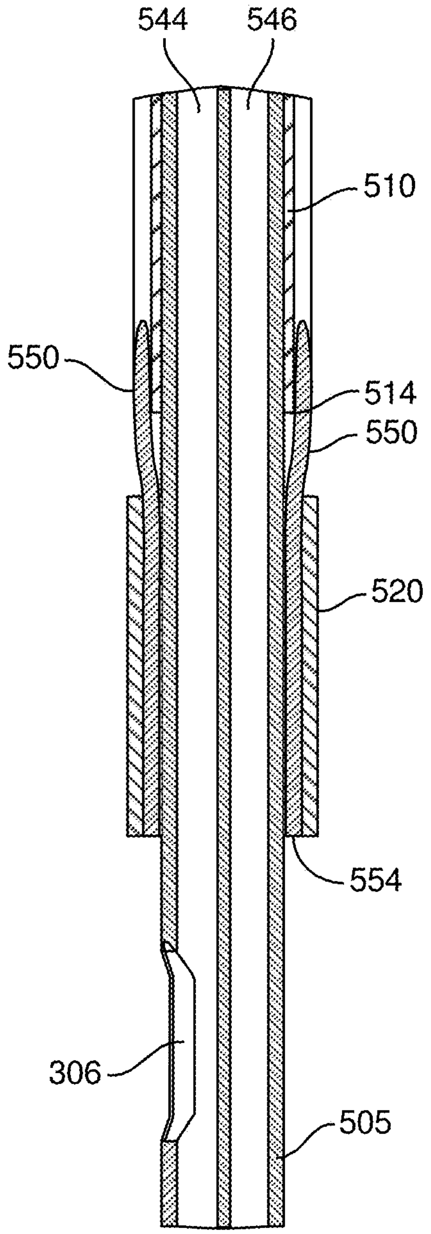
FIG. 8C is an enlarged view of the proximal portion of the treatment device of FIG. 8A showing the detail of the abrasion element attachment point to the catheter and its relation to the aspiration port.

FIG. 8B is an enlarged view of the distal portion of the treatment device 700 of FIG. 8A. This view along with that of FIG. 8C provides detail of the angular offset abrasion element 550 attachment point 520 to the catheter shaft 505. The distal terminal end 552 of the abrasion element 550 is shown in alignment with the edge of the heat shrink segment 520 for clarity of explanation. In other embodiments and as detailed above the terminal ends 552, 554 may be spaced back from the edge of the heat shrink or bonding segment 520 so that there is provided a smooth transition from the terminal ends of the abrasion element and the shaft 505. The terminal ends may be spaced from the edge of the heat shrink cover 520 by 1 mm, 2 mm, 3 mm, 4 mm, 5 mm, 6 mm or 7 mm or more depending on the desired level of transition, the diameter of a wire or coil used in an abrasion element, the shape of the terminal end (See FIGS. 16A1-16D2) and other factors. The fluid lumen 544 and the inflation lumen 546 are also shown in this view.

FIG. 8C is an enlarged view of the proximal portion of the treatment device 700 of FIG. 8A showing the detail of the angular offset abrasion element 550 attachment segment 520 to the catheter and its relation to the aspiration port 306. The spacing between the aspiration port and the edge of the heat shrink segment 520 or proximal terminal end 554 can vary depending on the embodiment but the spacing may be minimized so that in use the aspiration/injection port 306 is close to the proximal end of the balloon so that in use the aspiration of the closure zone is a close as practical to the distal end of the closure zone while occlusion volume is maintained. (See FIGS. 26-30 at steps 2630, 2635 and 2640 as related along with FIGS. 31D and 31E.

FIGS. 8B and 8C also show the relationship between the distal end 512 and the proximal end 514 of the balloon 510 relative to the placement of the terminal ends 552, 554 of an abrasion element 550. FIGS. 8B and 8C illustrate the portion of the balloon 510 that is bonded to the shaft 505. As best seen in FIGS. 14B and 15B as well as 39A, the overall balloon length is divided into the active section used for inflation and the sections on either side of the action section used to bond the balloon to the shaft 505 over the inflation port 584. By way of example and not limitation, a representative balloon may have an overall length of 30 mm with an active length of 13 mm which in use will provide a diameter at an occlusion volume of 12 mm. With an active length of 13 mm, this would leave 17 mm available for bonding the proximal and distal ends of the balloon. This results in an exemplary bonding section lengths of 8 mm and 9 mm. In one embodiment, the proximal and distal terminal ends of the angular offset abrasion elements are bonded to the catheter shaft by bonding or affixing the terminal ends to the bonded portions of the balloon. As such, an exemplary length of angular offset abrasion elements would be comparable to the overall length of the balloon or the length of the balloon with some margin to allow for the length needed to accommodate of the degree of offset. In some embodiments, an additional length of an abrasion element may be included to accomplish the intended terminal end bonding configuration as detailed in FIGS. 16A1-16D2. The advantageous result is that the terminal ends may optionally be fixed to the bonded balloon ends while the portion of the abrasion element between the fixed terminal ends is free to move along with the inflation of the balloon along the active area (see FIGS. 14B and 15B). By way of example in this 30 mm overall length balloon, the overall length of angular offset abrasion elements could be less than 30 mm or 30 mm or 35-40 mm. Any of these representative lengths is substantially shorter that the abrasion elements lengths in the prior art as detailed below.

One chief distinguishing characteristic of the angular offset abrasion elements of the current embodiments and the prior art mechanical abrasion elements is that the use of one or more coil sections provide for an elastic response of the abrasion element to the inflation of the balloon. Instead of accommodating balloon inflation by one or both ends of an abrasion element sliding, the dimensional change of balloon inflation is accommodated by deflection of one or more portions of the coil of an angular offset abrasion element. As mentioned previously, it is also believed that because of the offset orientation along the balloon and the distributed restoring force of the coil portions that the failure modes described above are avoided if not eliminated during normal operation of a balloon therapy device having angular offset abrasion elements.

These benefits of both performance as well as a more compact design are important differences between the various inventive balloon treatment devices described herein and the prior art balloon treatment devices. One limitation of the prior art designs is the abrasion element length and balloon interaction involves terminal end movement. Importantly, fixing the proximal and distal terminal ends of the angular offset abrasion elements results in dramatically smaller balloon treatment devices. Importantly, the moving or translation one or both of the abrasion element terminal ends in the previous designs resulted in abrasion elements with longer overall length compared to those of the angular offset abrasion element designs. Continuing with this example, translating terminal end abrasion elements used with a 30 mm balloon would require a minimum of 30 mm in order to be at least as long as the balloon. Next, there would be an additional length to accommodate translation within a socket or an abrasion element lumen in a sidewall of the catheter. See, for example, FIG. 11B, 11C or 21D-21J of WO Appl. '8045. More specifically, exemplary lengths of abrasion elements in the translating end design, can comprise a length of about 100-200 mm (or about 110-190 mm, or about 120-170 mm, or about 130-160 mm, or about 135-165 mm, or about 140-160 mm, or about 150 mm, etc.). In some embodiments, a length of the mechanical abrasion element is about 90 mm (or about 85-95 mm, 80-100 mm, etc.). Still further, when sidewall abrasion element lumens are employed, additional length is added. The WO Appl. '8045 details that the mechanical abrasion element can extend within the mechanical abrasion element proximal to the proximal mechanical abrasion element aperture to allow for a portion of the mechanical abrasion element to move out of the mechanical abrasion element lumen as the balloon expands and moves the mechanical abrasion element radially outwardly from the catheter shaft. In some embodiments, the mechanical abrasion element extends about 30 mm proximal to the mechanical abrasion element aperture within the mechanical abrasion element lumen. Other lengths are also contemplated (e.g., about 25-35 mm, 20-40 mm, 15-45 mm, 20-40 mm, 25-40 mm, 25-50 mm, etc.). As a result, the moving end design must accommodate not only for the overall length of the balloon but also the spacing to the aperture and still an additional length to allow for movement within the aperture.

Figure 9:
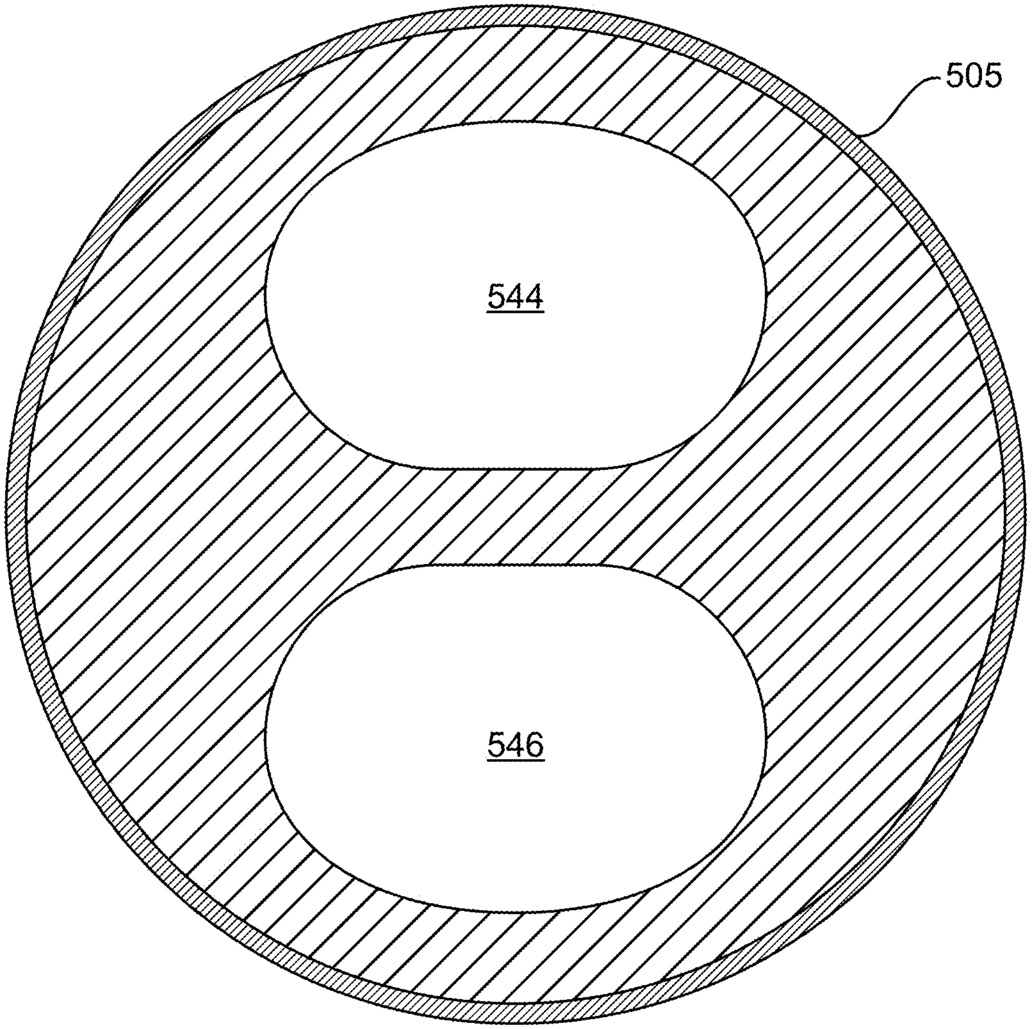
FIG. 9 is a cross-section view of the catheter in FIG. 8A along section 9-9 showing the relative position and size of the balloon inflation and the aspiration/injection lumens.

FIG. 9 is a cross section view 9-9 of the catheter 700 of FIG. 8A showing the relative position and size of the balloon inflation lumen 546 and the aspiration/injection lumen 544. Advantageously, since the terminal ends of the abrasion elements are affixed directly to the shaft or balloon, there is no need to accommodate the additional size of an external sleeve or catheter shaft sidewall lumen (See for example FIGS. 8A, 8B, 11B, 11C and 21D-21K of WO Appl. '8045). As a result, the interior of the catheter shaft may be used for the respective lumens (see also the views of FIGS. 8A and 8B). One benefit is that the size of the catheter may be reduced and a conventional two lumen catheter may be used as shaft 505. This simplifies manufacturing, increases reliability and plays a role in providing balloon therapy devices readily within 4 Fr, 5 Fr, 6 Fr or other sizes.

Figures 10A, 10B, 10C, 10D, 10E, 10F, 10G, 10H, 10I, 10J, 10K:
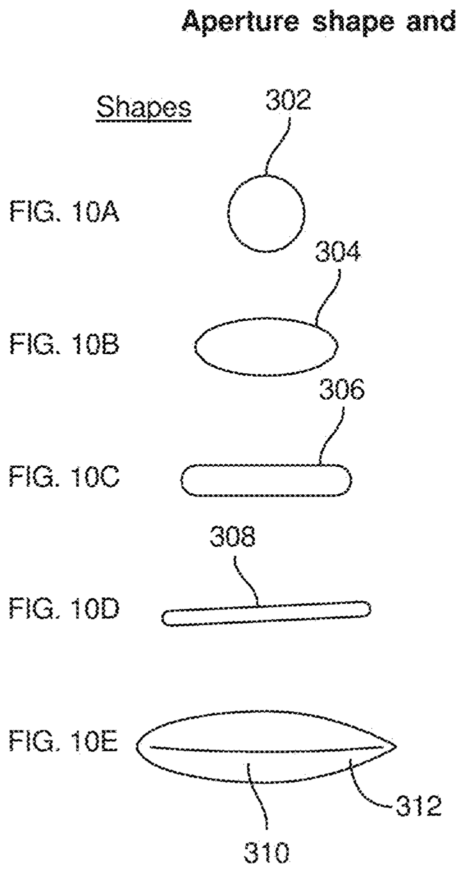
FIGS. 10(*a*)-10(*k*) illustrate different shape, size and arrangement for various embodiments of an aspiration and injection port.

FIGS. 10(*a*)-10(*k*) illustrate different shape, size and arrangement for various embodiments of an aspiration and injection port. FIGS. 10(*a*)-10(*k*) illustrate various alternative aperture shapes, arrangements and circumferential positions. Alternative shapes of aperture 110 include a circle 302 (FIG. 10(*a*)), an oval 304 (FIG. 10(*b*)), a rounded rectangle 306 (e.g., rectangle with rounded corners) (FIG. 10(*c*)), a narrow slot 308 (FIG. 10(*d*)), a slit 310 in the covering 312, etc). It is to be appreciated that the aperture viewed in cross section may have walls that are the same diameter at the inner surface of the lumen and the outer surface of the catheter. Optionally, the width of the aperture at the inner surface of the lumen may be smaller than the width of the aperture at the outer surface of the catheter. In another alternative, the width of the aperture at the outer surface of the catheter may be smaller than the width of the aperture at the inner surface of the lumen.

FIGS. 10(*f*)-10(*h*) show additional variations 314, 316, 318 of the multiple holes or apertures along the length for delivery and aspiration. As shown in FIG. 10(*f*), there can be multiple rows of the same type of aperture. In some embodiments, there can be a diamond pattern of the same type of aperture, as shown in FIG. 10(*g*). In some embodiments, as shown in FIG. 10(*h*), there can be a combination of different types of apertures.

Optionally or additionally, one or more apertures 110 may be provided with multiple holes that could be arranged around the perimeter. FIGS. 10(*i*)-10(*k*) show different embodiments of circumferential positioning of multiple holes. As shown in FIG. 10(*i*), there may be a single hole 330 around the circumference of the catheter shaft. In some embodiments, as shown in FIG. 10(*j*), there may be two holes 332 positioned around the circumference of the catheter shaft (e.g., generally equally spaced around the circumference of the catheter shaft). In some embodiments, as shown in FIG. 10(*k*), there can be more than two holes 334 (e.g., four holes) positioned around the circumference of the catheter shaft (e.g., generally equally spaced around the circumference of the catheter shaft. Other configurations are also contemplated. There could also be only a single hole used for both aspiration and injection. The aspiration and injection holes may be provided in any combination of the above in any combination of FIGS. 10(*a*)-10(*k*). In one exemplary embodiment, proven out by experimentation, there is a single aspiration and injection port 306 having an overall shape as in FIG. 10(*c*) with an overall length of 2.25 mm and a width of 0.68 mm. A dual-purpose single aspiration and injection port having these dimensions is optimized both for (a) injection of foam based agents or physician compounded foam so as to maintain the foam composition and (b) aspiration of fluids within a treated vessel while reducing the risk of sucking in a portion of the vessel sidewall and occluding the port 306.

FIG. 11A is a top view of an embodiment of a balloon treatment device 700 having four mechanical abrasion elements 550 arranged about a single balloon 510 as in FIG. 7C. In this representative embodiment, the width of the catheter 505 is 2 mm, the length of heat shrink segment 520 is 4 mm with a spacing of 1-3 mm between the balloon ends 512, 514 and the adjacent edges of the heat shrink segment 520. The spacing between the proximal balloon end 514 and the distal most portion of the aspiration/injection aperture 306 is 6.36 mm. The overall length of the balloon 510 between ends 512, 514 is 22 mm. In one embodiment, the balloon 510 has an active length of between 10 mm to 14 mm.

Figure 11B:
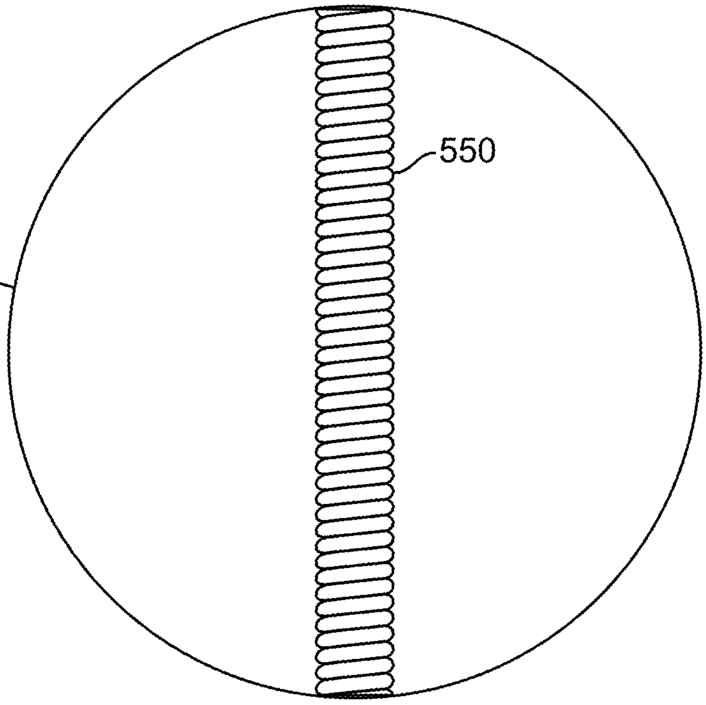
FIG. 11B is an enlarged view of an abrasion element having a coil segment on one of the mechanical abrasion elements shown in FIG. 11A.

FIG. 11B is an enlarged view of a coiled segment 1305 on one of the mechanical abrasion elements 550 shown in FIG. 11A. The coiled may be formed from a biocompatible metal such as stainless steel or other material based on the desired elastic properties of the resulting abrasion element. The wire dimensions, shape, coil dimensions and pitch may be varied to provide a wide range of different types of abrasion elements with difference response characteristics.

Figure 12A:
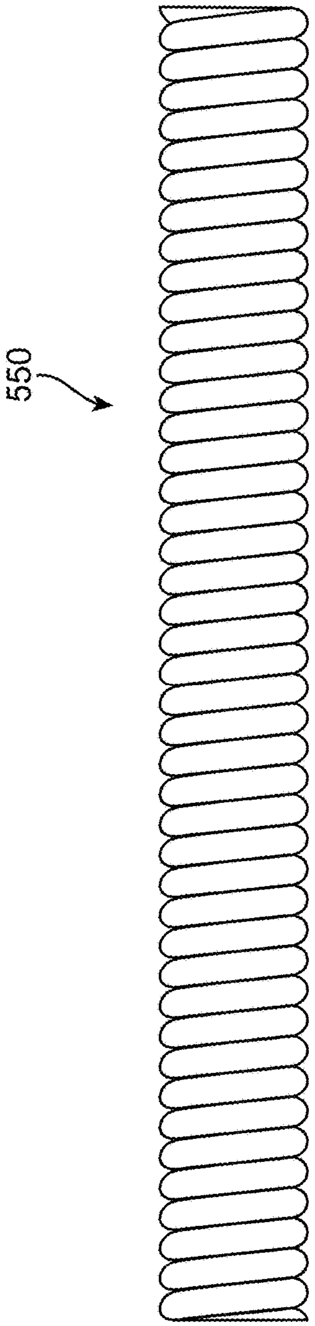
FIG. 12A is an enlarged portion of an exemplary coil structure as shown and described herein.

FIG. 12A is an enlarged portion of an abrasion element 550 with an exemplary coil structure 1305 of FIG. 11B as shown and described herein. The overall length of the coiled abrasion element may be 35 mm. Longer or shorter abrasion elements may be used depending on the overall length of the balloon and the active length of the balloon as discussed herein. In one specific aspect the abrasion element is formed from stainless steel, in one specific embodiment the material is SS 304V.

Figure 12B:
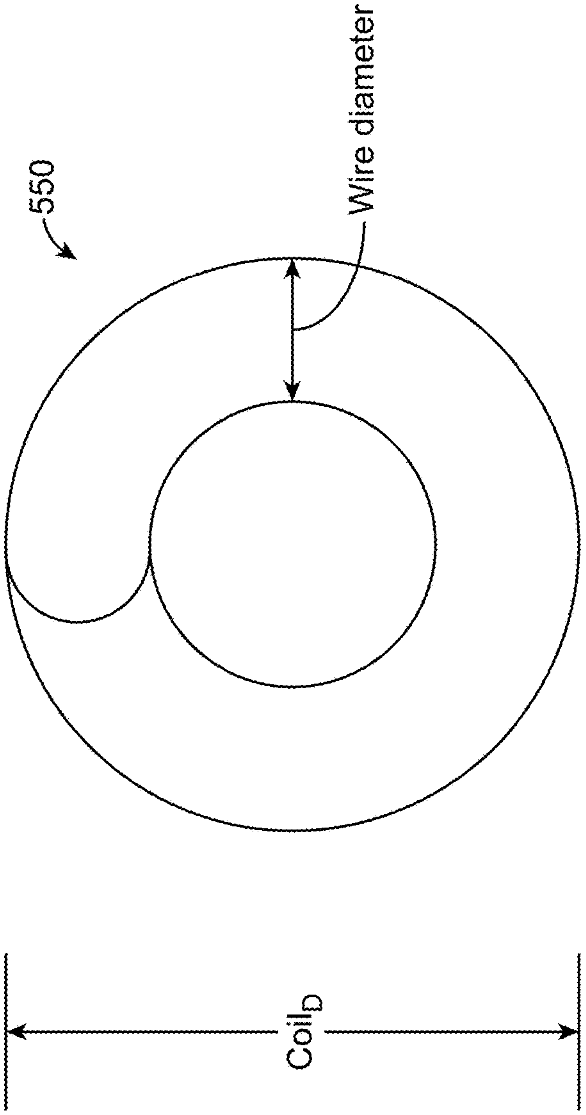
FIG. 12B is a section view of the exemplary coil structure of FIG. 12A showing the wire thickness and the outer diameter of the coil structure.

FIG. 12B is a section view of the exemplary angular offset abrasion element 550 with a coil structure 1305 of FIG. 12A showing the wire thickness and the outer diameter of an exemplary coil structure. In one aspect, the wound coil outer diameter is 0.008 inches and the wire outer diameter that forms is coil is 0.002 inches.

In contrast to the abrasion element embodiments of FIGS. 11A-12B with a single wire/coil combination, the various alternative embodiments of an angular offset abrasion structure are not so limited. In other alternative configurations, an angular offset abrasion element 550 may include one or more coiled segments 1305 adjacent to one or more non-coiled segments 1310.

Figure 13A:
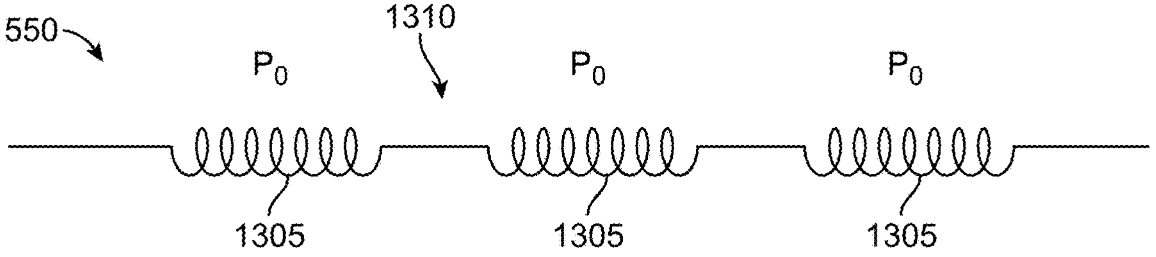
FIG. 13A is a side view of an exemplary hybrid coil abrasion element structure having both coiled and non-coiled segments.

FIG. 13A is a side view of an exemplary hybrid coil abrasion element structure 550 having three coiled segments 1305 of pitch P0 separated by non-coiled segments 1310.

Figure 13B:
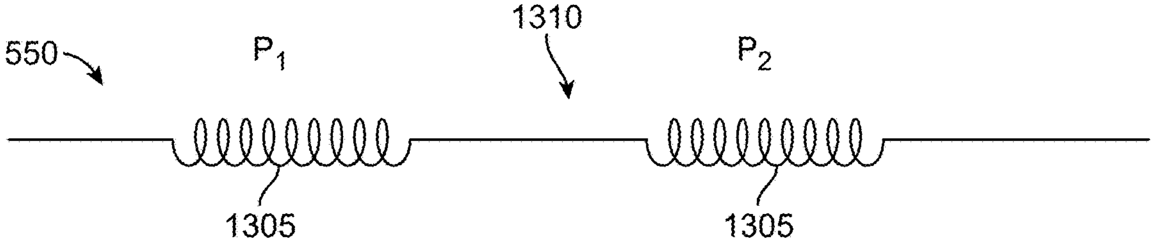
FIG. 13B is a side view of an exemplary hybrid coil abrasion element structure having both coiled and non-coiled segments including different coil pitches.

FIG. 13B is a side view of an exemplary hybrid coil abrasion element structure 550 having two coiled segments 1305 separated by non-coiled segments 1310. In contrast to FIG. 13A, the coiled segments 1305 have different pitches of P1 and P2. It is to be appreciated that the length of coiled and non-coiled segments may be the same or vary along the length of an angular offset abrasion element.

Figure 13C:
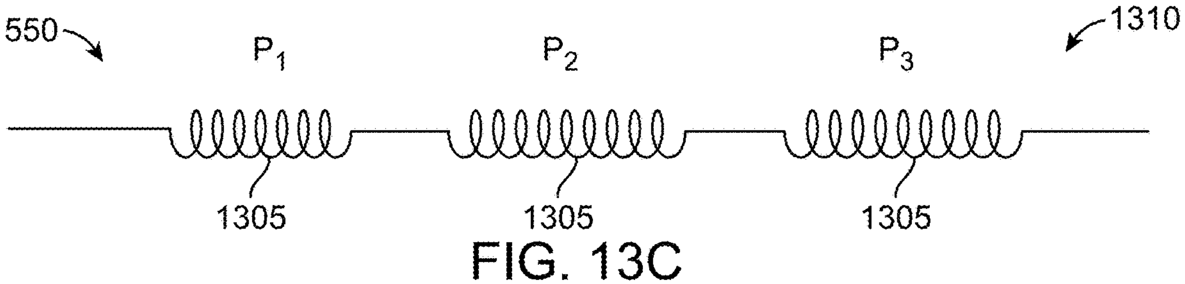
FIG. 13C is a side view of an exemplary hybrid coil abrasion element structure having both coiled and non-coiled segments including different coil pitches.

FIG. 13C is a side view of an exemplary hybrid coil abrasion element structure 550 having both coiled segments 1305 and non-coiled segments 1310. In this example, the length and the pitches of the coiled segments varies. In this illustrative embodiment, the length of the coil segment 1305 of pitch P1 is shorter than the length of the coil segments 1305 of pitches P2 and P3. This embodiment also illustrates that three different coil pitches may be included in a specific angled offset abrasion element 550.

Figure 14A:
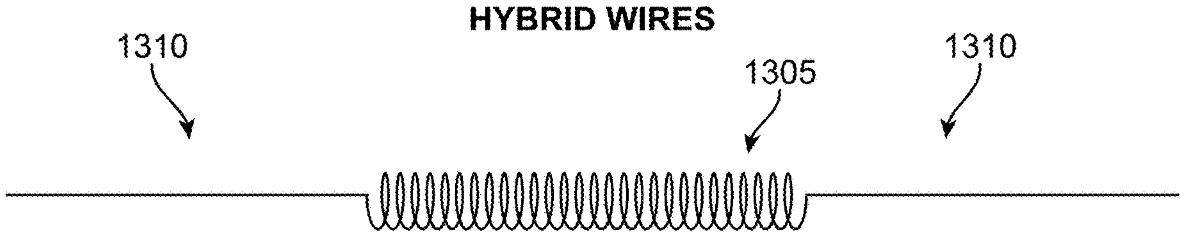
FIG. 14A is a side view of a coil segment with coiled and non-coiled segments that is sized for use along an active segment of an inflated balloon.
Figure 14B:
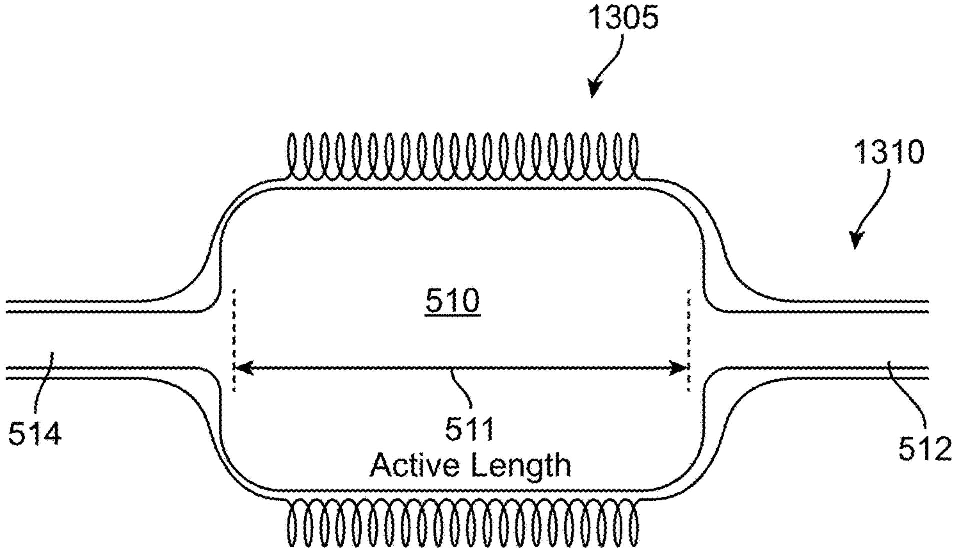
FIG. 14B is a side view of the coil abrasion element of FIG. 14A shown along an active segment of a balloon.

FIG. 14A is a side view of a coil segment with coiled 1305 and non-coiled 1310 segments that is sized for use along an active segment or length 511 of an inflated balloon 510. (For a different inflated balloon shape see FIG. 39A.) FIG. 14B is a side view of the coil abrasion element 550 of FIG. 14A shown along a portion of the active segment or length 511 of a balloon 510. This embodiment would localize the engagement of the coil elements and the vessel wall to be along the main portion of the active length. An abrasion element of this configuration may enable various different segment abrasion areas or the spacing between them along a vessel wall as shown and described in FIG. 32C.

Figure 15A:
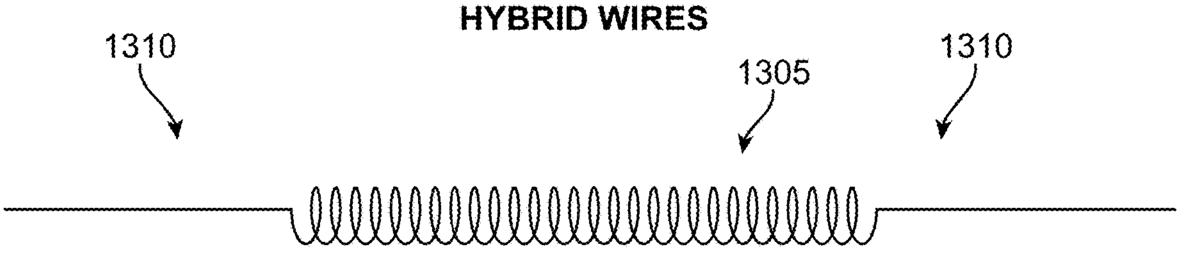
FIG. 15A is a side view of a coil segment with coiled and non-coiled segments that is sized to extend beyond an active segment of an inflated balloon.
Figure 15B:
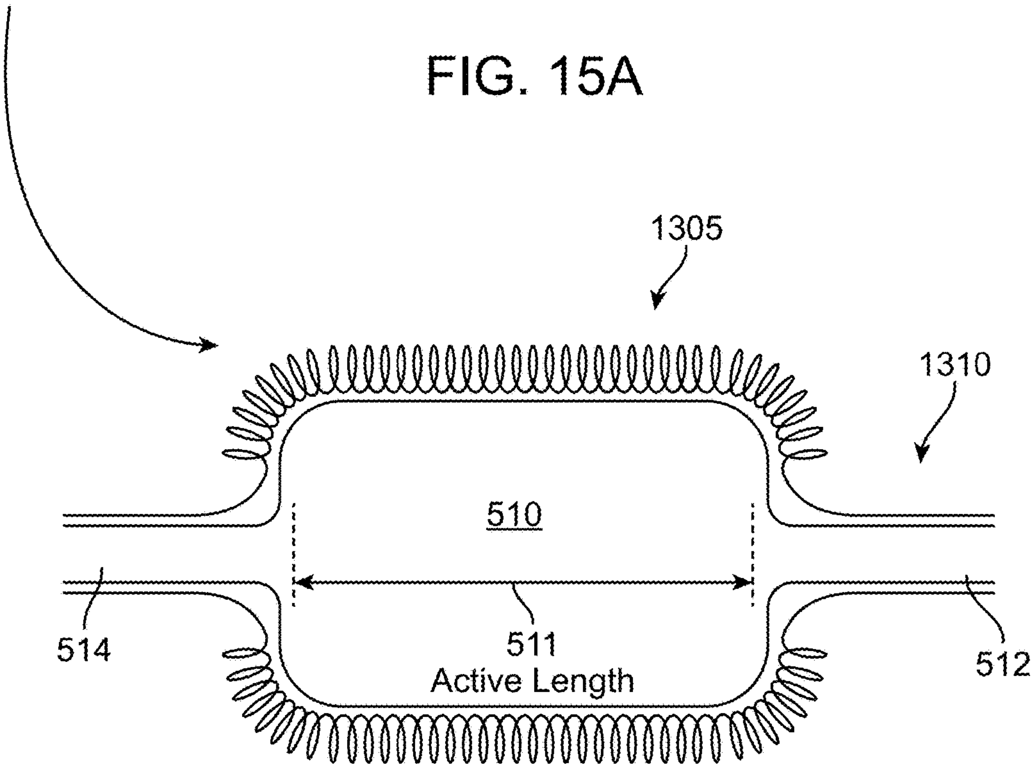
FIG. 15B is a side view of the coil abrasion element of FIG. 15A shown extending beyond the active segment of an inflated balloon.

FIG. 15A is a side view of an angled abrasion element 550 having a hybrid coil—non-coiled segments. In this embodiment, the length of the coiled segment 1305 is longer than that of FIG. 14A. The length of the coiled segment 1305 is sized to extend beyond an active segment 511 of an inflated balloon 510. FIG. 15B is a side view of the angled offset abrasion element 550 of FIG. 15A along an inflated balloon 510. As shown, the coil segment 1305 has a length selected so that the coil elements extend beyond the active segment or length 511 of an inflated balloon 510. The use of a longer coil segment may increase the dimensions of the associated abrasion area to further reduce spacing between adjacent segmented abrasion areas or aid in the creating of continuous or nearly continuous abrasion areas (See FIG. 25C). It is to be appreciated that the various combinations of coiled and non-coiled segments, the length of each, the relative pitches of different coil segments and the position of those abrasion elements along a balloon may be varied and combined in a number of different ways depending upon the desired abrasion area formation and other factors. In still other variations, there may be variations between the characteristics of each angular offset abrasion element employed in a specific balloon treatment device. The wide range of configurations of the angled offset abrasion elements provides considerable control over the amount of abrasion and size of the abrasion areas produced by a specific balloon treatment device configuration.

FIGS. 16A1 and 16A2 are top views of a portion of a terminal end of an angular offset abrasion element 550 of FIGS. 5A, 6B and 7C having a linear portion provided for coupling to an outer wall of the delivery catheter. The linear portion used to couple to the catheter may be an uncoiled wire portion, a coiled portion with a pitch that is the same as the balloon zone or a coiled portion with a pitch that differs from the pitch along the balloon zone. In each of the embodiments of FIGS. 16A1-D1 a portion of the terminal ends 552/554 the abrasion element 550 is secured in the dashed zone to the catheter while the remaining portion is unsecured and free to move with balloon inflation and volume changes. In a similar way in FIGS. 16A2-16D2, a portion of the terminal ends 552/554 in the shaded portion is bonded to the catheter 502 while the remainder (i.e., non-shaded portion between the terminal ends 552/554) is free to move in response to balloon diameter changes along the operational volume of the active length of the balloon.

FIG. 16A1 is a top view of a portion of a terminal end 552/554 of an offset abrasion element 550 of FIGS. 5A1, 5A2, 6B1, 6B2, 7C1, 7C2 having a linear portion provided for coupling to an outer wall of the delivery catheter beneath a heat shrink segment 520. The linear portion used to couple to the catheter may be an uncoiled wire portion, a coiled portion with a pitch that is the same as the balloon zone or a coiled portion with a pitch that differs from the pitch along the balloon zone.

FIG. 16A2 is a top view of a portion of a terminal end 552/554 of a mechanical abrasion element of FIGS. 5A1, 5A2, 6B1, 6B2, 7C1, 7C2 having a linear portion provided for coupling to an outer wall of the delivery catheter using any suitable fixation technique or optionally in combination with a heat shrink segment 520. The linear portion used to couple to the catheter may be an uncoiled wire portion, a coiled portion with a pitch that is the same as the balloon zone or a coiled portion with a pitch that differs from the pitch along the balloon zone.

FIGS. 16B1 and 16B2 are top-down views of a portion of a terminal end 552/554 of an offset abrasion element 550 of FIGS. 5A, 6B and 7C having a simple curved portion provided for coupling to an outer wall of the delivery catheter. The simple curved portion used to couple to the catheter may be an uncoiled wire portion, a coiled portion with a pitch that is the same as the balloon zone or a coiled portion with a pitch that differs from the pitch along the balloon zone.

FIG. 16B1 is a top view of a portion of a terminal end 552/554 of a mechanical abrasion element 550 of FIGS. 5A1, 5A2, 6B1, 6B2, 7C1, 7C2 having a simple curved portion provided for coupling to an outer wall of the delivery catheter beneath a heat shrink segment. The simple curved portion used to couple to the catheter may be an uncoiled wire portion, a coiled portion with a pitch that is the same as the balloon zone or a coiled portion with a pitch that differs from the pitch along the balloon zone.

FIG. 16B2 is a top view of a portion of a terminal end 552/554 of an angular offset mechanical abrasion element 550 of FIGS. 5A1, 5A2, 6B1, 6B2, 7C1, 7C2 having a simple curved portion provided for coupling to an outer wall of the delivery catheter using any suitable fixation technique or optionally in combination with a heat shrink segment 520. The simple curved portion used to couple to the catheter may be an uncoiled wire portion, a coiled portion with a pitch that is the same as the balloon zone or a coiled portion with a pitch that differs from the pitch along the balloon zone.

FIGS. 16C1 and 16C2 are top down views of a portion of a terminal end 552/554 of an angular offset abrasion element 550 of FIGS. 5A, 6B and 7C having a coiled portion provided for coupling to an outer wall of the delivery catheter. The coiled portion used to couple to the catheter may be an uncoiled wire portion, a coiled portion with a pitch that is the same as the balloon zone or a coiled portion with a pitch that differs from the pitch along the balloon zone.

FIG. 16C1 is a top view of a portion of a terminal end 552/554 of a mechanical abrasion element 500 of FIGS. 5A1, 5A2, 6B1, 6B2, 7C1, 7C2 having a coiled portion provided for coupling to an outer wall of the delivery catheter beneath a heat shrink segment. The coiled portion used to couple to the catheter may be an uncoiled wire portion, a coiled portion with a pitch that is the same as the balloon zone or a coiled portion with a pitch that differs from the pitch along the balloon zone.

FIG. 16C2 is a top view of a portion of a terminal end 552/554 of a mechanical abrasion element of FIGS. 5A1, 5A2, 6B1, 6B2, 7C1, 7C2 having a coiled portion provided for coupling to an outer wall of the delivery catheter using any suitable fixation technique or optionally in combination with a heat shrink segment. The coiled portion used to couple to the catheter may be an uncoiled wire portion, a coiled portion with a pitch that is the same as the balloon zone or a coiled portion with a pitch that differs from the pitch along the balloon zone.

FIGS. 16D1 and 16D2 are top-down views of a portion of a terminal end 554/552 of an angular offset abrasion element 550 of FIGS. 5A, 6B and 7C having a complex curved portion provided for coupling to an outer wall of the delivery catheter. The complex curved portion used to couple to the catheter may be an uncoiled wire portion, a coiled portion with a pitch that is the same as the balloon zone or a coiled portion with a pitch that differs from the pitch along the balloon zone.

FIG. 16D1 is a top view of a portion of a terminal end 552/554 of a mechanical abrasion element 500 of FIGS. 5A1, 5A2, 6B1, 6B2, 7C1, 7C2 having a complex curved portion provided for coupling to an outer wall of the delivery catheter beneath a heat shrink portion 520. The complex curved portion used to couple to the catheter may be an uncoiled wire portion, a coiled portion with a pitch that is the same as the balloon zone or a coiled portion with a pitch that differs from the pitch along the balloon zone.

FIG. 16D2 is a top view of a portion of a terminal end 552/554 of a mechanical abrasion element 550 of FIGS. 5A1, 5A2, 6B1, 6B2, 7C1, 7C2 having a complex curved portion provided for coupling to an outer wall of the delivery catheter using any suitable fixation technique or optionally in combination with a heat shrink segment 520. The complex curved portion used to couple to the catheter may be an uncoiled wire portion, a coiled portion with a pitch that is the same as the balloon zone or a coiled portion with a pitch that differs from the pitch along the balloon zone.

Figure 17:
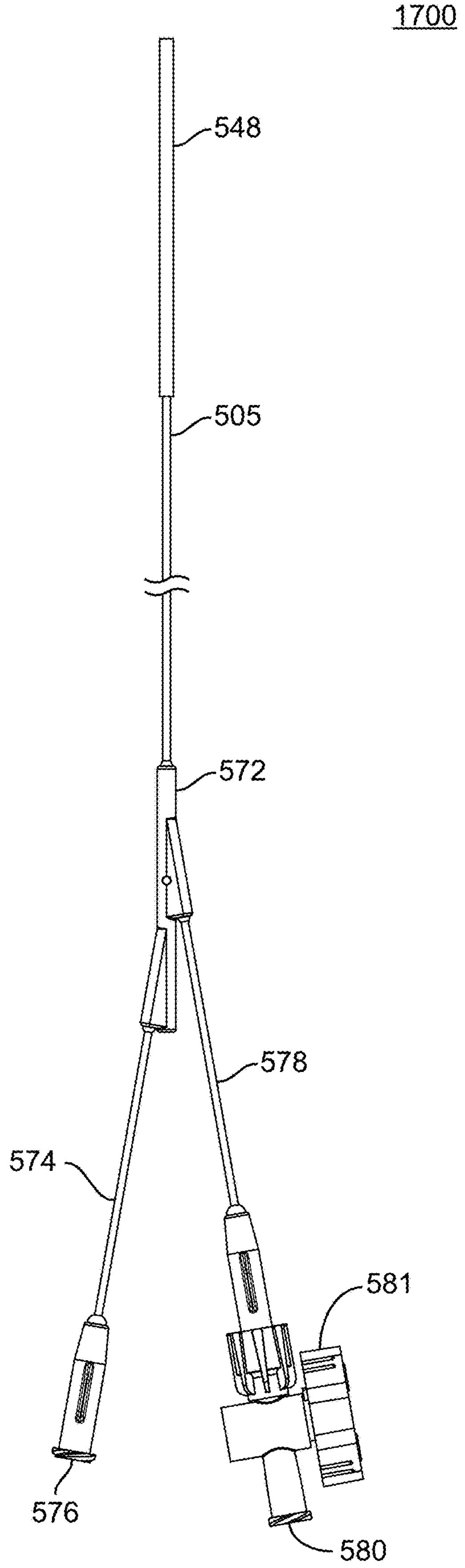
FIG. 17 is a top-down view of a balloon-based therapy system having a hub, inflation port and aspiration/infection port and a peel away cover on over the distal end covering the balloon treatment device.
Figure 18:
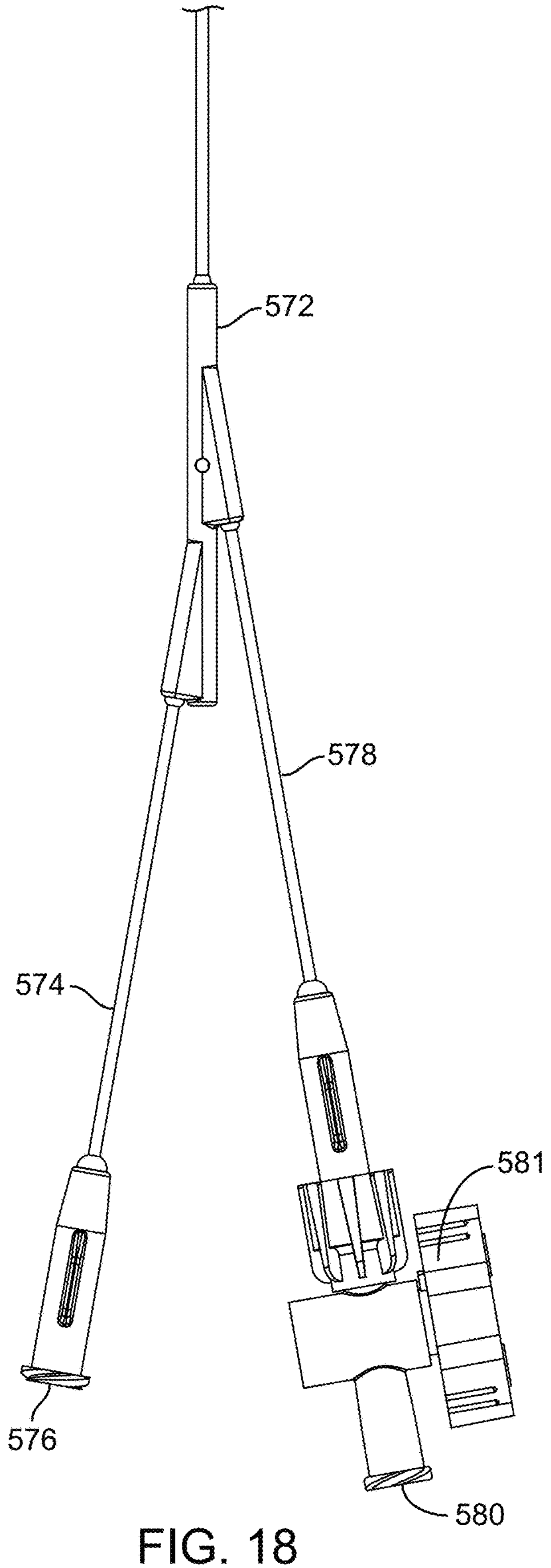
FIG. 18 is an enlarged view of the hub of the system shown in FIG. 17.
Figure 19:
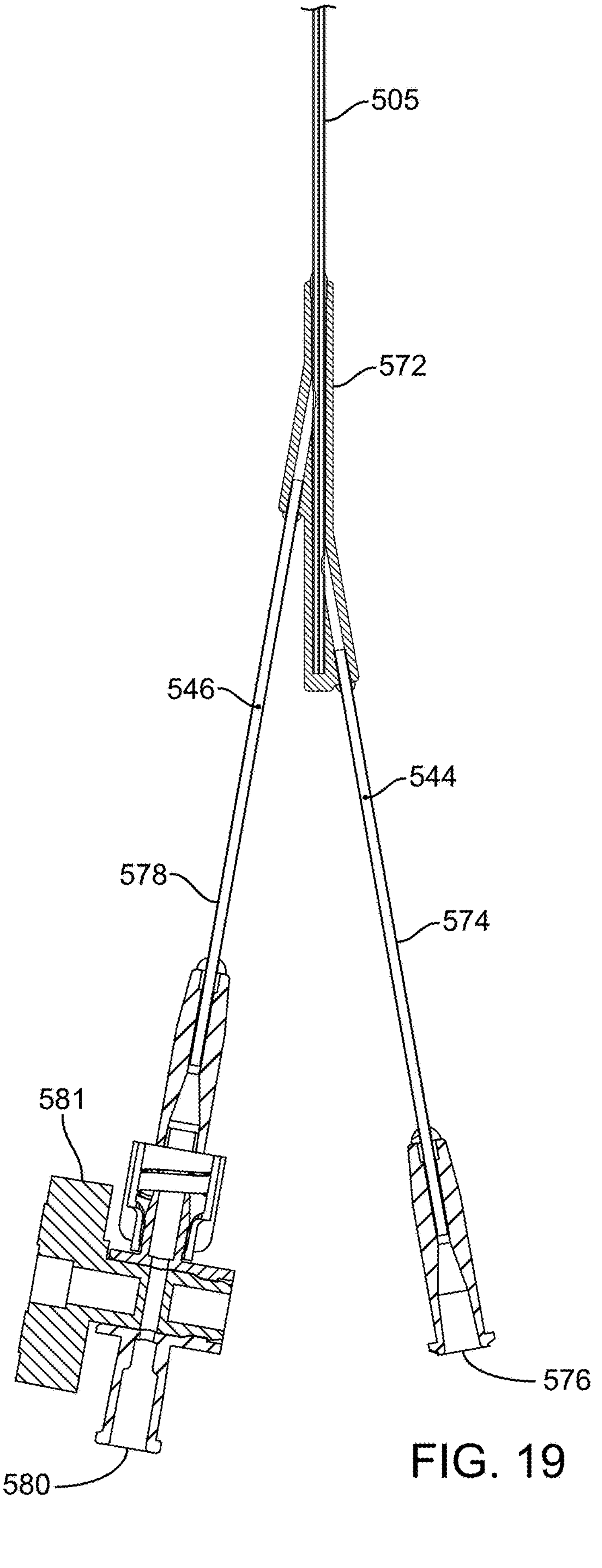
FIG. 19 is a cross-section view of the system of FIG. 18.

FIG. 17 is a top-down view of a balloon-based therapy system 1700 such as used with the balloon therapy devices 500, 600 or 700. The balloon-based therapy system 1700 has a hub 572, inflation port 580 and aspiration/inflation or fluid port 576. In this view there is also shown a peel away cover 548 on over the distal end covering the balloon treatment device. The peel away cover aids in long term storage and pre-use handling of the balloon therapy devices so that the angular offset abrasion elements and balloon are not damaged. Extending proximally from the connector hub 572 is a tube 574 connecting to a fluid port 576. This port 576 can be used, for example, for infusion of a closure agent or other treatment substance as described herein or suited to the desired vessel treatment protocol. The port 576 and the interior of the tube 574 are in communication with the fluid lumen 544 within shaft 505 and with aspiration and injection port or aperture 306. The port 576 is initially used to aspirate fluid from within a vessel after formation of a closure zone in the vessel. (See methods in FIGS. 26-30). Thereafter, the port 576 is used to infuse a closure agent into the closure zone. In some embodiments, the port 576 comprises a Luer style connector or any other suitable connector. Also extending proximally from the connector hub 572 is a tube 578 connecting to an inflation port 580. The port 580 can also comprise a Luer style connector or any other suitable medical connector. In some embodiments, the port 580 comprises a locking valve 581 to seal the inflation port at a desired inflation level of the balloon. The locking valve 581 may be used to hold the inflation volume for the partial mechanical engagement volume, vasospasm volume, a volume selected to transition one or more angular offset abrasion elements out of a stowed condition into a position to engage an inner wall of a treatment vessel, a volume to transition one or more angular offset abrasion elements into a partially deployed configuration or a volume wherein a portion of the one or more angular offset abrasion elements makes venous wall contact. This initial engagement volume is maintained during the formation of abrasion areas along the closure zone such as, for example, continuous abrasion areas, substantially continuous abrasion areas or segmented abrasion areas as shown and described in FIGS. 23, 24B, 25C, 32C and 34. For additional details of the use of the inflation port see FIGS. 26-30 as well as, for example, the details of steps 2615, 2715, 2815, 2915 and 3015. In addition, the inflation port 580 and locking valve 581 may be used to create and maintain an occlusion volume after the formation of a closure FIG. 18 is an enlarged view of the hub and components of the system shown in FIG. 17. FIG. 19 is a cross-section view of the system of FIG. 18. This view illustrates the relationship between the fluid lumen 544, the tube 574 and fluid hub 576. This view also illustrates the relationship between the inflation lumen 546 to the inflation tube 578 the control valve or locking valve 581 and the inflation port 580.

Figure 20:
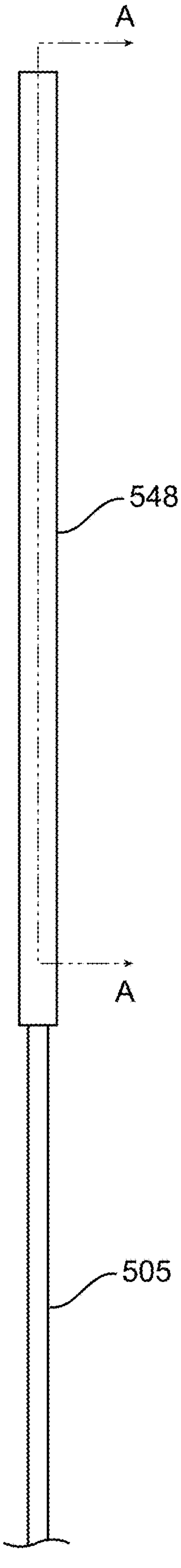
FIG. 20 is an enlarged view of the distal end of the therapy system of FIG. 17 indicating section A-A.

FIG. 20 is an enlarged view of the distal end of the therapy system of FIG. 17 indicating section A-A.

Figure 21:
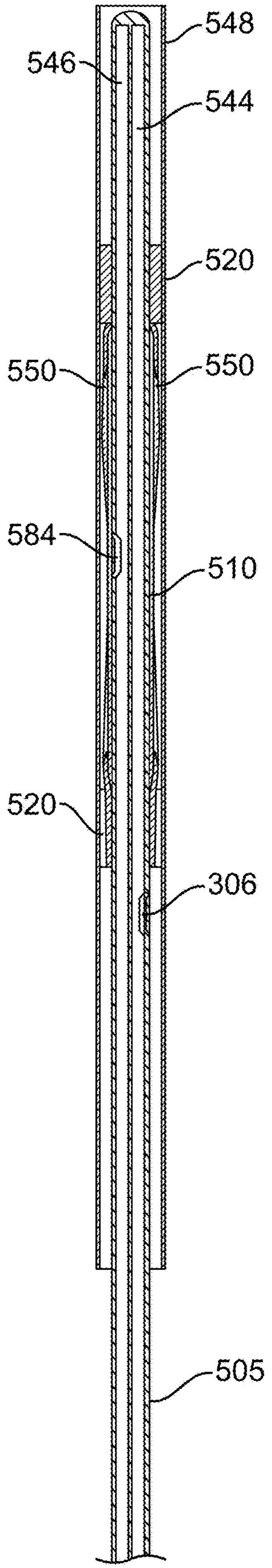
FIG. 21 is a cross-section view along section A-A of FIG. 20.

FIG. 21 is a cross-section view along section A-A of FIG. 20 representing the details of the balloon treatment device within the peel away cover 548. This view shows the arrangement of the components of the views of FIGS. 8A, 8B and 8C in relation to the peel away cover 548.

Figure 35A:
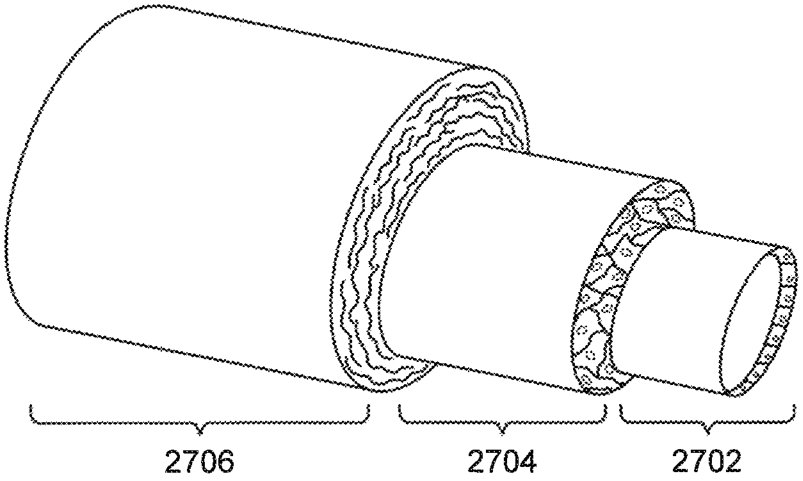
FIGS. 35A and 35B show exemplary venous wall anatomy.
Figure 35B:
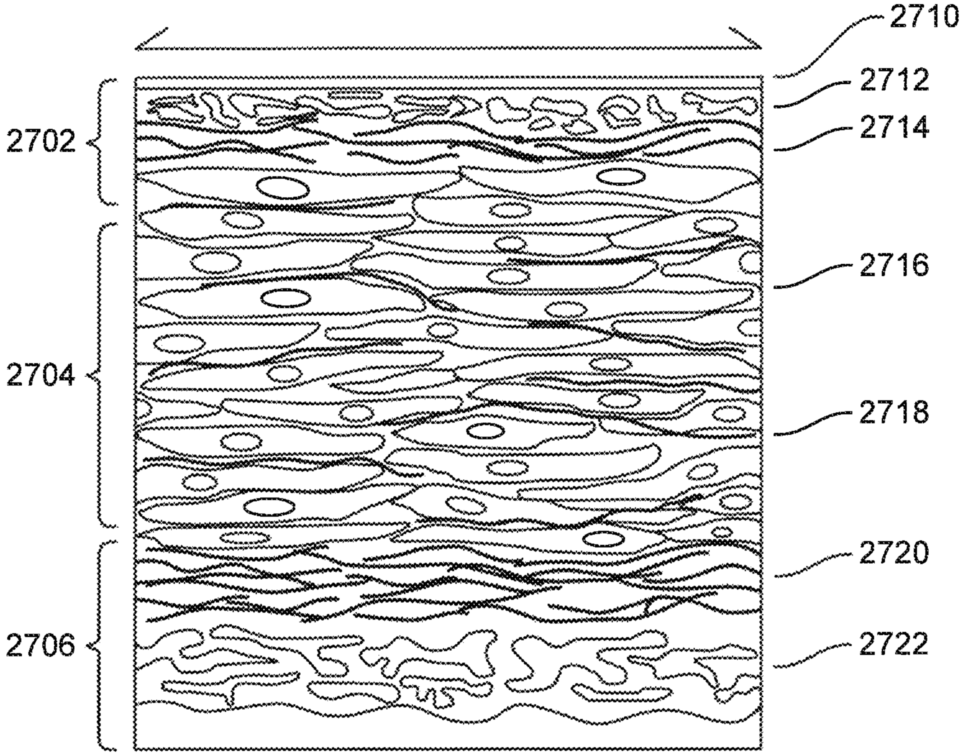

Having described a variety of the balloon-based treatment devices with a plurality of different angular offset abrasion elements, we turn now to a discussion of the vein anatomy and various disease states and vein treatment locations. FIGS. 35A and 35B illustrate the anatomy of a vein. As shown in FIG. 35A, the vein wall comprises an inner layer, the tunica intima 2702, an intermediate layer, the tunica media 2704, and the outer layer, the tunica adventitia 2706. Moving to FIG. 35B, the tunica intima comprises the endothelium 2710, connective tissue 2712, and internal elastic membrane 2714. The tunica media comprises muscle fibers 2716, elastic fiber 2718. The tunica adventitia comprises an external elastic membrane 2720 and connective tissue 2722.

Advancing the at least partially inflated balloon through the closure zone does not perforate the vein and only causes minimal injury to the vein. In most embodiments, the combination of compliant balloon inflation and mechanical abrasion element engagement is optimized to result in only a very limited amount of damage to the vein wall, mostly nearly limited to the removal of all, most or some of the cells in the endothelial layer of the vein within the closure zone. The level of engagement produced by embodiments of the present invention stand in stark contrast to the more aggressive tissue engagement elements coupled to non-compliant balloons operating at high pressures usually above 1 atm. While desiring not to be bound by theory, it is believed that the various compliant or semi-compliant balloon treatment device embodiments described herein would be unable to address the clinical conditions anticipated by conventional non-compliant balloon therapy systems that are adapted and configured for deployment of vascular stents, engagement of an occluded or partially occluded vessel walls for the purpose of restoring vascularization by mechanical interactions with sufficient force and engagement to result in breaking, cutting or cracking calcified lesions causing the partial or complete occlusion. Because of the different operational requirements of the inventive elastomeric balloon embodiments herein, materials such as polyurethane or silicone or other materials that allow the inflation volumes described herein during mechanical abrasion element engagement as well as vein occlusion steps. In some configurations, the balloon may be expanded from 100% to up to 800% which is particularly useful given the variation in vein diameter that may be encountered within a closure zone or to achieve vessel occlusion given the elasticity of a vein wall. In one exemplary embodiment, a balloon with a working length of 13 mm may be inflated to a 12 mm working diameter within a vessel. These and other design features of the various embodiments described herein stand in direct contrast to semi-compliant or mid-pressure balloon therapy systems and non-compliant or high-pressure balloon therapy systems. Semi-compliant (mid-pressure) balloons are commonly made of Pebax or higher durometer polyurethanes to still deliver much higher pressure than compliant balloons but with some degree of compliance that is not provided by the non-compliant balloon systems. Non-compliant (high-pressure) balloons are commonly made from polyester or nylon and are used in balloon treatment systems to expand to a specific, predefined diameter and exert high pressure when deployed.

As described herein, advancing the at least partially inflated balloon through the closure zone causes endothelial damage. In some embodiments, the degree of endothelial injury is a portion of the endothelium, for example, about half of the endothelial cells are lost. Other degrees of endothelial injury are also possible (e.g., ¼ of the endothelial cells are lost, ¾ of the endothelial cells are lost, etc.).

In some embodiments, the injury caused by the balloon therapy device is limited to the tunica intima. In some embodiments, the injury caused by the balloon therapy device is limited to the endothelium. In some embodiments, the injury caused by the balloon therapy device is limited to the endothelium and the connective tissue of the tunica intima. Other depths of injury are also contemplated.

In various embodiments, the balloon therapy device may be used for instillation of various medications into the isolated segment of vessel (i.e., sclerosant, chemotherapeutic agent, stem cells). The sclerosant may include sodium tetradecyl sulfate, polidocanol, or ethanolamine oleate, in some embodiments.

Figure 36:
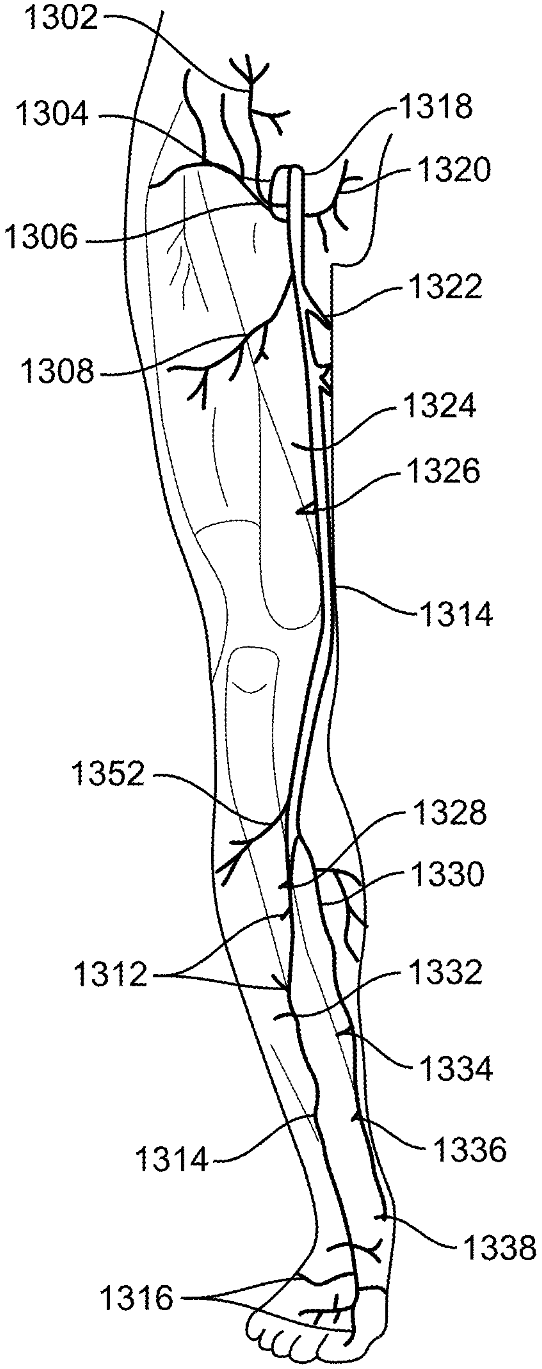
FIGS. 36 and 37 illustrate exemplary venous vasculature in the lower limbs and pelvis that may be targeted for treatment using the devices and methods described herein.
Figure 37:
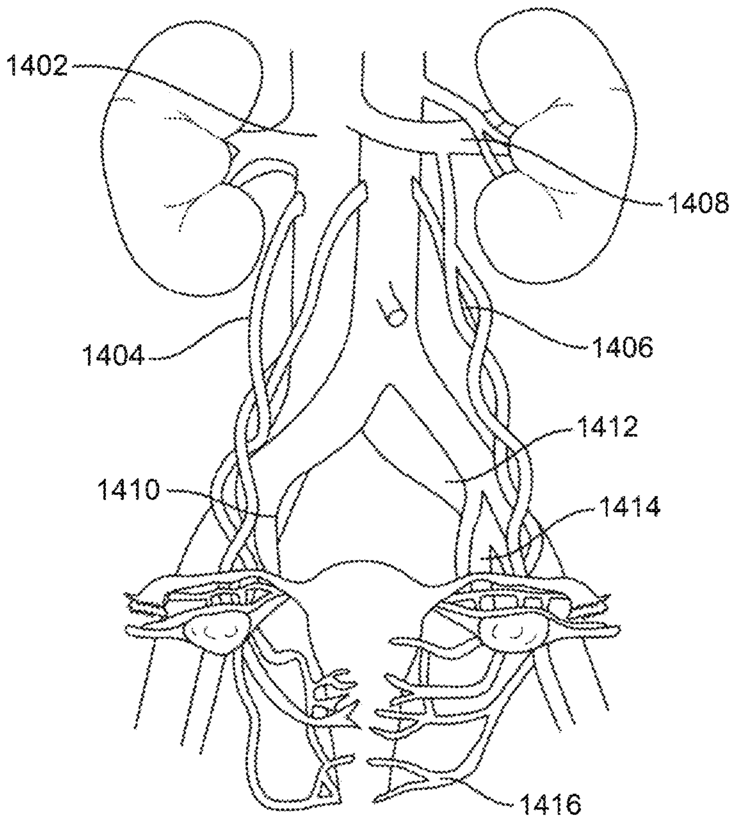

FIGS. 36 and 37 illustrate exemplary venous vasculature in the lower limbs and pelvis that may be targeted for treatment using the devices and methods described herein. FIG. 36 shows the superficial epigastric vein 1302, the common femoral artery 1304, the superior circumflex iliac vein 1306, the lateral accessory saphenous vein 1308, the anterior tributary of the greater saphenous vein 1352, the proximal paratibial perforators 1312, the greater saphenous vein 1314, the medial perforators of the foot 1316, the common femoral vein 1318, the superficial external pudendal vein 1320, the medial accessory saphenous vein 1322, the Hunter's perforator 1324, the Dodd's perforator 1326, the Boyd's perforator 1328, the posterior arch vein 1330, the 24 cm perforator 1332, the Cockett III perforator 1334, the Cockett II perforator 1336, and the Cockett I perforator 1338.

FIG. 37 shows the inferior vena cava 1402, the right ovarian vein 1404, the left ovarian vein 1406, the left renal vein 1408, the right common iliac 1410, the left common iliac 1412, the internal iliac vein 1414, and the uterine venous plexus 1416.

Figure 38A:
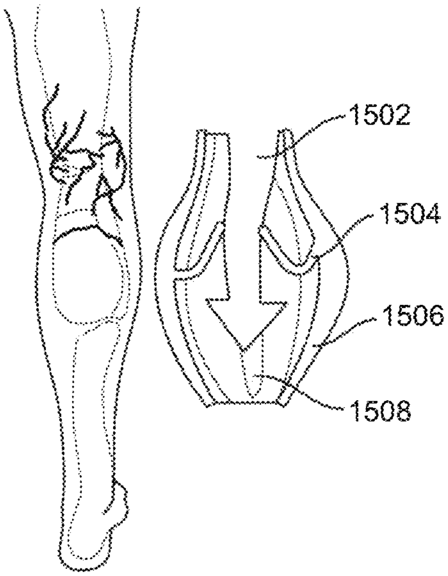
FIGS. 38A and 38B, respectively, illustrate venous blood flow in healthy veins and varicose veins.
Figure 38B:
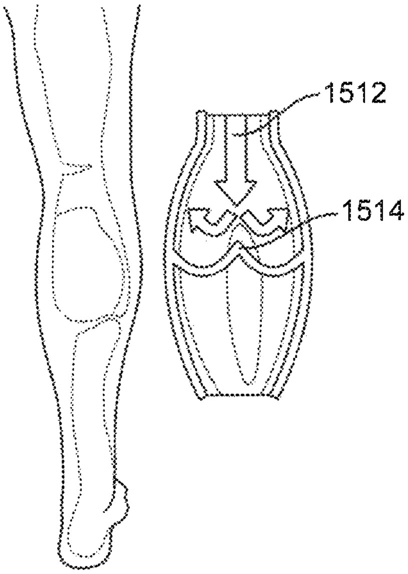

FIGS. 38A and 38B illustrate, respectively, venous blood flow in healthy veins and varicose veins. In FIG. 38B, healthy veins are shown. The arrow 1512 indicates blood flow. Also shown is a properly functioning valve 1514. In FIG. 38A, varicose veins are shown. The arrow 1502 indicates blood flow. A damaged valve 1504 is shown in the blood flow path. This damaged valve 1504 lead to a damaged and bulging vein wall 1506 and blood 1508 collecting in the vein. FIG. 38A makes clear how the distended and damaged walls of varicose veins likely form difficult to drain pockets of blood and fluid. Advantageously, the active aspiration step removes this blood and other fluids to prevent dilution of closure agent when injected.

Figure 22:
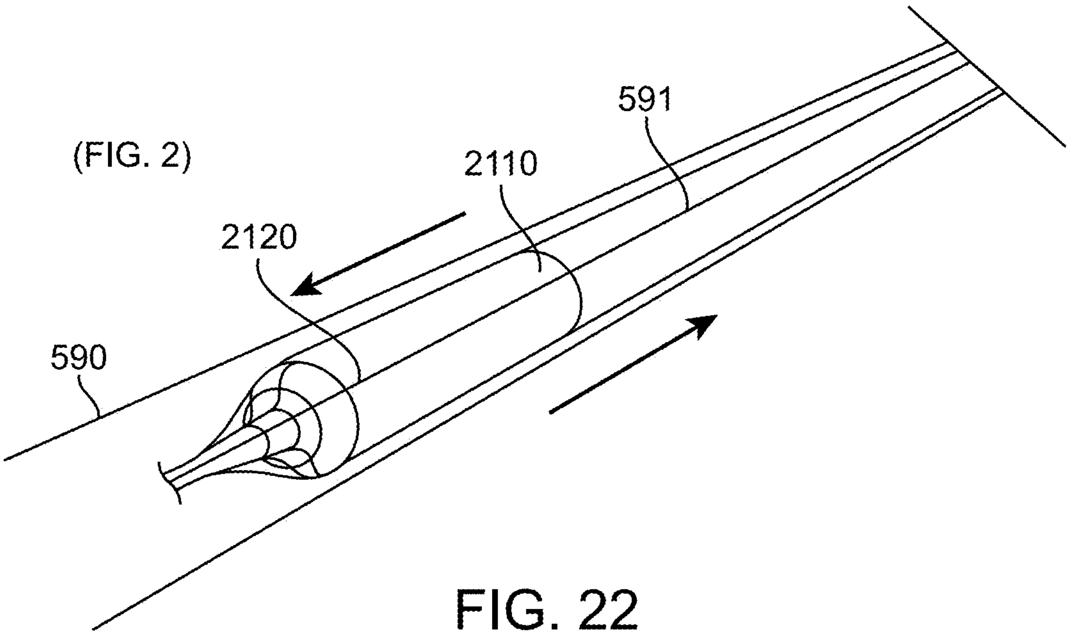
FIG. 22 is a perspective view of an abrasion line formed in a vessel by a longitudinally aligned or no offset abrasion element.

Against this background of the clinical scenario and disease state, we turn to FIG. 22 which is a perspective view of an abrasion line formed in a vessel 590 by a longitudinally aligned or no offset abrasion element. In contrast, FIG. 23 is a perspective view of an abrasion area 595 formed in a vessel 590 by an angular offset abrasion element 550.

Figure 23:
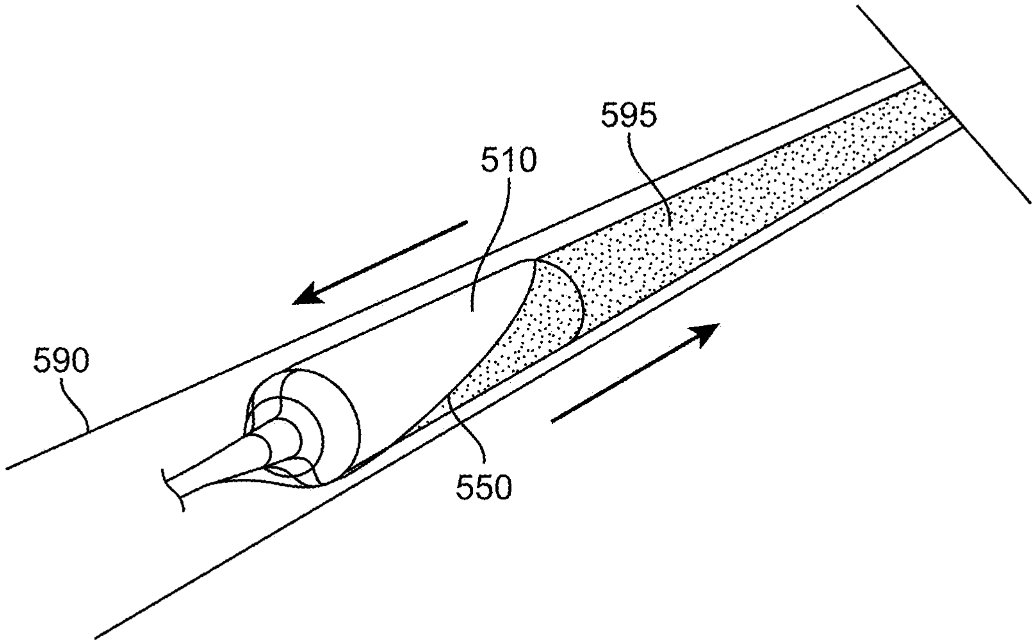
FIG. 23 is a perspective view of an abrasion area formed in a vessel by an angular offset abrasion element.

FIGS. 22 and 23 may be used to compare the abrasion pattern formed by engagement of an in-line or non-angular offset abrasion element 2120 on an inflated balloon 2110 within a vein 590 (see the device in FIG. 2 of the prior art) to the abrasion zone 595 formed in a vein 590 by an embodiment of an angular offset abrasion element 550 on a balloon 510. It is clear that an angular offset abrasion zone can more completely provide for a larger and more controlled abrasion area.

Figure 24A:
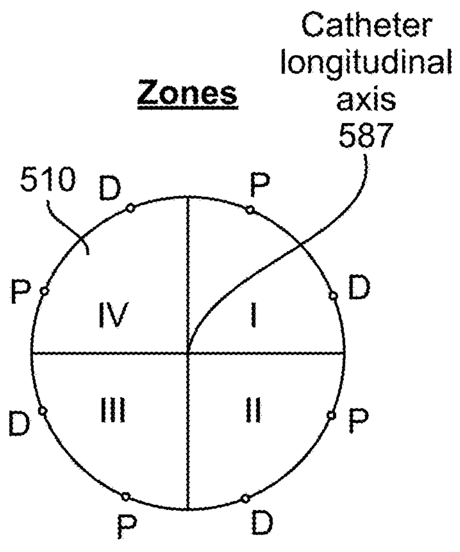
FIG. 24A is an end on view of a representative balloon therapy device having four angular offset abrasion elements with the proximal end (P) and distal end (D) positioned as shown within four 90-degree quadrants arranged about the catheter longitudinal axis.

FIG. 24A is an end on view of a representative balloon therapy device having four angular offset abrasion elements with the proximal end (P) and distal end (D) positioned as shown within four 90-degree quadrants arranged about the catheter longitudinal axis.

Figure 24B:
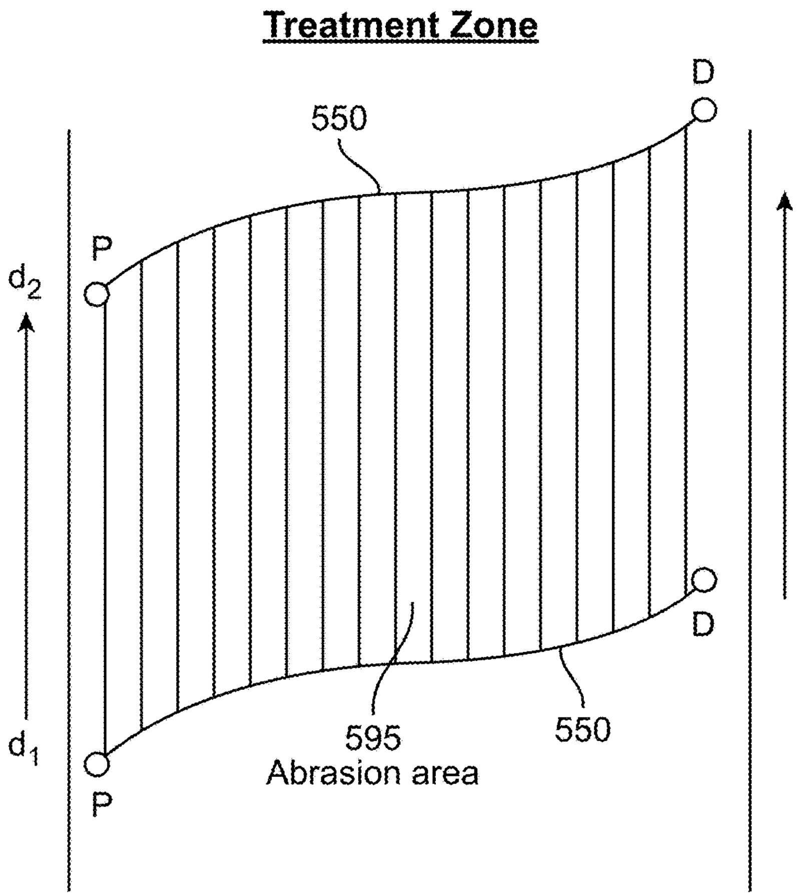
FIG. 24B is a representative abrasion zone of a vessel sidewall that has engaged with an abrasion element of FIG. 24A with the proximal end P and distal end D indicated along with the direction of movement along a closure zone.

FIG. 24B is a representative abrasion zone of a vessel sidewall that has engaged with an abrasion element of FIG. 24A. The vessel wall has been laid flat to show the approximate appearance of an abrasion area 550 as it relates to a number of factors such as the length and angular offset of the proximal end P and distal end D as well as the distance of a closure zone as indicated by d1 and d2. The proximal end P and distal end D indicated along with the direction of movement along a closure zone on the representative abrasion area 595.

Figure 25A:
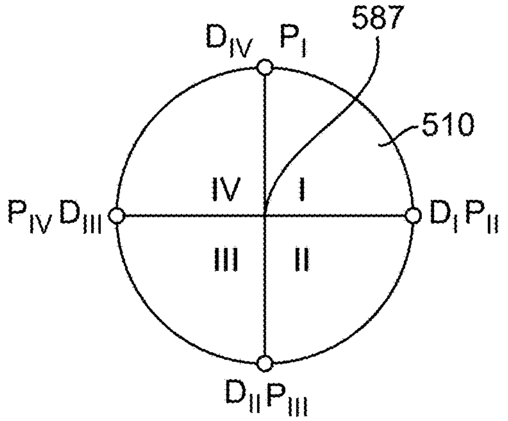
FIG. 25A is an end on view of a representative balloon therapy device similar to device 700 with quadrants 1-IV and the proximal and distal ends of the abrasion elements having an angular offset of 90 degrees.

FIG. 25A is an end on view of a representative balloon therapy device similar to device 700 with quadrants 1-IV arranged about the longitudinal axis 587 of the catheter 505. As shown, the proximal and distal ends of the abrasion elements having an angular offset of 90 degrees.

Figure 25B:
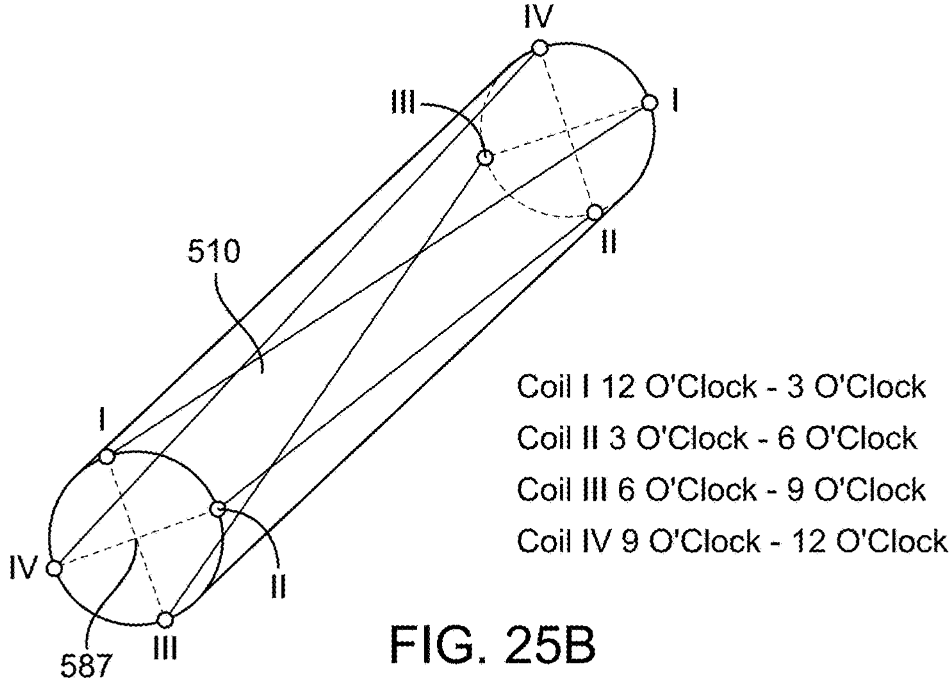
FIG. 25B is a perspective view of the balloon treatment device of FIG. 25 showing the arrangement of each one of the abrasion elements moving along the balloon outer surface about the catheter longitudinal axis.

FIG. 25B is a perspective view of the balloon treatment device of FIG. 25 showing the arrangement of each one of the abrasion elements 550 moving along the balloon 510 outer surface about the catheter longitudinal axis 587.

Figure 25C:
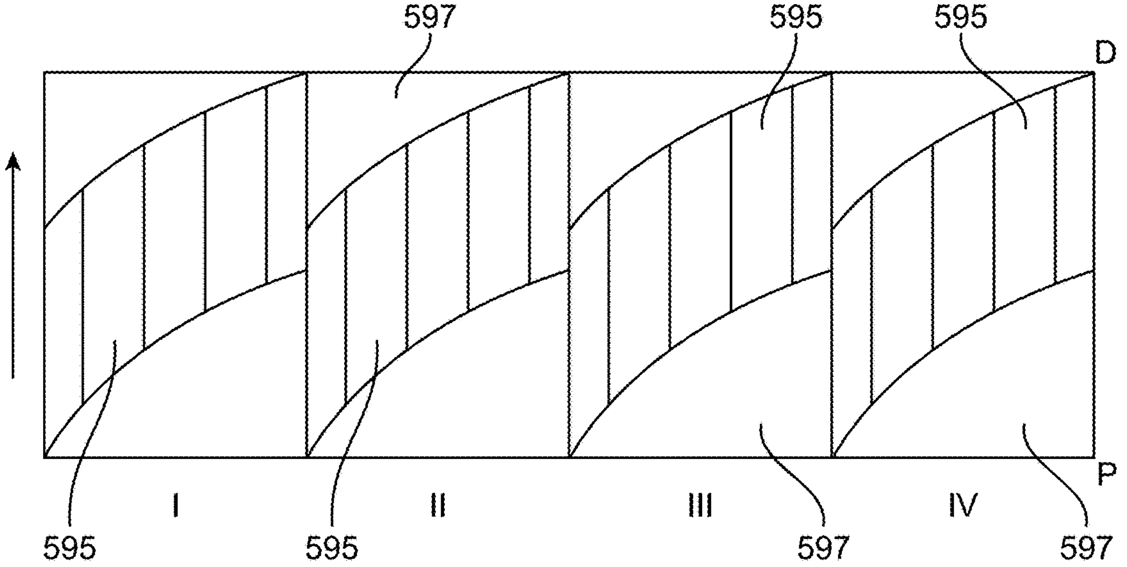
FIG. 25C is a perspective view of the continuous or nearly continues abrasion areas formed by the balloon treatment device of FIGS. 25A and 25B.

FIG. 25C is a perspective view of the treated wall of a vessel after the movement of the partially inflated balloon to form the closure zone. As a result of the uniform spacing and offset alignment (i.e., each zone is similar offset) between the different abrasion elements, there are produced an arrangement of continuous or nearly continues abrasion areas 595 formed by the balloon treatment device of FIGS. 25A and 25B. Adjacent untreated areas 597 are also shown that would be proximal and distal to the closure zone. In other angular offset abrasion element configurations such as in FIGS. 24A and 32A, would produce a combination of abrasion areas 595 that are separated by abrasion spacing areas 597 between abrasion areas 595.

Figure 26:
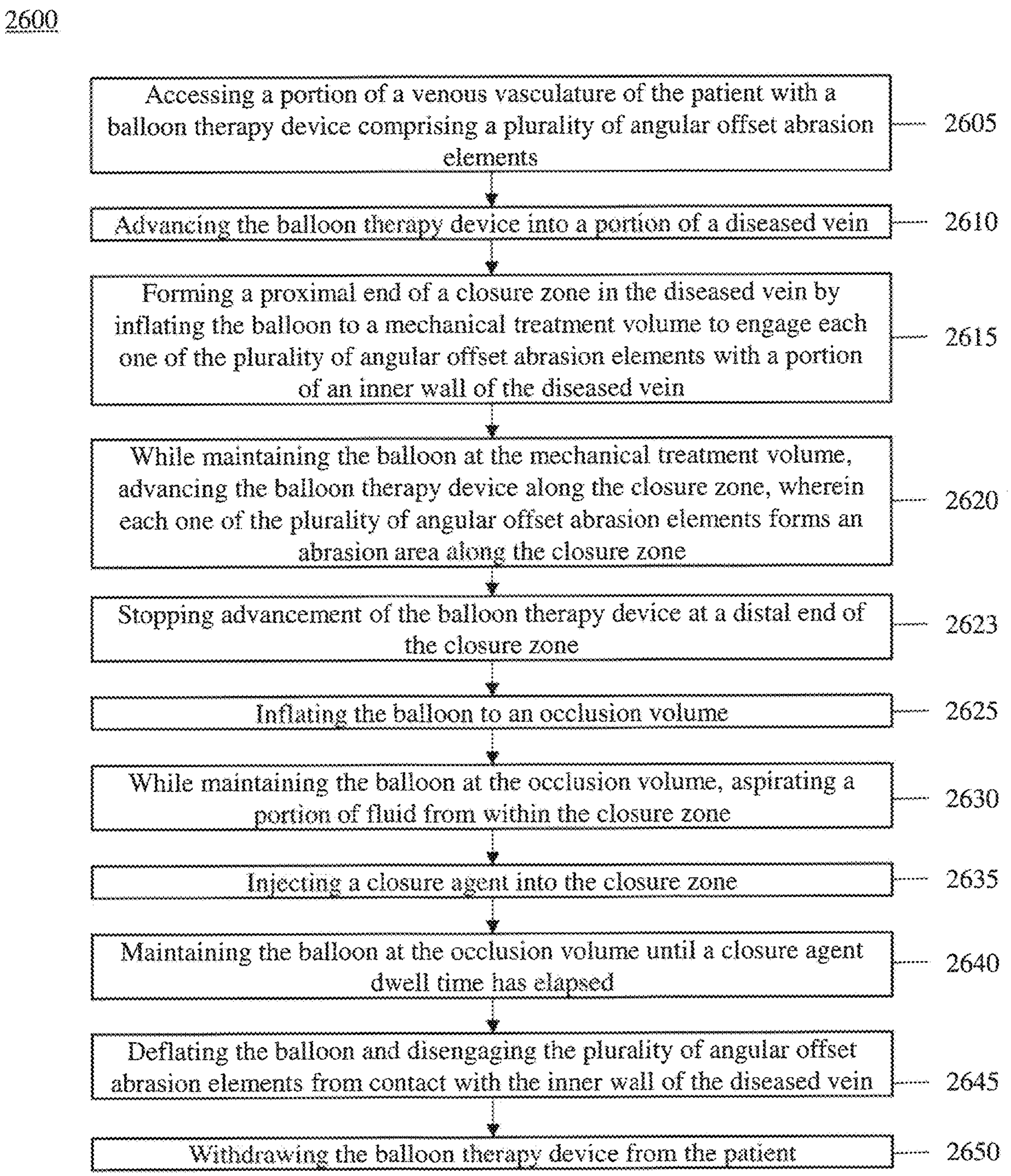
FIG. 26 is a flowchart of an exemplary balloon mechanical therapy treatment method 2600 carried out in steps 2605-2650.

FIG. 26 is a flowchart of an exemplary balloon mechanical therapy treatment method 2600 carried out in steps 2605-2650.

At step 2605, the method 2600 may comprise accessing a portion of a venous vasculature of a patient with a balloon therapy device comprising a plurality of angular offset abrasion elements. In some embodiments, the plurality of angular offset abrasion elements may be 2 or 3 or 4 or 5 or 6 or 7 or 8. In still further embodiments, the plurality of angular offset abrasion elements may be any number between 2-12, wherein the dimensions of the angular offset abrasion elements may allow the catheter of the ballon to comprise a 4 FR diameter, a 5 FR diameter, or a 6 FR diameter. In still further embodiments, the device may be advanced over a guidewire.

At step 2610, the method 2600 may comprise advancing the balloon therapy device into a portion of a diseased vein.

At step 2615, the method 2600 may comprise forming a proximal end of a closure zone in the diseased vein by inflating the balloon to a mechanical treatment volume to engage each one of the plurality of angular offset abrasion elements with a portion of an inner wall of the diseased vein.

In some embodiments, inflating the balloon to a mechanical treatment volume may comprise visualizing the balloon using imaging (e.g., ultrasound guidance) and inflating it until it contact the vein wall. At that point, the clinician may stop inflating or inflate about an additional 0.25-0.5 cc. Additional inflation may be needed to accommodate changes in vessel diameter along the length of the closure zone.

Inflating the balloon may comprise attaching a syringe to the inflation port and inflating the balloon with a fluid, such as saline, contrast or air. The inflation level may be adjusted throughout the method, using the syringe.

At step 2620, the method 2600 may comprise advancing the balloon therapy device along the closure zone while maintaining the balloon at the mechanical treatment volume, wherein each one of the plurality of angular offset abrasion elements may form an abrasion area along the closure zone. In further embodiments, the abrasion area formed by the angular offset abrasion elements along the closure zone may be continuous, substantially continuous (i.e., small gaps between the abrasion areas, as seen in FIG. 25C), or segmental (i.e., discrete areas between abrasion areas or abraded wall areas, as seen in FIG. 32C).

At step 2623, the method 2600 may comprise stopping advancement of the balloon therapy device at a distal end of the closure zone.

At step 2625, the method 2600 may comprise inflating the balloon to an occlusion volume. The occlusion volume may vary based on, for example, the balloon size and vessel size. In some embodiments, the occlusion volume may be about 2-3 cc.

At step 2630, the method 2600 may comprise aspirating a portion of fluid from within the closure zone while maintaining the balloon at the occlusion volume.

At step 2635, a closure agent may be injected into the closure zone.

At step 2640, the method 2600 may comprise maintaining the balloon at the occlusion volume until a closure agent dwell time has elapsed. In some embodiments, the dwell time may comprise about 2-5 minutes. The dwell time may be as long as 10 minutes and may vary based on the recommended uses of a particular closure agent.

At step 2645, the method 2600 may comprise deflating the balloon and disengaging the plurality of angular offset abrasion elements from contact with the inner wall of the diseased vein. Deflating the balloon may comprise using the syringe to remove fluid from the balloon. In some embodiments, deflating the balloon may comprise completely deflating the balloon. In some embodiments, deflating the balloon may comprise mostly deflating the balloon (e.g., greater than about 90% of its volume).

At step 2650, the method 2600 may comprise withdrawing the balloon therapy from the patient.

It will be appreciated that the method 2600 may include any other variation or additions as described herein.

Figure 27:
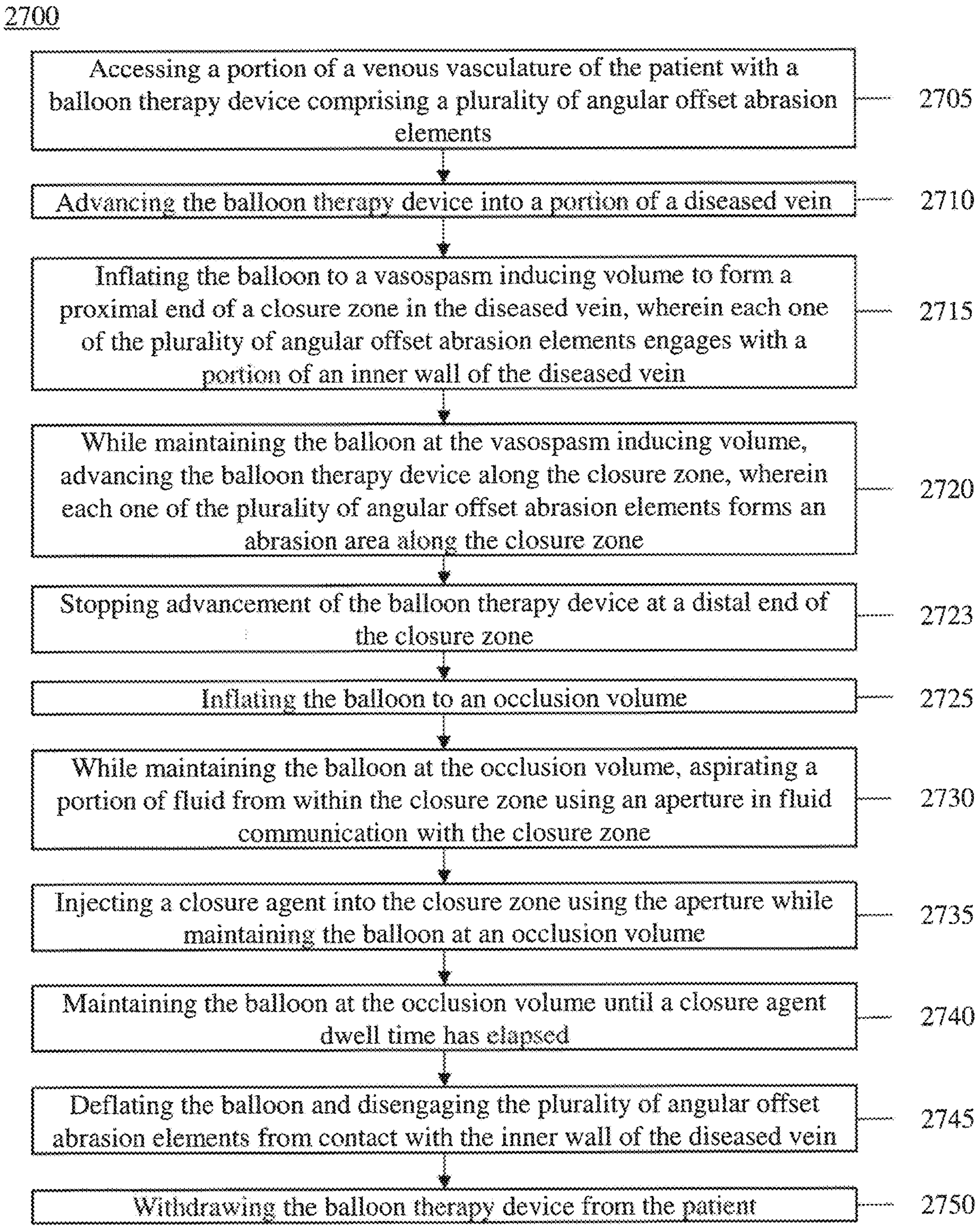
FIG. 27 is a flowchart of an exemplary balloon therapy treatment method 2700 inducing vasospasm/endothelium injury and carried out in steps 2705-2750.

FIG. 27 is a flowchart of an exemplary balloon therapy treatment method 2700 inducing vasospasm/endothelial injury and carried out in steps 2705-2750. Unless described otherwise, the steps may be similar to those described with respect to FIG. 26.

At step 2705, the method 2700 may comprise accessing a portion of a venous vasculature of the patient with a balloon therapy device comprising a plurality of angular offset abrasion elements. In some embodiments, the plurality of angular offset abrasion elements may be 2 or 3 or 4 or 5 or 6 or 7 or 8. In still further embodiments, the plurality of angular offset abrasion elements may be any number between 2-12, wherein the dimensions of the angular offset abrasion elements may allow the catheter of the ballon to comprise a 4 FR diameter, a 5 FR diameter, or a 6 FR diameter. In still further embodiments, the device may be advanced over a guidewire.

At step 2710, the method 2700 may comprise advancing the balloon therapy device into a portion of a diseased vein.

At step 2715, the method 2700 may comprise inflating the balloon to a venospasm inducing volume to form a proximal end of a closure zone in the diseased vein, wherein each of the plurality of angular offset abrasion elements may engage with a portion of an inner wall of the diseased vein.

In some embodiments, inflating the balloon to a venospasm inducing volume may comprise visualizing the balloon using imaging (e.g., ultrasound guidance) and inflating it until it contacts the vein wall. At that point, the clinician may stop inflating or inflate about an additional 0.25-0.5 cc. Additional inflation may be needed to accommodate changes in vessel diameter along the length of the closure zone.

Inflating the balloon may further comprise attaching a syringe to the inflation port and inflating the balloon with a fluid, such as saline. The inflation level may be adjusted throughout the method, using the syringe.

At step 2720, the method 2700 may comprise advancing the balloon therapy device along the closure zone, wherein each one of the plurality of angular offset abrasion elements may form an abrasion area long the closure zone. In further embodiments, the abrasion area formed by the angular offset abrasion elements along the closure zone may be continuous, substantially continuous (i.e., small gaps between the abrasion areas, as seen in FIG. 25C), or segmental (i.e., discrete areas between abrasion areas or abraded wall areas, as seen in FIG. 32C).

At step 2723, the method 2700 may comprise stopping advancement of the balloon therapy device at a distal end of the closure zone.

At step 2725, the method 2700 may comprise inflating the balloon to an occlusion volume. The occlusion volume may vary based on, for example, the balloon size and vessel size. In some embodiments, the occlusion volume may be about 2-3 cc.

At step 2730, the method 2700 may comprise aspirating a portion of fluid from within the closure zone using an aperture in fluid communication with the closure zone. In some embodiments, the method 2700 may comprise aspirating all of the fluid from within the closure zone. In some embodiments, the method comprises most (e.g., greater than 50%, greater than 60%, greater than 70%, greater than 80%, greater than 90%, etc.) of the fluid from within the closure zone.

At step 2735, the method 2700 may comprise injecting a closure agent into the closure zone using the aperture while maintaining the balloon at an occlusion volume.

In step 2740, the method 2700 may comprise maintaining the balloon at the occlusion volume until a closure agent dwell time has elapsed.

At step 2745, the method 2700 may comprise deflating the balloon and disengaging the plurality of angular offset abrasion elements from contact with the inner wall of the diseased vein. Deflating the balloon may comprise using the syringe to remove fluid from the balloon. In some embodiments, deflating the balloon may comprise completely deflating the balloon. In some embodiments, deflating the balloon may comprise mostly deflating the balloon (e.g., greater than about 90% of its volume).

At step 2750, the method 2700 may comprise withdrawing the balloon therapy device from the patient.

It will be appreciated that the method 2700 may include any other variation or additions as described herein.

Figure 28:
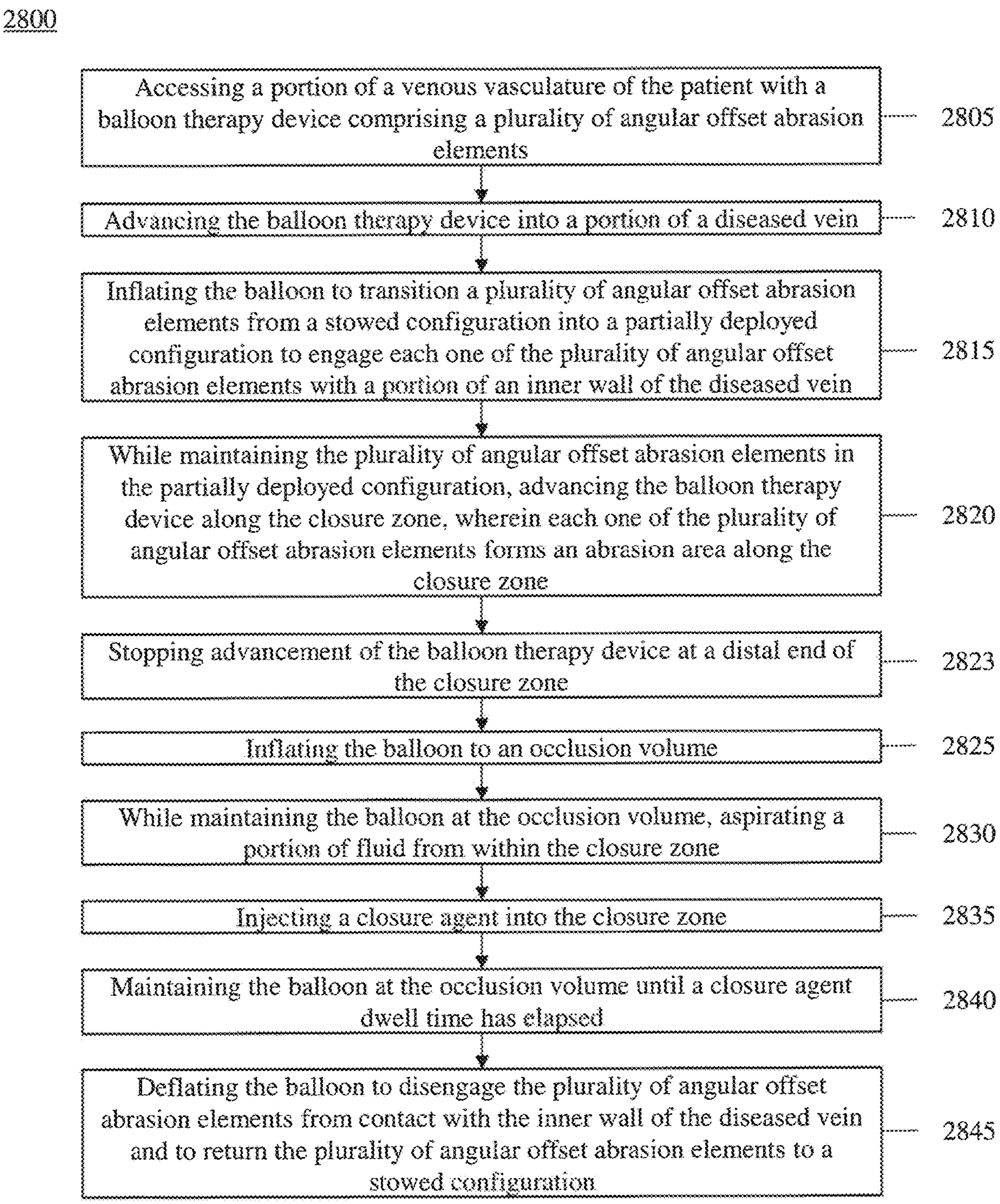
FIG. 28 is a flowchart of an exemplary balloon therapy treatment method 2800 employing a plurality of angular offset abrasion elements and carried out in steps 2805-2850.

FIG. 28 is a flowchart of an exemplary balloon therapy treatment method 2800 employing a plurality of angular offset abrasion elements and carried out in steps 2805-2845. Unless described otherwise, the method may comprise similar steps to those carried out and described with respect to FIGS. 26 and 27.

At step 2805, the method 2800 may comprise accessing a portion of a venous vasculature of the patient with a balloon therapy device comprising a plurality of angular offset abrasion elements. In some embodiments, the plurality of angular offset abrasion elements may be 2 or 3 or 4 or 5 or 6 or 7 or 8. In still further embodiments, the plurality of angular offset abrasion elements may be any number between 2-12, wherein the dimensions of the angular offset abrasion elements may allow the catheter of the ballon to comprise a 4 FR diameter, a 5 FR diameter, or a 6 FR diameter. In still further embodiments, the device may be advanced over a guidewire.

At step 2810, the method 2800 may comprise advancing the balloon therapy device into a portion of a diseased vein.

At step 2815, the method 2800 may comprise inflating the balloon to transition a plurality of angular offset abrasion elements from a stowed configuration into a partially deployed configuration to engage each one of the plurality of angular offset abrasion elements with a portion of an inner wall of the diseased vein.

In some embodiments, inflating the balloon to transition a plurality of angular offset abrasion elements from a stowed configuration into a partially deployed configuration may comprise visualizing the balloon using imaging (e.g., ultrasound guidance) and inflating it until it contacts the vein wall. At that point, the clinician may stop inflating or inflate about an additional 0.25-0.5 cc. Additional inflation may be needed to accommodate changes in vessel diameter along the length of the closure zone.

Inflating the balloon may comprise attaching a syringe to the inflation port and inflating the balloon with a fluid, such as saline. The inflation level may be adjusted throughout the method, using the syringe.

At step 2820, the method 2800 may comprise advancing the balloon therapy device along the closure zone while maintaining each one of the plurality of angular offset abrasion elements in the partially deployed configuration, wherein each one of the plurality of angular offset abrasion elements may form an abrasion area along the closure zone. In further embodiments, the abrasion area formed by the angular offset abrasion elements along the closure zone may be continuous, substantially continuous (i.e., small gaps between the abrasion areas, as seen in FIG. 25C), or segmental (i.e., discrete areas between abrasion areas or abraded wall areas, as seen in FIG. 32C).

In still further embodiments, it will be appreciated that this advancement with the plurality of angular offset abrasion elements at least partially deployed may induce venospasm within at least a portion of the closure zone.

At step 2823, the method 2800 may comprise stopping advancement of the balloon therapy device at a distal end of the closure zone.

At step 2825, the method 2800 may comprise inflating the balloon to an occlusion volume. The occlusion volume may vary based on, for example, the balloon size and vessel size. In some embodiments, the occlusion volume may about 2-3 cc.

At step 2830, the method 2800 may comprise aspirating a portion of fluid from within the closure zone, while maintaining the balloon at the occlusion volume.

In some embodiments, the method 2800 may comprise aspirating all of the fluid from within the closure zone. In some embodiments, the method 2800 may comprise most (e.g., greater than 50%, greater than 60%, greater than 70%, greater than 80%, greater than 90%, etc.) of the fluid from within the closure zone.

At step 2835, the method 2800 may comprise injecting a closure agent into the closure zone.

At step 2840, the method 2800 may comprise maintaining the balloon at the occlusion volume until a closure agent dwell time has elapsed. In some embodiments, the dwell time may be about 2-5 minutes.

At step 2845, the method 2800 may comprise deflating the balloon to disengage the plurality of angular offset abrasion elements from contact with the inner wall of the diseased vein and to return the plurality of angular offset abrasion elements to a stowed configuration. Deflating the balloon may comprise using the syringe to remove fluid from the balloon. In some embodiments, deflating the balloon may comprise completely deflating the balloon. In some embodiments, deflating the balloon may comprise mostly deflating the balloon (e.g., greater than about 90% of its volume).

Moreover, the method 2800 may further comprise withdrawing the device.

It will be appreciated that the method 2800 may include any other variation or additions as described herein.

Figure 29:
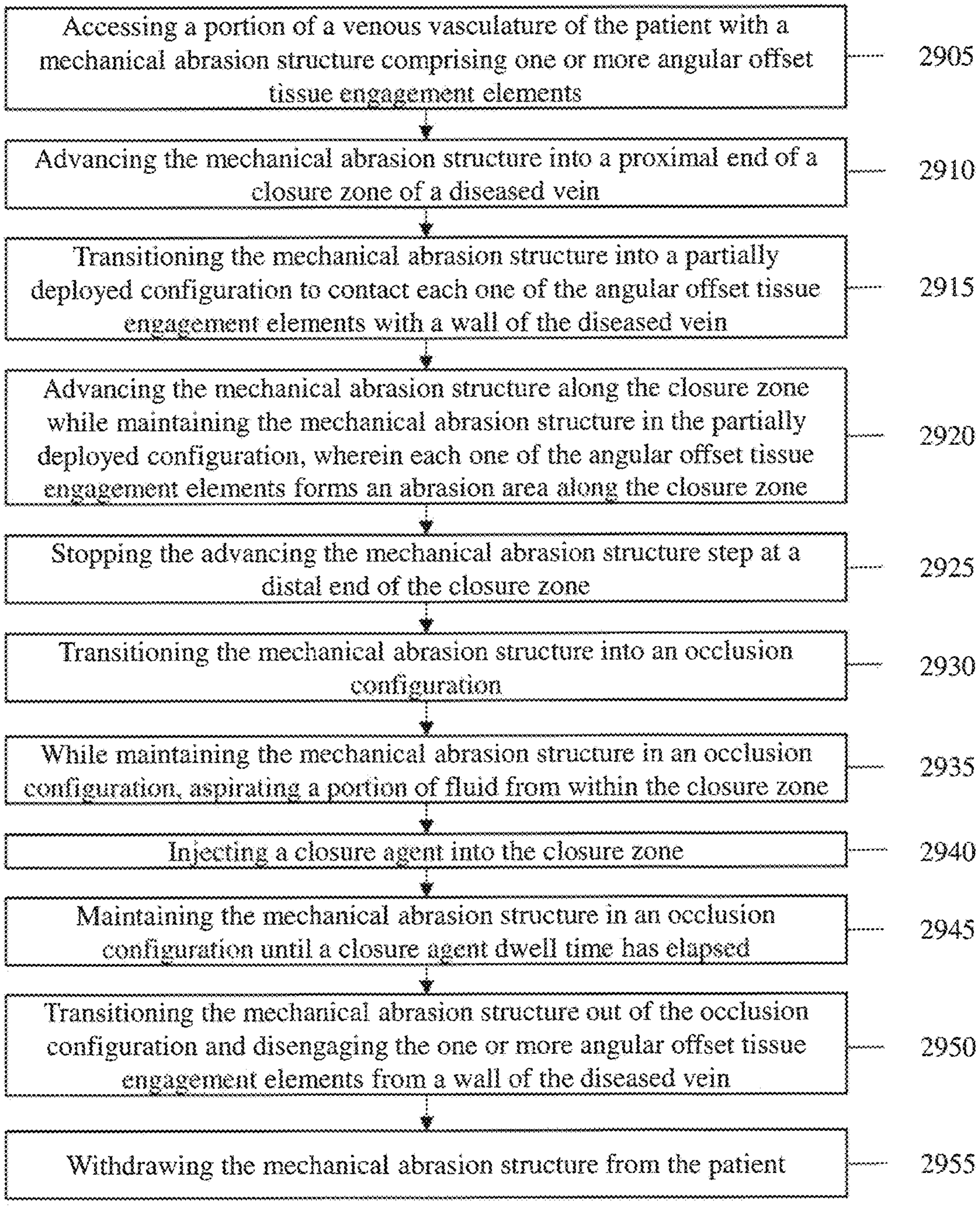
FIG. 29 is a flowchart of an exemplary balloon therapy treatment method 2900 employing a mechanical abrasion structure and one or more angular offset tissue engagement elements carried out in steps 2905-2955.

FIG. 29 is a flowchart of an exemplary balloon therapy treatment method 2900 employing a mechanical abrasion structure comprising one or more angular offset tissue engagement elements carried out in steps 2905-2955. Unless described otherwise, FIG. 29 may comprise steps similar to those described with respect to FIGS. 26-28.

At step 2905, the method 2900 may comprise accessing a portion of a venous vasculature of the patient with a mechanical abrasion structure having one or more angular offset tissue engagement elements. In some embodiments, the one or more angular offset tissue engagement elements may be 2 or 3 or 4 or 5 or 6 or 7 or 8. In still further embodiments, the one or more angular offset tissue engagement elements may be any number between 2-12, wherein the dimensions of the angular offset abrasion elements may allow the catheter of the ballon to comprise a 4 FR diameter, a 5 FR diameter, or a 6 FR diameter. In still further embodiments, the device may be advanced over a guidewire At step 2910, the method 2900 may comprise advancing the mechanical abrasion structure into a proximal end of a closure zone of a diseased vein.

At step 2915, the method 2900 may comprise transitioning the mechanical abrasion structure into a partially deployed configuration to contact each one of the angular offset tissue engagement elements with a wall of the diseased vein.

In some embodiments, inflating the balloon to transition a mechanical abrasion structure into a partially deployed configuration may comprise visualizing the balloon using imaging (e.g., ultrasound guidance) and inflating it until it contacts the vein wall. At that point, the clinician may stop inflating or inflate about an additional 0.25-0.5 cc. Additional inflation may be needed to accommodate changes in vessel diameter along the length of the closure zone.

At step 2920, the method 2900 may comprise advancing the mechanical abrasion structure along the closure zone while maintaining the mechanical abrasion structure in the partially deployed configuration, wherein each one of the angular offset tissue engagement elements may form an abrasion area along the closure zone. In further embodiments, the abrasion area formed by the angular offset tissue engagement elements along the closure zone may be continuous, substantially continuous (i.e., small gaps between the abrasion areas, as seen in FIG. 25C), or segmental (i.e., discrete areas between abrasion areas or abraded wall areas, as seen in FIG. 32C). Further, it will be appreciated that this advancement with the angular offset tissue engagement elements at least partially deployed may induce venospasm and/or collapse within at least a portion of the closure zone.

At step 2925, the method 2900 may comprise stopping the advancing of the mechanical abrasion structure step at a distal end of the closure zone.

At step 2930, the method 2900 may comprise transitioning the mechanical abrasion structure into an occlusion configuration. In some embodiments, transitioning the mechanical abrasion structure into an occlusion configuration mya comprise inflating a balloon to an occlusion volume and moving the mechanical abrasion structure towards the venous walls.

The occlusion volume may vary based on, for example, the balloon size and vessel size. In some embodiments, the occlusion volume is about 2-3 cc.

At step 2935, the method 2900 may comprise aspirating a portion of fluid from within the closure zone while maintaining the mechanical abrasion structure in an occlusion configuration. In some embodiments, the method 2900 may comprise aspirating all of the fluid from within the closure zone. In some embodiments, the method 2900 may comprise most (e.g., greater than 50%, greater than 60%, greater than 70%, greater than 80%, greater than 90%, etc.) of the fluid from within the closure zone.

At step 2940, the method 2900 may comprise injecting a closure agent into the closure zone.

At step 2945, the method 2900 may comprise maintaining the mechanical abrasion structure in an occlusion configuration until a closure agent dwell time has elapsed. In some embodiments, the closure agent dwell time may be about 2-5 minutes.

At step 2950, the method 2900 may comprise transitioning the mechanical abrasion structure out of the occlusion configuration and disengaging the one or more angular offset tissue engagement elements from a wall of the diseased vein.

In some embodiments, transitioning the mechanical abrasion structure out of the occlusion configuration comprises at least partially deflating a balloon on the device, thereby moving the mechanical abrasion structure away from the venous wall.

Deflating the balloon may comprise using the syringe to remove fluid from the balloon. In some embodiments, deflating the balloon mya comprise completely deflating the balloon. In some embodiments, deflating the balloon may comprise mostly deflating the balloon (e.g., greater than about 90% of its volume).

At step 2955, the method 2900 may comprise withdrawing the mechanical abrasion structure from the patient.

It will be appreciated that the method 2900 may include any other variation or additions as described herein.

Figure 30:
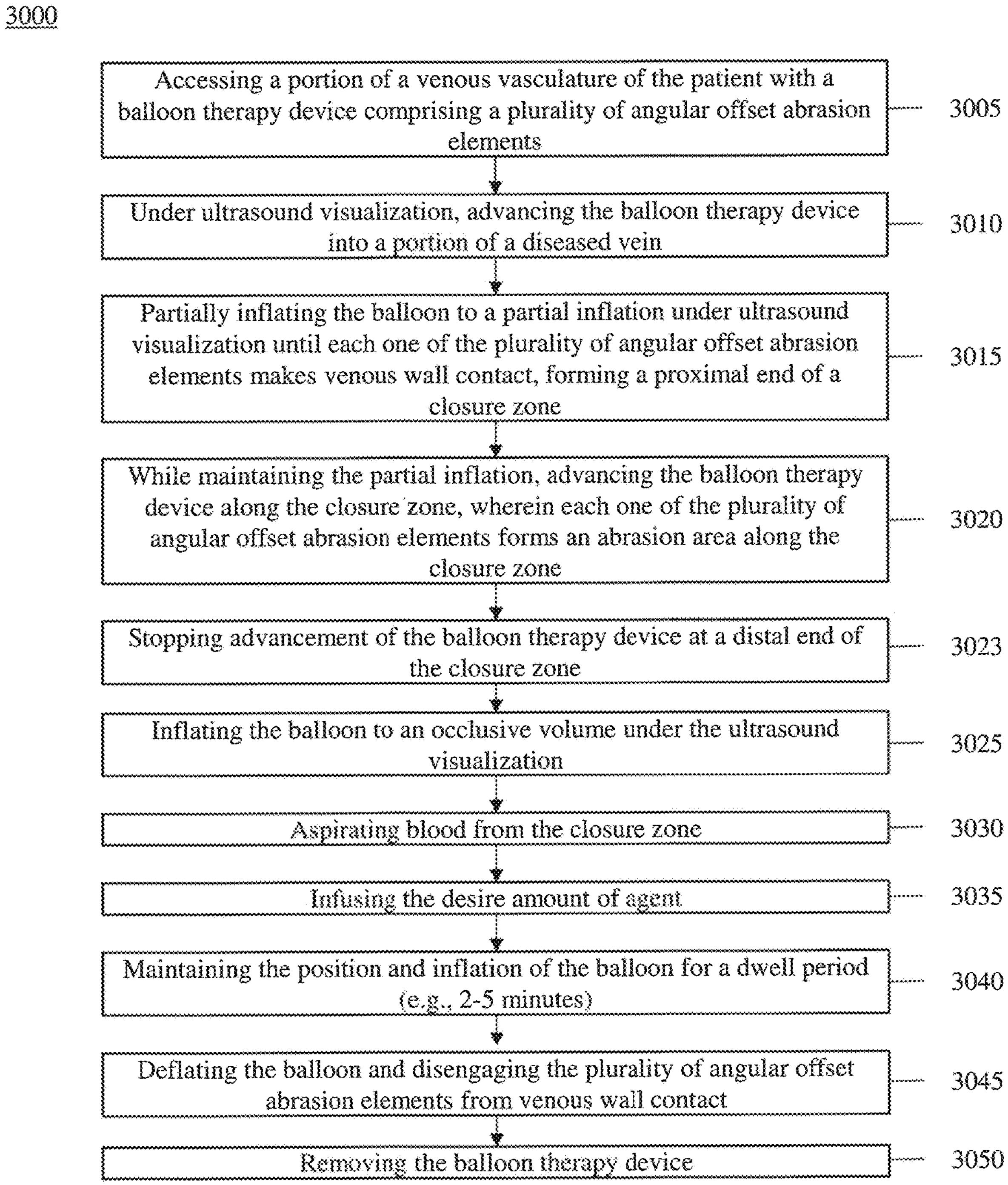
FIG. 30 is a flowchart of an exemplary balloon therapy treatment method 3000 employing a plurality of angular offset abrasion elements and carried out in steps 3005-3050.

FIG. 30 is a flowchart showing a balloon therapy treatment method 3000 employing a plurality of angular offset abrasion elements carried out in steps 3005-3050.

At step 3005, the method 3000 may comprise accessing a portion of a venous vasculature of the patient with a balloon therapy device comprising a plurality of angular offset abrasion elements. In some embodiments, the plurality of angular offset abrasion elements may be 2 or 3 or 4 or 5 or 6 or 7 or 8. In still further embodiments, the plurality of angular offset abrasion elements may be any number between 2-12, wherein the dimensions of the angular offset abrasion elements may allow the catheter of the ballon to comprise a 4 FR diameter, a 5 FR diameter, or a 6 FR diameter. In still further embodiments, the device may be advanced over a guidewire.

At step 3010, the method 3000 may comprise advancing the balloon therapy device into a portion of the diseased vein under ultrasound visualization.

At step 3015, the method 3000 may comprise partially inflating the balloon to a partial inflation under ultrasound visualization until each one of the plurality of angular offset abrasion elements makes venous wall contact, forming a proximal end of a closure zone.

Inflating until each one of the plurality of angular offset abrasion elements makes venous wall contact may comprise inflating until or just past (e.g., 0.25-0.5 cc additional) the point at which the clinician sees venous wall contact using ultrasound visualization.

At step 3020, the method 3000 may comprise advancing the balloon therapy device along the closure zone while maintaining the partial inflation, wherein each one of the plurality of angular offset abrasion elements forms an abrasion area along the closure zone. In further embodiments, the abrasion area formed by the angular offset abrasion elements along the closure zone may be continuous, substantially continuous (i.e., small gaps between the abrasion areas, as seen in FIG. 25C), or segmental (i.e., discrete areas between abrasion areas or abraded wall areas, as seen in FIG. 32C).

At step 3023, the method 3000 may comprise stopping advancement of the balloon therapy device at a distal end of the closure zone.

At step 3025, the method 3000 may comprise inflating the balloon to an occlusive volume under ultrasound visualization. The occlusive volume may vary based on, for example, the balloon size and vessel size. In some embodiments, the occlusion volume may about 2-3 cc.

At step 3030, the method 3000 may comprise aspirating blood from the closure zone. In some embodiments, the method may comprise aspirating all of the fluid from within the closure zone. In some embodiments, the method may comprise most (e.g., greater than 50%, greater than 60%, greater than 70%, greater than 80%, greater than 90%, etc.) of the fluid from within the closure zone.

At step 3035, the method 3000 may comprise infusing the desired amount of agent.

At step 3040, the method 3000 may comprise maintaining the position and inflation of the balloon for a dwell period. In some embodiments, the dwell period may be about 2-5 minutes. Other dwell periods may also be possible (e.g., 1-6 minutes, 2-4 minutes, 3-5 minutes, 3-4 minutes, 3 minutes, 4 minutes, etc.).

At step 3045, the method 3000 may comprise deflating the balloon and disengaging the plurality of angular offset abrasion elements from venous wall contact. Deflating the balloon may comprise using the syringe to remove fluid from the balloon. In some embodiments, deflating the balloon may comprise completely deflating the balloon. In some embodiments, deflating the balloon may comprise mostly deflating the balloon (e.g., greater than about 90% of its volume).

At step 3050, the method 3000 may comprise removing the balloon therapy device.

It will be appreciated that the method 3000 may include any other variation or additions as described herein.

In some embodiments, the methods described above (e.g., methods 2600-3000) may comprise performing subsequent treatments. Prior to withdrawing the device, the device may be retracted proximally and then used to treat a second closure zone (e.g., by partially inflating, advancing the partially inflated balloon, inflating to an occlusive volume, aspirating, injecting a closure agent, and maintaining occlusive volume for a desired dwell time). After completion of the desired number of subsequent treatments, the device may be withdrawn from the patient.

FIGS. 31A-31F provide exemplary steps of a method of forming a treatment zone with an arrangement of abrasion areas as well as occluding a vessel and delivering a treatment agent. As will be discussed further below, additional details are provided below with respect to the methods 2600, 2700, 2800, 2900 and 3000 described in FIGS. 26-30. These methods illustrate how a two-step or multiple intermediate step engagement with the diseased vein wall is used along with active aspiration of a closure section prior to injection of a closure agent. The diseased vessel has been illustrated as a cylinder so that the operation of the partial and occlusion deployment volumes and various dimensions of the balloon and movement of the balloon therapy device may be more clearly presented. It is to be appreciated that the term mechanical treatment pressure refers to a level of contact between an inflated balloon in order to provide the desired level of engagement between one or more angular offset abrasion elements of a balloon therapy device and a wall of a vessel within a treatment zone. In many cases, this desired amount of contact is provided by controlling the volume of fluid injected into the balloon volume in combination with the characteristics and arrangement of the plurality of angular offset abrasion elements. It is also to be appreciated that, while the walls of the vein are shown as patent throughout the method of FIGS. 31A-31F, the walls may be and most likely are subject to venospasm and collapse during the method.

Figure 31A:
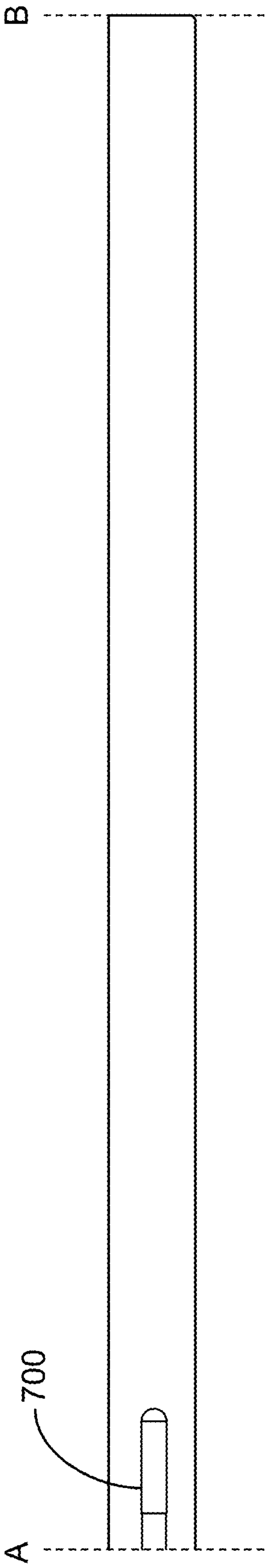
FIGS. 31A-31F provide exemplary steps of the methods of FIGS. 26-30 how a twostep or staged engagement with the diseased vein wall is used to form abrasion areas along a closure zone along with active aspiration of a closure section prior to injection of a closure agent. The diseased vessel has been illustrated as a cylinder so that the operation of the partial and occlusion deployment volumes/dimensions and movement of the angular offset balloon therapy device may be more clearly presented.
Figure 31B:
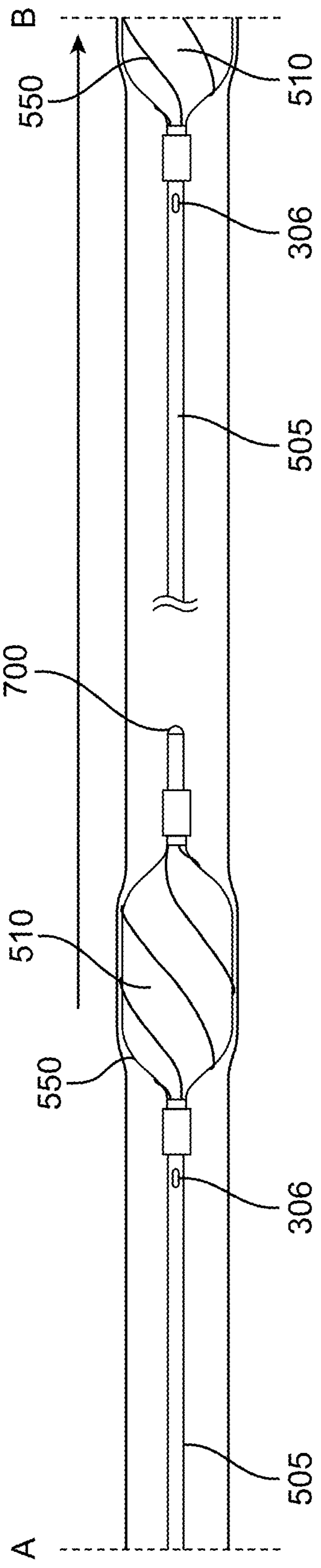

In FIG. 31A, the device 700 is inserted, in a stowed position, within the vein to a point A, the beginning point of vein segment A-B. The segment A-B is a closure zone. In FIG. 31B, the device 700 is advanced in a direction indicated by the arrow toward point B, an ending point of the segment A-B. The angular offset abrasion elements 550 of the device engage the wall as the device advances towards point B.

Prior to and during advancement of the device 700 from point A to point B, the balloon 510 may be at least partially inflated to engage the angular offset abrasion elements 550 with the vessel wall. The vessel wall is shown slightly distended at point which would have been completed at Point A—the proximal end of the closure zone. Once the abrasion elements are engaged and as a function of the angular offset, an abrasion area will be formed along the walls of the closure zone. The right-hand end of FIG. 31B also illustrates that the partially inflated balloon treatment device 700 has advanced to the distal end of the closure (Point B).

In some embodiments, the balloon 510 is inflated, under ultrasonographic guidance, until the balloon makes contact with the vein wall. Once the clinician visualizes vein wall contact, the clinician may either stop inflation or inflate an additional small volume (e.g., about 0.25-0.50 cc). Such small additional inflation volumes may be needed to accommodate vessel wall elasticity or increases in vessel size.

It will be appreciated that, in some embodiments, engagement of the vessel wall with the offset abrasion elements may cause venospasm.

Figure 31C:
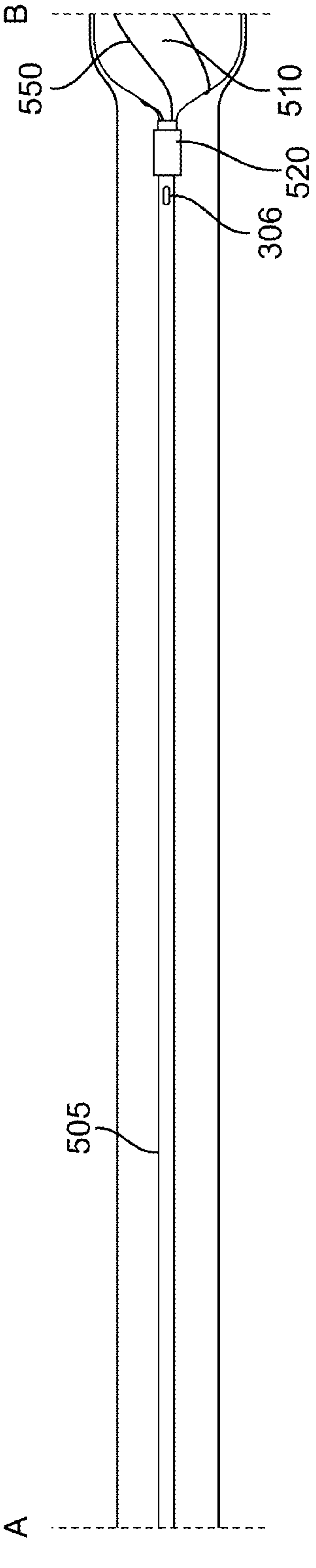

As shown in FIG. 31C, once the device has reached point B, the balloon 510 may be fully expanded to an occlusive volume, isolating the treatment area. Expansion of the balloon to an occlusion volume further distends the vein wall (compare with FIG. 31B). The diameter of the balloon when inflated to an occlusion volume is between 7 mm-13 mm depending upon the characteristics of the vessel being treated.

In one embodiment, expanding the balloon to its full volume can comprise inflating the balloon to about 2-3 cc.

Figure 31D:
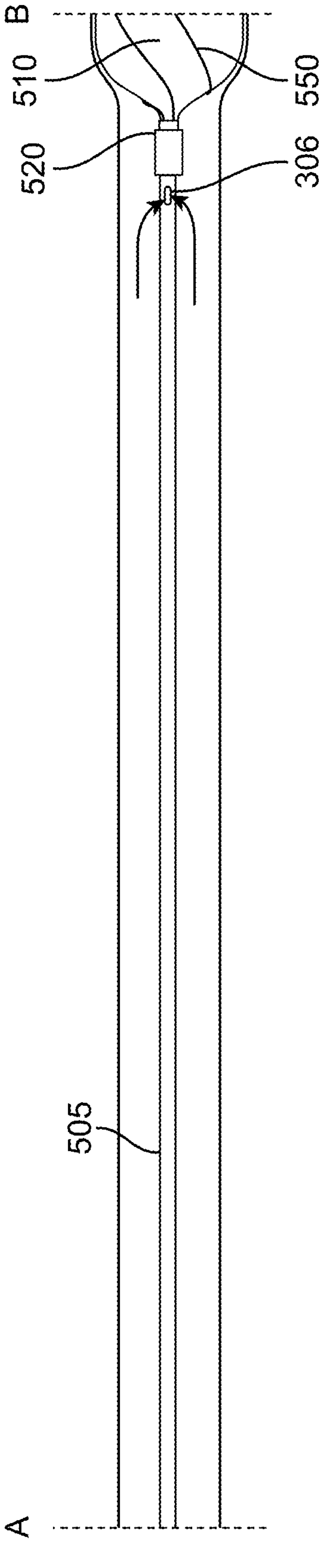

As shown in FIGS. 31C and 31D, the partially inflated balloon comprises a smaller surface area in contact with the vessel wall than the balloon inflated to an occlusive volume. The smaller surface area engaged with the wall at the partially inflated volume allows the balloon to advance through the vessel while still engaging the wall. At the occlusive volume, the greater surface area engaged with the vessel wall can help to occlude the vessel and fix the balloon in place during treatment.

In some embodiments, at the occlusive volume, as shown in FIGS. 31C and 31D, the balloon is inflating and elongating and increasing the contact surface area with the vein wall, which is also being distended and thinning.

As shown in FIG. 31D, after isolation using occlusion volume, blood and fluids can be aspirated from the closure zone using aspiration and injection port 306 and lumen 544 connected to a syringe. Fluids are withdrawn into port 306 as indicated by the arrows.

Figure 31E:
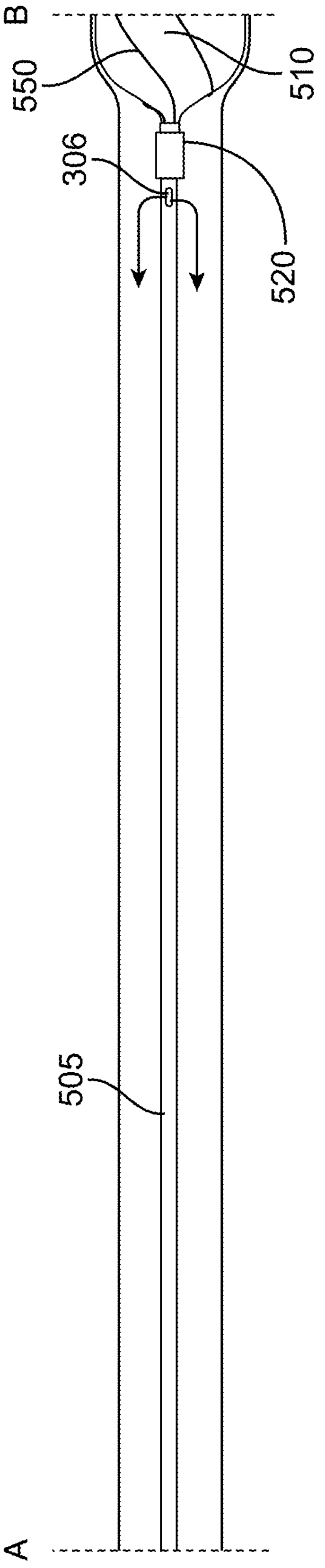

Moving to FIG. 31E, after aspiration, injection of a closure agent (e.g., foam) can be performed. The closure agent can be injected into the treatment area as indicated by the arrows through the aspiration and injection port 306 via fluid lumen 544 and fluid port 576.

In some embodiments, the closure agent is allowed to dwell at the treatment area for a period of time (e.g., 2-5 minutes).

Figure 31F:
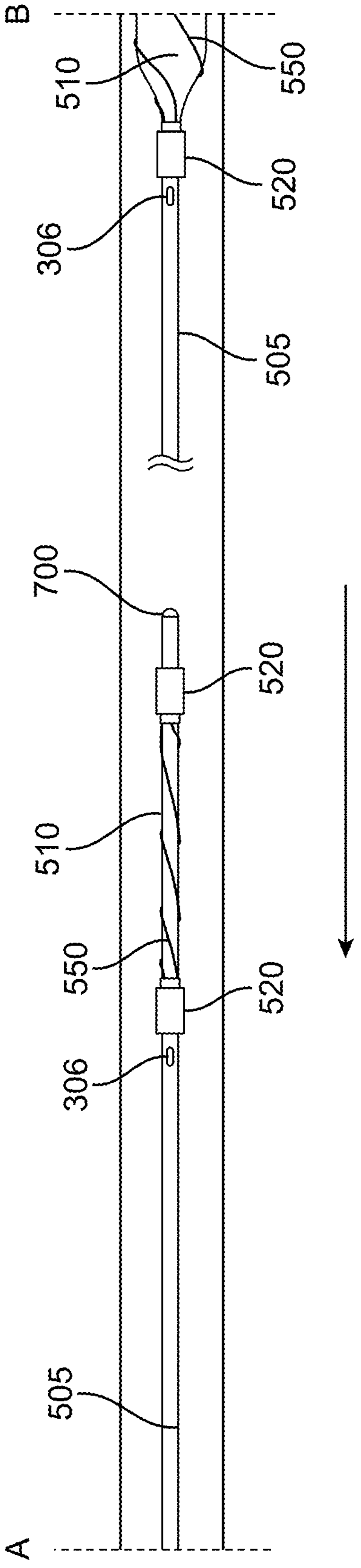

Once treatment is finished, the device is removed by first deflating the balloon 510, withdrawing the angular offset abrasion elements 550 from contact with the vessel wall (see righthand end of FIG. 31F). Continued deflation—in some cases assisted by the restoring force of the angular offset abrasion elements, the balloon treatment device further collapses into a stowed condition as shown in the central portion of FIG. 31F. The balloon treatment device 700 continues to be withdrawn as indicated by the arrow in FIG. 31F.

Figure 32A:
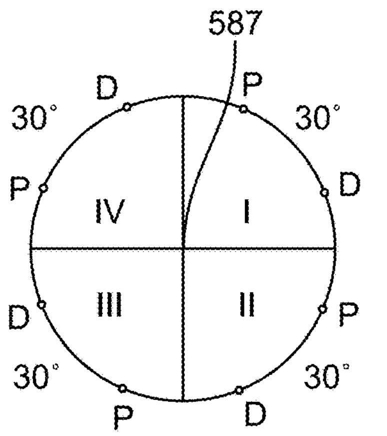
FIG. 32A is an end view of an arrangement of angular offset abrasion coils about a longitudinal axis where the angular offset is 30 degrees.

FIG. 32A is an end on view of a representative balloon therapy device similar to device 700 with quadrants 1-IV arranged about the longitudinal axis 587 of the catheter 505. As shown, the proximal and distal ends of the abrasion elements have an angular offset of 30 degrees.

Figure 32B:
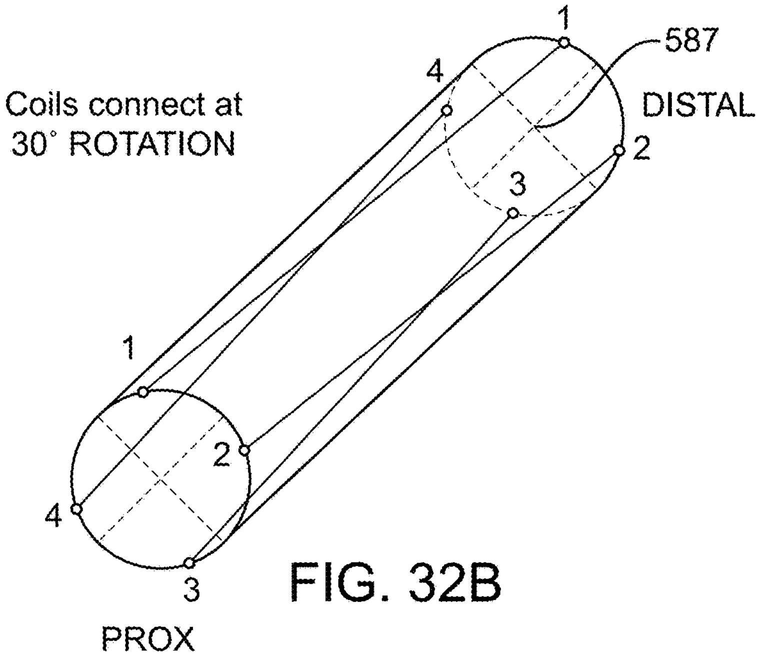
FIG. 32B is a perspective view of the abrasion elements of FIG. 32A as arranged along an inflated balloon along the catheter longitudinal axis.
Figure 32C:
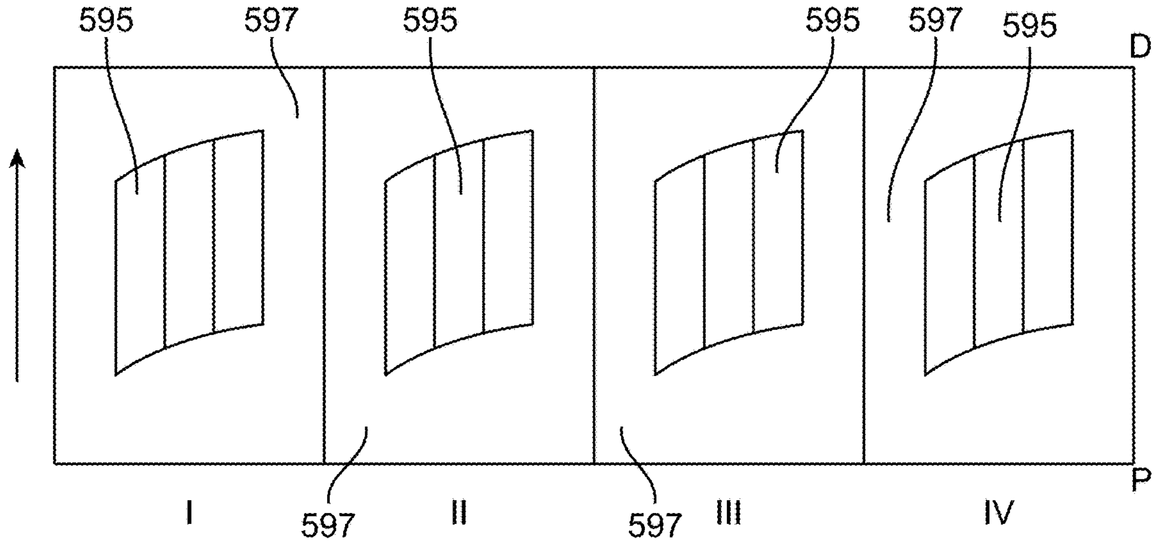
FIG. 32C is a perspective view of the segmented abrasion areas formed in a vessel by the offset abrasion elements of FIGS. 32A and 32B.

FIG. 32B is a perspective view of the balloon treatment device of FIG. 32A showing the arrangement of each one of the abrasion elements 550 moving along the balloon 510 outer surface about the catheter longitudinal axis 587.

FIG. 32C is a perspective view of the treated wall of a vessel after the movement of the partially inflated balloon to form the closure zone. As a result of the uniform spacing and offset alignment (i.e., each zone is similar offset) between the different abrasion elements, there are produced an arrangement of segmented abrasion areas 595 formed by the balloon treatment device of FIGS. 32A and 32B. Adjacent untreated areas 597 are present between the abrasion areas 595 in relation to the spacing between the adjacent offset abrasion elements. As is clear between this embodiment and those above with FIGS. 24A-25C a large number of different sizes of abrasion areas, spacing between as well as a continuous or nearly continuous configuration are possible using the various alternative offset abrasion elements described herein.

Figure 33:
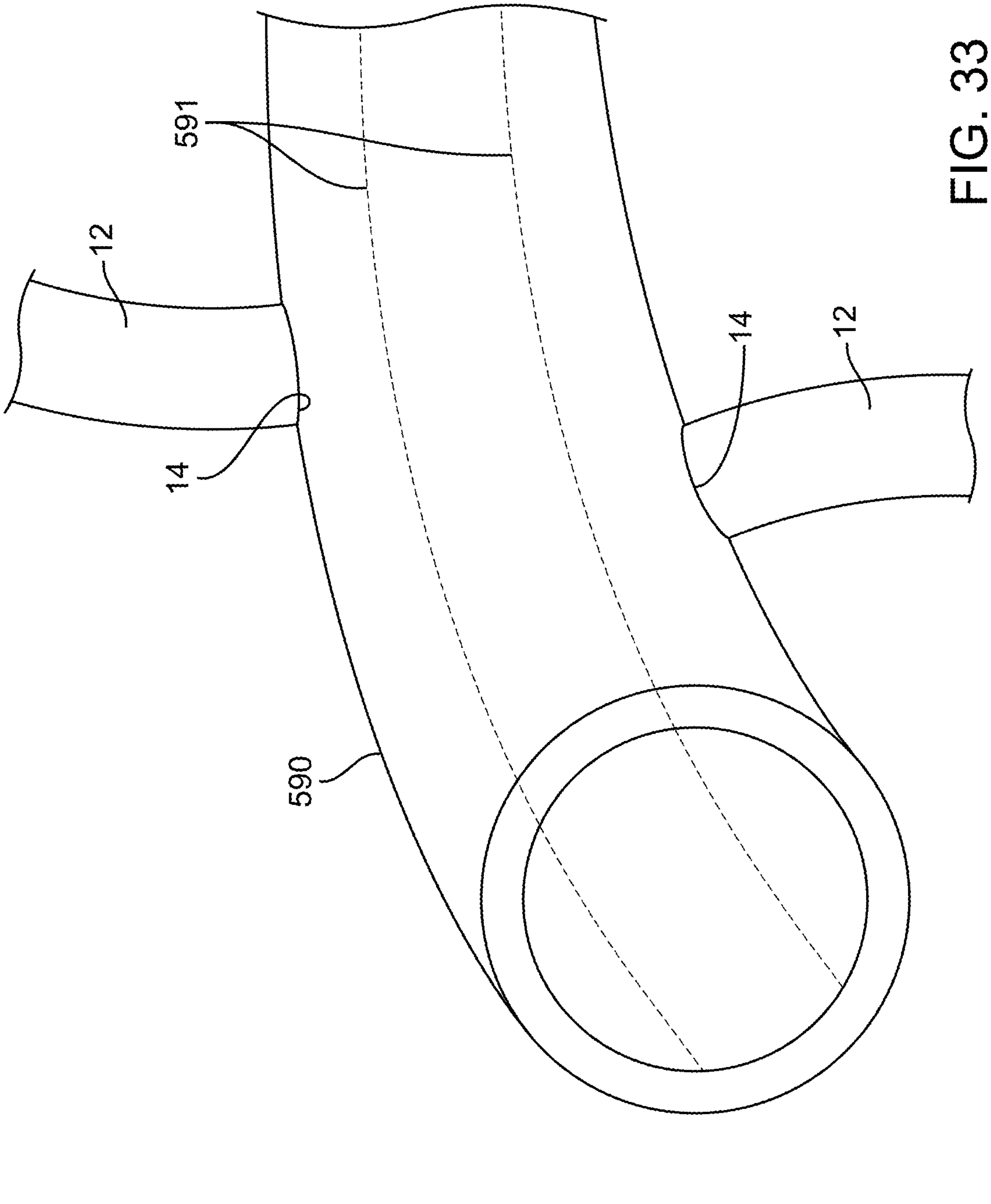
FIG. 33 (PRIOR ART)
FIG. 33 is a perspective view of a vessel having a non-angular offset abrasion line formed similar to FIG. 22 that does not contact any ostia of a side vessel.

While desiring not to be bound by theory, experiments performed using embodiments of a balloon treatment device 700 have produced unexpected results. In addition to the beneficial use of venospasm, along with active aspiration in order to improve the closure performance of devices described herein, the abrasion areas produced by the angular offset abrasion element may provide an additional benefit. FIG. 33 is a perspective view of a vessel having a non-angular offset abrasion line formed similar to FIG. 22. Note that neither of the abrasion lines 2110 contact an ostia 14 of any side vessel 12.

Figure 34:
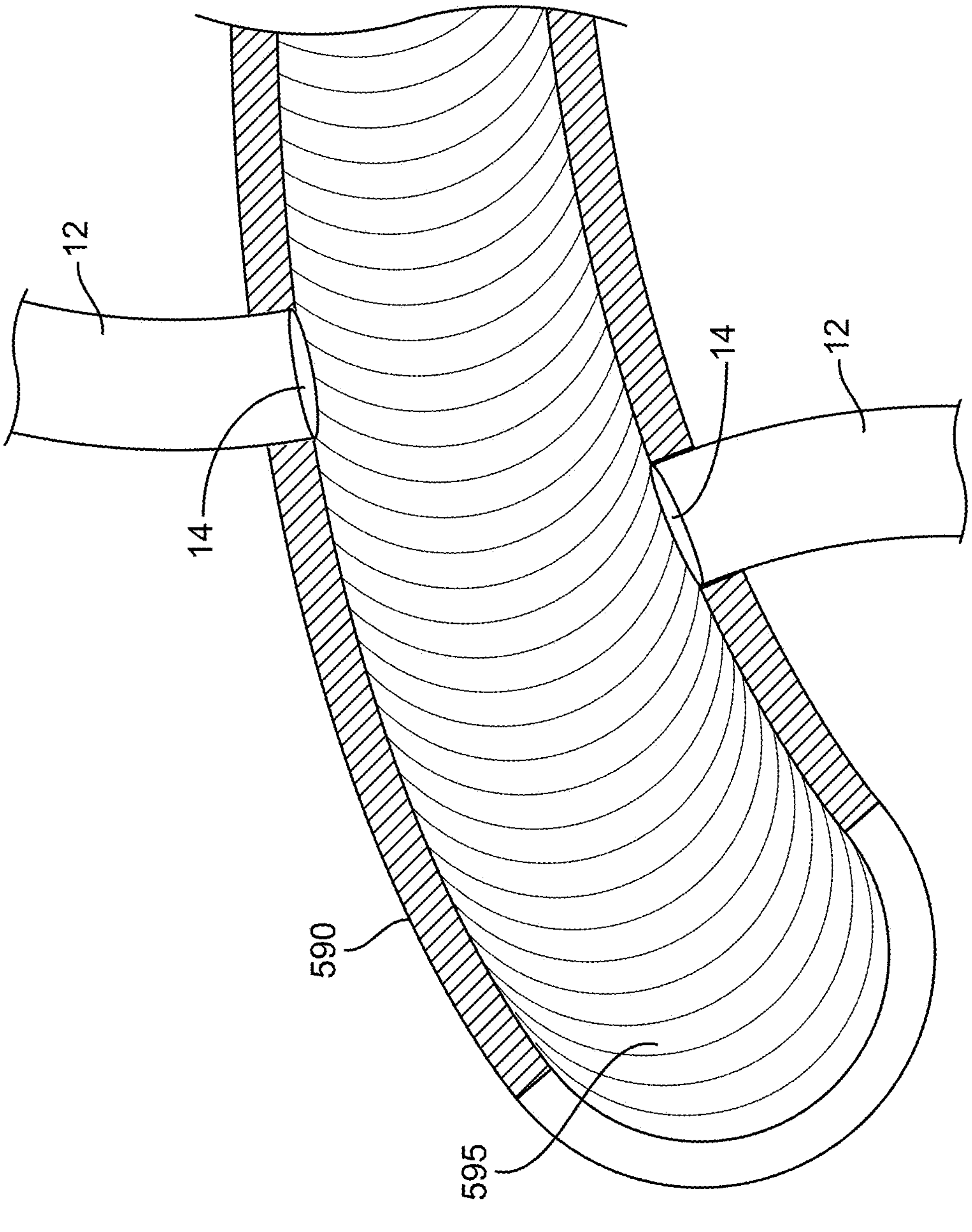
FIG. 34 is a perspective view of a vessel having an abrasion area formed by an angular offset abrasion element that does contact and induce spasm and closure of the ostia of side vessels.

In contrast, FIG. 34 is a perspective view of a vessel 590 having an abrasion area 595 formed by an angular offset abrasion element 550 that does contact and induce spasm and closure of the ostia 14 of side vessels 12. It is believed that the contact between an ostia of a side vessel and an abrasion element with cause closure of the ostia. As a result, this closure increases the probability that the closure agent remains with the target vessel and does not spread into other deep veins or other non-target vessels of the venous tree. Such isolation could be of particular importance with performing a vessel closure with important structures to be protected.

As described above, the devices described herein can be used to treat more than one closure zone or be developed into a two-balloon treatment system. Additionally or optionally, the balloon therapy device may also be provided with a guide wire lumen.

In some alternative embodiments, one or more aspects of the inventive coiled abrasion element balloon-based closure device and related methods may be modified to include one or more aspects, details or variations such as described in co-pending commonly assigned International Publication Number WO 2024/0908045 entitled "Catheters and Related Methods for Aspiration and Controlled Delivery of Closure Agents" published on May 10, 2024, and invented by Ali Golshan. Still further, additional details of one or more variations or optional implementations may also be described in U.S. Pat. Nos. 3,625,793, 4,983,166, 5,087,244, 6,264,633, 5,919,163, US Patent Application Publication US 2003/0120256, US Patent Application Publication US 2005/0033227, US Patent Application Publication US 2005/0059931, and U.S. Pat. No. 5,676,962, the disclosure of each of which is incorporated herein by reference in its entirety.

Additionally or optionally specific details of WO Appl. '8045 may be provided in various alternative embodiments where an angular offset abrasion element balloon device is adapted and configures, such as for example, to have one or more or a combination of: (i) a two balloon treatment device similar to WO Appl. '8045 FIG. 12B with only offset abrasion elements arranged about the distal most balloon along with (ii) capacity to perform a variety of variations to the two balloon methods of WO Appl. '8045 FIGS. 32-35 alone or in combination with the side vessel closure technique described above in FIG. 34 of the present application; (iii) use of alternative offset abrasion element two balloon treatment devices in the anatomical scenarios of FIGS. 36A and 36B of WO Appl. '8045; and (iv) adaptation of the angular offset abrasion element treatment devices of a two balloon configuration adapted and configured to perform methods as in WO Appl. '8045 FIGS. 38A-38F and 39.

Although an embodiment has been described with reference to specific example embodiments, it will be evident that various modifications and changes may be made to these embodiments without departing from the scope of the present disclosure. Accordingly, the specification and drawings are to be regarded in an illustrative rather than a restrictive sense. The accompanying drawings that form a part hereof show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Various aspects of the disclosure have been described above. It should be apparent that the teachings herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein.

While the invention has been described in connection with various aspects, it will be understood that the embodiments disclosed herein are capable of further modifications. This application is intended to cover any variations, uses or adaptation of the invention following, in general, the principles of the invention, and including such departures from the present disclosure as come within the known and customary practice within the art to which the invention pertains.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats, and that this data represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for treatment of an incompetent vein, comprising:

a catheter shaft having a proximal end and a distal end;

a hub coupled to the proximal end;

a balloon on the catheter shaft adjacent to the distal end, wherein the balloon is a compliant balloon;

an atraumatic tip on the distal end;

an aperture in the catheter shaft proximal to the balloon;

an inflation lumen within the catheter shaft in fluid communication with an interior volume of the balloon and an inflation port on the hub; and a fluid lumen within the catheter shaft in fluid communication with the aperture and a fluid port on the hub; and a plurality of angular offset abrasion elements extending along the catheter shaft and over the balloon, each one of the plurality of angular offset abrasion elements having a proximal terminal end, a distal terminal end and a tissue contacting surface between the proximal terminal end and the distal terminal end, wherein the tissue contacting surface extends along the balloon on a path, wherein the path of the tissue contacting surface between the proximal terminal end and the distal terminal end is less than 360 degrees relative to a perimeter of the balloon, further wherein the proximal terminal end of each of the plurality of angular offset abrasion elements is coupled to the catheter shaft proximal to a proximal most end of the balloon and the distal terminal end of each one of the plurality of angular offset abrasion elements is coupled to the catheter shaft distal to a distal most end of the balloon, further wherein the distal terminal end of each one of the plurality of angular offset abrasion elements is at an angular offset from the respective proximal terminal end of each one of the plurality of angular offset abrasion elements and relative to a longitudinal axis of the catheter shaft.

2. The device of claim 1, wherein the angular offset of each distal terminal end of each one of the plurality of angular offset abrasion elements is less than 360 degrees.

3. The device of claim 1, wherein the angular offset is from 2 degrees to 90 degrees, less than 180 degrees, 40 degrees to 60 degrees, or 80 degrees to 100 degrees.

4. The device of claim 1, wherein the number of angular offset abrasion elements in the plurality of angular abrasion elements is 2, and the angular offset of each one of the angular abrasion elements is from 2 degrees to 180 degrees.

5. The device of claim 1, wherein the number of angular offset abrasion elements in the plurality of angular abrasion elements is 3, and the angular offset of each one of the angular abrasion elements is from 2 degrees to 60 degrees.

6. The device of claim 1, wherein the number of angular offset abrasion elements in the plurality of angular abrasion elements is 4, and the angular offset of each one of the angular abrasion elements is from 2 degrees to 90 degrees.

7. The device of claim 1, wherein the number of angular offset abrasion elements in the plurality of angular abrasion elements is 4, and the angular offset of each one of the angular abrasion elements is from 2 degrees to 50 degrees.

8. The device of claim 1, further wherein the angular offset of the distal terminal end of each one of the plurality of angular offset abrasion elements is selected so that, in use within the incompetent vein, the plurality of angular offset abrasion elements creates a plurality of spaced apart abrasion areas along a closure zone.

9. The device of claim 1, further wherein the angular offset of the distal terminal end of each one of the plurality of angular offset abrasion elements is selected so that, in use within the incompetent vein, the plurality of angular offset abrasion elements creates a plurality of continuous or nearly continuous abrasion areas along a closure zone.

10. The device of claim 1, wherein the number of the plurality of angular offset abrasion elements is four, wherein a first of the four angular offset abrasion elements has the proximal terminal end coupled to the catheter shaft at a 12 o'clock position and the corresponding distal terminal end is coupled to the catheter shaft at a 3 o'clock position, a second of the four angular offset abrasion elements has the proximal terminal end coupled to the catheter shaft at a 3 o'clock position and the corresponding distal terminal end is coupled to the catheter shaft at a 6 o'clock position, a third of the four angular offset abrasion elements has the proximal terminal end coupled to the catheter shaft at a 6 o'clock position and the corresponding distal terminal end is coupled to the catheter shaft at a 9 o'clock position and the fourth of the four angular offset abrasion elements has the proximal terminal end coupled to the catheter shaft at a 9 o'clock position and the corresponding distal terminal end is coupled to the catheter shaft at a 12 o'clock position.

11. A device for treatment of an incompetent vein, comprising:

a catheter shaft having a proximal end and a distal end;

a hub coupled to the proximal end;

a balloon on the catheter shaft adjacent to the distal end, wherein the balloon is a compliant balloon;

an atraumatic tip on the distal end;

an aperture in the catheter shaft proximal to the balloon;

an inflation lumen within the catheter shaft in fluid communication with an interior volume of the balloon and an inflation port on the hub; and a fluid lumen within the catheter shaft in fluid communication with the aperture and a fluid port on the hub;

four angular offset abrasion elements extending along the catheter shaft and over an active area of the balloon, each one of the four angular offset abrasion elements having a proximal terminal end, and a distal terminal end, wherein the proximal terminal end of each of the four angular offset abrasion elements is coupled to the catheter shaft proximal to the active area of the balloon and the distal terminal end of each of the four angular offset abrasion elements is coupled to the catheter shaft distal to the active area of the balloon; and wherein a position of the proximal terminal end of each one of the four angular offset abrasion elements is at an angular offset to a position of the distal terminal end of each one of the four angular offset abrasion elements, and a position of the distal terminal end of each of the four angular offset abrasion elements forms an angular offset relative to a longitudinal axis of the catheter shaft, further wherein the angular offset of each one of the four angular offset abrasion elements is from 2 degrees to 90 degrees.

12. The device of claim 11, wherein a first of the four angular offset abrasion elements has the proximal terminal end coupled to the catheter shaft at a 12 o'clock position and the corresponding distal terminal end is coupled to the catheter shaft at a 3 o'clock position, a second of the four angular offset abrasion elements has the proximal terminal end coupled to the catheter shaft at a 3 o'clock position and the corresponding distal terminal end is coupled to the catheter shaft at a 6 o'clock position, a third of the four angular offset abrasion elements has the proximal terminal end coupled to the catheter shaft at a 6 o'clock position and the corresponding distal terminal end is coupled to the catheter shaft at a 9 o'clock position and the fourth of the four angular offset abrasion elements has the proximal terminal end coupled to the catheter shaft at a 9 o'clock position and the corresponding distal terminal end is coupled to the catheter shaft at a 12 o'clock position.

13. The device of claim 11, wherein each one of the angular offset abrasion elements has a coil portion having a pitch and a coil outer diameter.

14. The device of claim 13, wherein the coil portion of each one of the angular offset abrasion elements is between non-coil portions of the angular offset abrasion element.

15. The device of claim 13, wherein the coil portion of each one of the angular offset abrasion elements is at least as long as the active area of the balloon.

16. The device of claim 11, wherein each of the angular offset abrasion elements is formed of a wire having a diameter of about 0.05 mm wound into a coil having an outer diameter of 0.2 mm and a pitch of 0.05 mm.

17. The device of claim 13, wherein the coil portion of each angular offset abrasion element extends from the proximal terminal end to the distal terminal end.

18. The device of claim 13, wherein, in use within the incompetent vein, when the balloon inflates to an occlusion volume having a diameter from 6 mm to 12 mm, the coil portion within each one of the angular offset abrasion elements remains within an elastic response zone.

19. The device of claim 11, wherein the active area of the balloon has a length of 12-15 mm and the length of each angular offset abrasion element from the proximal terminal end to the distal terminal end is 20 mm to 40 mm.

20. The device of claim 19, wherein the proximal terminal end and the distal terminal end of each of the angular offset abrasion elements is coupled to the balloon adjacent to the active area of the balloon.

* * * * *